(12) United States Patent
Johnston

(10) Patent No.: US 11,426,451 B2
(45) Date of Patent: Aug. 30, 2022

(54) METHODS AND COMPOSITIONS RELATED TO COMBINED TREATMENT WITH ANTIINFLAMMATORIES AND SYNTHETIC NANOCARRIERS COMPRISING AN IMMUNOSUPPRESSANT

(71) Applicants: Selecta Biosciences, Inc., Watertown, MA (US); Lloyd Johnston, Belmont, MA (US)

(72) Inventor: Lloyd Johnston, Belmont, MA (US)

(73) Assignee: Selecta Biosciences, Inc., Watertown, MA (US)

( * ) Notice: Subject to any disclaimer, the term of this patent is extended or adjusted under 35 U.S.C. 154(b) by 0 days.

(21) Appl. No.: 15/917,742

(22) Filed: Mar. 11, 2018

(65) Prior Publication Data

US 2018/0289776 A1 Oct. 11, 2018

Related U.S. Application Data

(60) Provisional application No. 62/470,250, filed on Mar. 11, 2017.

(51) Int. Cl.

| | | |
|---|---|---|
| *A61K 38/44* | (2006.01) | |
| *A61K 31/436* | (2006.01) | |
| *A61K 9/51* | (2006.01) | |
| *A61K 45/00* | (2006.01) | |
| *A61K 38/43* | (2006.01) | |
| *A61P 29/00* | (2006.01) | |
| *A61K 31/165* | (2006.01) | |
| *A61K 31/192* | (2006.01) | |
| *A61K 31/445* | (2006.01) | |
| *A61K 31/573* | (2006.01) | |
| *A61K 45/06* | (2006.01) | |

(52) U.S. Cl.
CPC ............... *A61K 38/44* (2013.01); *A61K 9/51* (2013.01); *A61K 9/5153* (2013.01); *A61K 38/43* (2013.01); *A61K 45/00* (2013.01); *A61P 29/00* (2018.01); *A61K 31/165* (2013.01); *A61K 31/192* (2013.01); *A61K 31/436* (2013.01); *A61K 31/445* (2013.01); *A61K 31/573* (2013.01); *A61K 45/06* (2013.01); *A61K 2300/00* (2013.01); *C12Y 107/03003* (2013.01)

(58) Field of Classification Search
None
See application file for complete search history.

(56) References Cited

U.S. PATENT DOCUMENTS

| | | |
|---|---|---|
| 5,100,669 A | 3/1992 | Hyon et al. |
| 5,543,158 A | 8/1996 | Gref et al. |
| 5,679,347 A | 10/1997 | Porcelli et al. |
| 5,700,674 A | 12/1997 | Koyama et al. |
| 5,762,904 A | 6/1998 | Okada et al. |
| 5,912,017 A | 6/1999 | Mathiowitz et al. |
| 6,009,548 A | 12/1999 | Chen et al. |
| 6,060,082 A | 5/2000 | Chen et al. |
| 6,197,229 B1 | 3/2001 | Ando et al. |
| 6,251,957 B1 | 6/2001 | Wilson |
| 6,306,640 B1 | 10/2001 | Nicolette |
| 6,387,397 B1 | 5/2002 | Chen et al. |
| 6,468,771 B1 | 10/2002 | Einerhand et al. |
| 6,838,089 B1 | 1/2005 | Carlsson et al. |
| 6,913,915 B2 | 7/2005 | Ensor et al. |
| 7,045,508 B2 | 5/2006 | Scaria |
| 7,884,109 B2 | 2/2011 | Ohlmeyer et al. |
| 8,455,510 B2 | 6/2013 | Nan et al. |
| 8,568,487 B2 | 10/2013 | Witt et al. |
| 8,629,151 B2 | 1/2014 | Zepp et al. |
| 8,652,487 B2 | 2/2014 | Maldonado et al. |
| 8,654,487 B2 | 2/2014 | Mikani et al. |
| 8,865,487 B2 | 10/2014 | Kostka et al. |
| 9,005,665 B2 | 4/2015 | Gourapura |
| 9,006,254 B2 | 4/2015 | Zepp et al. |
| 9,017,697 B2 | 4/2015 | Thomas |
| 9,066,978 B2 | 6/2015 | Ilyinskii et al. |
| 9,265,815 B2 | 2/2016 | Fraser et al. |
| 9,276,815 B2 | 3/2016 | Anumala et al. |
| 9,289,476 B2 | 3/2016 | Fraser et al. |
| 9,289,477 B2 | 3/2016 | Fraser et al. |
| 9,295,718 B2 | 3/2016 | Fraser et al. |
| 9,377,454 B2 | 6/2016 | Rosario-Jansen et al. |

(Continued)

FOREIGN PATENT DOCUMENTS

| | | |
|---|---|---|
| BR | PI0808635 A2 | 8/2014 |
| BR | 112013027500 A2 | 1/2017 |

(Continued)

OTHER PUBLICATIONS

Czock et al., "Pharmacokinetics and Pharmacodynamics of Systemically Administered Glucocorticoids", Clinical Pharmacokinetics, vol. 44, pp. 61-70). (Year: 2005).*
Davis et al., "Hypouricaemic effect of polyethyleneglycol modified urate oxidase", The Lancet, vol. 318, p. 281-283 (Year: 1981).*
International Search Report and Written Opinion dated Jun. 6, 2018 for Application No. PCT/US2018/021897.
International Preliminary Report on Patentability dated Sep. 26, 2019 for Application No. PCT/US2018/021897.
[No Author Listed] Selecta Biosciences Announces Dosing of First Patient in Phase 1b Clinical Trial of SEL-212, Designed to be The First Non-Immunogenic Biologic Treatment for Gout. Press Release. Dec. 23, 2015. Retrieved from the Internet via http://selectabio.com/2015/12/23/selecta-biosciences-announces-dosing-of-first-patient-in-phase-1b-clinical-trial-of-sel-212-designed-to-be-the-first-non-immunogenic-biologic-treatment-for-gout. Last access on May 10, 2017.

(Continued)

*Primary Examiner* — Michelle F. Paguio Frising
(74) *Attorney, Agent, or Firm* — Wolf, Greenfield & Sacks, P.C.

(57) ABSTRACT

Provided herein are methods and compositions, such as kits, related to compositions comprising synthetic nanocarriers comprising an immunosuppressant and compositions comprising an uricase and a composition comprising an anti-inflammatory therapeutic. Also provided herein are methods and compositions for the treatment of subjects in need of administration or treatment with the uricase.

12 Claims, 8 Drawing Sheets

(56) References Cited

U.S. PATENT DOCUMENTS

| | | |
|---|---|---|
| 9,636,309 B2 | 5/2017 | Carlyle et al. |
| 9,764,031 B2 | 9/2017 | Ilyinskii et al. |
| 9,884,112 B2 | 2/2018 | Zepp et al. |
| 9,987,354 B2 | 6/2018 | Fraser et al. |
| 9,993,548 B2 | 6/2018 | Maldonado et al. |
| 9,994,443 B2 | 6/2018 | Zepp et al. |
| 10,004,802 B2 | 6/2018 | Kishimoto et al. |
| 10,039,822 B2 | 8/2018 | Altreuter et al. |
| 10,046,064 B2 | 8/2018 | Kishimoto |
| 10,071,114 B2 | 9/2018 | Kishimoto |
| 10,335,395 B2 | 7/2019 | Kishimoto |
| 10,357,482 B2 | 7/2019 | Maldonado |
| 10,357,483 B2 | 7/2019 | Maldonado et al. |
| 10,420,835 B2 | 9/2019 | Fraser et al. |
| 10,434,088 B2 | 10/2019 | Maldonado et al. |
| 10,441,651 B2 | 10/2019 | Kishimoto et al. |
| 10,668,053 B2 | 6/2020 | Maldonado |
| 2002/0014242 A1 | 2/2002 | Scaria et al. |
| 2002/0019361 A1 | 2/2002 | Scaria |
| 2002/0086049 A1 | 7/2002 | Bolton et al. |
| 2002/0095135 A1 | 7/2002 | Meeker |
| 2004/0204379 A1 | 1/2004 | Cheng et al. |
| 2004/0038406 A1 | 2/2004 | Unger et al. |
| 2004/0043483 A1 | 3/2004 | Qian et al. |
| 2006/0002852 A1 | 1/2006 | Saltzman et al. |
| 2006/0002971 A1 | 1/2006 | Saltzman et al. |
| 2006/0147432 A1 | 7/2006 | Moore et al. |
| 2006/0210638 A1 | 9/2006 | Liversidge et al. |
| 2006/0222652 A1 | 10/2006 | Sebbel et al. |
| 2006/0251677 A1 | 11/2006 | Bachmann et al. |
| 2006/0251710 A1 | 11/2006 | Kwon et al. |
| 2006/0251711 A1 | 11/2006 | Konduri et al. |
| 2006/0269540 A1 | 11/2006 | Robert et al. |
| 2007/0110685 A1 | 5/2007 | Auspitz et al. |
| 2007/0190032 A1 | 8/2007 | Coffey et al. |
| 2007/0254897 A1 | 11/2007 | Gjorstrup |
| 2008/0031899 A1 | 2/2008 | Reddy et al. |
| 2008/0145441 A1 | 6/2008 | Penades et al. |
| 2008/0160089 A1 | 7/2008 | Vitiello et al. |
| 2008/0254045 A1 | 10/2008 | Donda et al. |
| 2008/0311140 A1 | 12/2008 | Lee et al. |
| 2009/0004259 A1 | 1/2009 | Rabinovich et al. |
| 2009/0028910 A1 | 1/2009 | DeSimone et al. |
| 2009/0028948 A1 | 1/2009 | Cammarano et al. |
| 2009/0074828 A1 | 3/2009 | Frank et al. |
| 2009/0082260 A1 | 3/2009 | Lamb et al. |
| 2009/0155292 A1 | 6/2009 | Santamaria et al. |
| 2009/0226525 A1 | 9/2009 | de los Rios et al. |
| 2010/0008932 A1 | 1/2010 | Bensussan et al. |
| 2010/0028450 A1 | 2/2010 | Vasu et al. |
| 2010/0055076 A1 | 3/2010 | Lim et al. |
| 2010/0055189 A1 | 3/2010 | Hubbell et al. |
| 2010/0062968 A1 | 3/2010 | Pulendran et al. |
| 2010/0068261 A1 | 3/2010 | Tamarkin et al. |
| 2010/0068286 A1 | 3/2010 | Troiano et al. |
| 2010/0069426 A1 | 3/2010 | Zale et al. |
| 2010/0080816 A1 | 4/2010 | Hadeiba et al. |
| 2010/0112077 A1 | 5/2010 | Desai et al. |
| 2010/0129392 A1 | 5/2010 | Shi et al. |
| 2010/0129439 A1 | 5/2010 | Alexis et al. |
| 2010/0151000 A1 | 6/2010 | Thomas et al. |
| 2010/0172994 A1 | 7/2010 | Sigmund et al. |
| 2010/0183602 A1 | 7/2010 | Carballido Herrera et al. |
| 2010/0183727 A1 | 7/2010 | Iannacone et al. |
| 2010/0188727 A1 | 7/2010 | Fagerstroem et al. |
| 2010/0196401 A1 | 8/2010 | Scaria |
| 2010/0233197 A1 | 9/2010 | Wakatsuki Pedersen et al. |
| 2010/0233251 A1 | 9/2010 | Von Andrian et al. |
| 2010/0273220 A1 | 10/2010 | Yanik et al. |
| 2010/0303850 A1 | 12/2010 | Lipford et al. |
| 2011/0004148 A1 | 1/2011 | Ishii et al. |
| 2011/0020388 A1 | 1/2011 | Zepp et al. |
| 2011/0027217 A1 | 2/2011 | Zepp et al. |
| 2011/0070153 A1 | 3/2011 | Hyde et al. |
| 2011/0070154 A1 | 3/2011 | Hyde et al. |
| 2011/0076273 A1 | 3/2011 | Adler et al. |
| 2011/0110965 A1 | 5/2011 | Fraser et al. |
| 2011/0166172 A1 | 7/2011 | Nan et al. |
| 2011/0171248 A1 | 7/2011 | Pittet et al. |
| 2011/0223201 A1 | 9/2011 | Lipford et al. |
| 2011/0243976 A1 | 10/2011 | Bagnoli et al. |
| 2011/0262491 A1 | 10/2011 | Keegan et al. |
| 2011/0272836 A1 | 11/2011 | Keegan et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2012/0014966 A1 | 1/2012 | Solinger et al. |
| 2012/0027806 A1 | 2/2012 | Ilyinskii et al. |
| 2012/0027808 A1 | 2/2012 | Iannacone et al. |
| 2012/0039989 A1 | 2/2012 | Hubbell et al. |
| 2012/0058153 A1 | 3/2012 | Ilyinskii et al. |
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0076831 A1 | 3/2012 | Miller et al. |
| 2012/0077860 A1 | 3/2012 | Garcia |
| 2012/0114677 A1 | 5/2012 | Zepp et al. |
| 2012/0148612 A1 | 6/2012 | Hafner et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1 | 11/2012 | Fraser et al. |
| 2012/0276155 A1 | 11/2012 | Kishimoto et al. |
| 2012/0276156 A1 | 11/2012 | Fraser et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2012/0308563 A1 | 12/2012 | Arya et al. |
| 2013/0028857 A1 | 1/2013 | Gao et al. |
| 2013/0028941 A1 | 1/2013 | Altreuter et al. |
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado et al. |
| 2013/0059009 A1 | 3/2013 | Kishimoto et al. |
| 2014/0030344 A1 | 1/2014 | Zepp et al. |
| 2014/0199340 A1 | 7/2014 | Maldonado |
| 2014/0212462 A1 | 7/2014 | Kang et al. |
| 2014/0242173 A1 | 8/2014 | Zepp et al. |
| 2014/0294982 A1 | 10/2014 | Freund et al. |
| 2014/0328854 A1 | 11/2014 | Maldonado et al. |
| 2014/0328921 A1 | 11/2014 | Maldonado |
| 2014/0328922 A1 | 11/2014 | Maldonado |
| 2014/0328923 A1 | 11/2014 | Maldonado et al. |
| 2014/0328924 A1 | 11/2014 | Kishimoto |
| 2014/0335186 A1 | 11/2014 | Kishimoto et al. |
| 2014/0336245 A1 | 11/2014 | Mingozzi et al. |
| 2014/0356361 A1 | 12/2014 | Maldonado et al. |
| 2015/0024007 A1 | 1/2015 | Hessel et al. |
| 2015/0099707 A1 | 4/2015 | Pastan et al. |
| 2015/0111955 A1 | 4/2015 | High et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328300 A1 | 11/2015 | Zepp et al. |
| 2015/0328309 A1 | 11/2015 | Ilyinskii et al. |
| 2015/0328333 A1 | 11/2015 | Fraser et al. |
| 2015/0335762 A1 | 11/2015 | Fraser et al. |
| 2015/0359865 A1 | 12/2015 | Kishimoto |
| 2015/0374815 A1 | 12/2015 | Kishimoto et al. |
| 2016/0022650 A1 | 1/2016 | Fraser et al. |

(56) References Cited

U.S. PATENT DOCUMENTS

| | | |
|---|---|---|
| 2016/0030554 A1 | 2/2016 | Kishimoto et al. |
| 2016/0030555 A1 | 2/2016 | Kishimoto et al. |
| 2016/0067228 A1 | 3/2016 | Kishimoto et al. |
| 2016/0074372 A1 | 3/2016 | Kishimoto |
| 2016/0074427 A1 | 3/2016 | Kishimoto |
| 2016/0074531 A1 | 3/2016 | Kishimoto |
| 2016/0074532 A1 | 3/2016 | Kishimoto |
| 2016/0128986 A1 | 5/2016 | O'Neil et al. |
| 2016/0128987 A1 | 5/2016 | Griset et al. |
| 2016/0220501 A1 | 8/2016 | Fraser et al. |
| 2016/0243253 A1 | 8/2016 | Fraser et al. |
| 2016/0256401 A1 | 9/2016 | Fraser et al. |
| 2016/0279234 A1 | 9/2016 | Kishimoto et al. |
| 2017/0224620 A1 | 8/2017 | Zale et al. |
| 2017/0258927 A1 | 9/2017 | Johnston |
| 2017/0349433 A1 | 12/2017 | Lipford et al. |
| 2018/0043023 A1 | 2/2018 | Ilyinski et al. |
| 2018/0071394 A1 | 3/2018 | O'Neil et al. |
| 2018/0085319 A1 | 3/2018 | Kishimoto |
| 2018/0193482 A1 | 7/2018 | Ilyinski et al. |
| 2018/0256709 A1 | 9/2018 | Zepp et al. |
| 2019/0076458 A1 | 3/2019 | Kishimoto et al. |
| 2019/0076522 A1 | 3/2019 | Altreuter et al. |
| 2019/0142974 A1 | 5/2019 | Ilyinskii et al. |
| 2020/0038462 A1 | 2/2020 | Keller et al. |
| 2020/0038463 A1 | 2/2020 | Keller et al. |
| 2020/0069659 A1 | 3/2020 | Kishimoto |
| 2020/0069660 A1 | 3/2020 | Maldonado et al. |
| 2020/0078341 A1 | 3/2020 | Maldonado |
| 2020/0101154 A1 | 4/2020 | Fraser et al. |
| 2020/0101155 A1 | 4/2020 | Kishimoto et al. |
| 2020/0113874 A1 | 4/2020 | Maldonado et al. |
| 2020/0360350 A1 | 11/2020 | Maldonado |
| 2020/0360453 A1 | 11/2020 | Kishimoto et al. |
| 2020/0390718 A1 | 12/2020 | Kishimoto et al. |
| 2020/0399628 A1 | 12/2020 | Johnston et al. |
| 2021/0154324 A1 | 5/2021 | Ilyinskii et al. |
| 2021/0187081 A1 | 6/2021 | Johnston et al. |
| 2021/0308058 A1 | 10/2021 | Johnston |

FOREIGN PATENT DOCUMENTS

| | | |
|---|---|---|
| BR | 112015023793 A2 | 7/2017 |
| BR | 112015027279 A2 | 9/2017 |
| CA | 2815422 A1 | 4/2012 |
| CN | 1335398 | 2/2002 |
| CN | 1391479 | 1/2003 |
| CN | 1678188 A | 10/2005 |
| CN | 101437491 A | 5/2009 |
| CN | 101484461 A | 7/2009 |
| CN | 101646418 A | 2/2010 |
| CN | 101703781 A | 5/2010 |
| CN | 101730526 A | 6/2010 |
| CN | 101861165 A | 10/2010 |
| CN | 101990429 A | 3/2011 |
| CN | 102202653 A | 9/2011 |
| CN | 102740834 A | 10/2012 |
| CN | 103282380 A | 9/2013 |
| CN | 102871966 B | 11/2013 |
| CN | 103491957 A | 1/2014 |
| CN | 103501793 | 1/2014 |
| CN | 103501820 A | 1/2014 |
| CN | 105283175 | 1/2016 |
| EP | 0759941 B1 | 9/2000 |
| EP | 1932538 A1 | 6/2008 |
| EP | 2073848 A2 | 7/2009 |
| EP | 2217269 A2 | 8/2010 |
| EP | 2345412 A1 | 7/2011 |
| EP | 2522338 A2 | 11/2012 |
| EP | 3426285 | 1/2019 |
| JP | H01-502909 A | 10/1989 |
| JP | H10-507758 A | 7/1998 |
| JP | 2005-516893 A | 6/2005 |
| JP | 2006-257095 | 9/2006 |
| JP | 2007-532517 A | 11/2007 |
| JP | 2008-515806 | 5/2008 |
| JP | 2008-532953 A | 8/2008 |
| JP | 2009-527566 A | 7/2009 |
| JP | 2009-531068 | 9/2009 |
| JP | 2010-505883 | 2/2010 |
| JP | 2010-100578 A | 5/2010 |
| JP | 2010-514805 | 5/2010 |
| JP | 2010-533160 A | 10/2010 |
| JP | 2010-535025 | 11/2010 |
| JP | 2011-500569 | 1/2011 |
| JP | 2011-512326 A | 4/2011 |
| JP | 2012-502930 A | 2/2012 |
| JP | 2012-512175 A | 5/2012 |
| JP | 2012-515722 A | 7/2012 |
| JP | 2012-516691 A | 7/2012 |
| JP | 2013-541504 A | 11/2013 |
| JP | 2014-517828 A | 4/2014 |
| JP | 2014-513092 A | 5/2014 |
| JP | 2014-513102 A | 5/2014 |
| JP | 2014-513722 A | 6/2014 |
| JP | 2014-514331 A | 6/2014 |
| JP | 2014-514332 A | 6/2014 |
| JP | 2014-514333 A | 6/2014 |
| JP | 2014-514334 A | 6/2014 |
| JP | 2017-122113 | 7/2017 |
| KR | 10-2010-0099849 A | 9/2010 |
| WO | WO 88/06451 A1 | 9/1988 |
| WO | WO 95/11696 A1 | 5/1995 |
| WO | WO 96/012406 A1 | 2/1996 |
| WO | WO 96/20698 A2 | 7/1996 |
| WO | WO 98/002441 A2 | 1/1998 |
| WO | WO 98/010056 A1 | 12/1998 |
| WO | WO 99/22762 A1 | 5/1999 |
| WO | WO 99/34826 A1 | 7/1999 |
| WO | WO 2001/068133 A1 | 9/2001 |
| WO | WO 2001/091802 A1 | 12/2001 |
| WO | WO 02/09770 A1 | 2/2002 |
| WO | WO 02/32404 A2 | 4/2002 |
| WO | WO 02/088304 A2 | 11/2002 |
| WO | WO 03/033526 A2 | 4/2003 |
| WO | WO 03/094840 A2 | 11/2003 |
| WO | WO 2004/050090 A1 | 6/2004 |
| WO | WO 2005/097116 A1 | 10/2005 |
| WO | WO 2006/041890 A2 | 4/2006 |
| WO | WO 2006/094507 A1 | 9/2006 |
| WO | WO 2007/067683 A2 | 6/2007 |
| WO | WO 2007/087341 A2 | 8/2007 |
| WO | WO 2007/098254 A2 | 8/2007 |
| WO | WO 2007/133835 A2 | 11/2007 |
| WO | WO 2008/036374 A2 | 3/2008 |
| WO | WO 2008/043157 A1 | 4/2008 |
| WO | WO 2008/069942 A2 | 6/2008 |
| WO | WO 2008/073558 A2 | 6/2008 |
| WO | WO 2008/083331 A2 | 7/2008 |
| WO | WO 2008/109163 A1 | 9/2008 |
| WO | WO 2008/150868 A1 | 12/2008 |
| WO | WO 2009/007750 A1 | 1/2009 |
| WO | WO 2009/022154 A2 | 2/2009 |
| WO | WO 2009/039502 A1 | 3/2009 |
| WO | WO 2009/051837 A2 | 4/2009 |
| WO | WO 2009/106999 A2 | 9/2009 |
| WO | WO 2009/131712 A2 | 10/2009 |
| WO | WO 2009/145238 A1 | 12/2009 |
| WO | WO 2010/025324 A2 | 3/2010 |
| WO | WO 2010/027471 A2 | 3/2010 |
| WO | WO 2010/037402 A1 | 4/2010 |
| WO | WO 2010/042863 A1 | 4/2010 |
| WO | WO 2010/042866 | 4/2010 |
| WO | WO 2010/042870 A1 | 4/2010 |
| WO | WO 2010/042876 | 4/2010 |
| WO | WO 2010/047839 A1 | 4/2010 |
| WO | WO 2010/075072 A2 | 7/2010 |
| WO | WO 2010/085509 A1 | 7/2010 |
| WO | WO 2010/089122 A2 | 8/2010 |
| WO | WO 2010/116141 A2 | 10/2010 |
| WO | WO 2010/123569 A2 | 10/2010 |
| WO | WO 2010/125565 A2 | 11/2010 |
| WO | WO 2010/138192 A2 | 12/2010 |
| WO | WO 2010/138193 A2 | 12/2010 |

(56) References Cited

FOREIGN PATENT DOCUMENTS

| WO | WO 2010/138194 | | 12/2010 |
|----|----|----|----|
| WO | WO 2011/033090 | A1 | 3/2011 |
| WO | WO 2011/109833 | A2 | 9/2011 |
| WO | WO 2011/150240 | A1 | 12/2011 |
| WO | WO 2011/156119 | A1 | 12/2011 |
| WO | WO 2012/019041 | A2 | 2/2012 |
| WO | WO 2012/021512 | A2 | 2/2012 |
| WO | WO 2012/054920 | A2 | 4/2012 |
| WO | WO 2012/149247 | A2 | 11/2012 |
| WO | WO 2012/149252 | A2 | 11/2012 |
| WO | WO 2012/149255 | A2 | 11/2012 |
| WO | WO 2012/149259 | A1 | 11/2012 |
| WO | WO 2012/149265 | A2 | 11/2012 |
| WO | WO 2012/149268 | A1 | 11/2012 |
| WO | WO 2012/149405 | A2 | 11/2012 |
| WO | WO 2012/149411 | A1 | 11/2012 |
| WO | WO 2012/158362 | A1 | 11/2012 |
| WO | WO 2013/058812 | A1 | 4/2013 |
| WO | WO 2013/123503 | A1 | 8/2013 |
| WO | WO 2014/145524 | A2 | 9/2014 |
| WO | WO 2014/168953 | A1 | 10/2014 |
| WO | WO 2014/179771 | A1 | 11/2014 |
| WO | WO 2015/138357 | A2 | 9/2015 |
| WO | WO 2015/162594 | A2 | 10/2015 |
| WO | WO 2016/037164 | A1 | 3/2016 |
| WO | WO 2016/073798 | A1 | 5/2016 |
| WO | WO 2017/139212 | A1 | 8/2017 |
| WO | WO 2017/156513 | A1 | 9/2017 |
| WO | WO 2010/018384 | A1 | 2/2018 |
| WO | WO 2018/127382 | A1 | 7/2018 |
| WO | WO 2018/129268 | A1 | 7/2018 |
| WO | WO 2018/169811 | A1 | 9/2018 |
| WO | WO 2019/075360 | A1 | 4/2019 |
| WO | WO 2019/162951 | A1 | 8/2019 |
| WO | WO 2020/223205 | A1 | 11/2020 |
| WO | WO 2020/247625 | A1 | 12/2020 |

OTHER PUBLICATIONS

Aalbers et al., Preclinical Potency and Biodistribution Studies of an AAV 5 Vector Expressing Human Interferon-β (ART-I02) for Local Treatment of Patients with Rheumatoid Arthritis. PLoS One. Jun. 24, 2015;10(6):e0130612. doi:10.1371/journal.pone.0130612. 17 pages.

Abeles, PEG-ing down (and preventing?) the cause of pegloticase failure. Arthritis Res Ther. May 30, 2014;16(3):112. doi: 10.1186/ar4572.

Adorini et al., Tolerogenic dendritic cells induced by vitamin D receptor ligands enhance regulatory T cells inhibiting allograft rejection and autoimmune diseases. J Cell Biochem. Feb. 1, 2003;88(2):227-33.

Alewine et al., Efficacy of RG7787, a next-generation mesothelin-targeted immunotoxin, against triple-negative breast and gastric cancers. Mol Cancer Ther. Nov. 2014;13(11):2653-61. doi: 10.1158/1535-7163.MCT-14-0132. Epub Sep. 19, 2014.

Amu et al., Regulatory B cells prevent and reverse allergic airway inflammation via FoxP3-positive T regulatory cells in a murine model. J Allergy Clin Immunol. 2010;125:1114-24.

Anguela et al., Robust ZFN-mediated genome editing in adult hemophilic mice. Blood. Nov. 7, 2013;122(19):3283-7. doi: 10.1182/blood-2013-04-497354. Epub Oct. 1, 2013.

Aronovich et al., Quantitative analysis of α-L-iduronidase expression in immunocompetent mice treated with the Sleeping Beauty transposon system. PLoS One. Oct. 21, 2013;8(10):e78161. doi: 10.1371/journal.pone.0078161. eCollection 2013.

Arruda et al., Strategies to modulate immune responses: a new frontier for gene therapy. Mol Ther. Sep. 2009;17(9):1492-503. doi: 10.1038/mt.2009.150. Epub Jul. 7, 2009. Review.

Ashe et al., Inhibition of glycogen biosynthesis via mTORC1 suppression as an adjunct therapy for Pompe disease. Mol Genet Metab. Aug. 2010;100(4):309-15. doi: 10.1016/j.ymgme.2010.05.001. Epub May 5, 2010.

Azzi et al., Polylactide-cyclosporin A nanoparticles for targeted immunosuppression. FASEB J. Oct. 2010;24(10):3927-38. doi: 10.1096/fj.10-154690. Epub Jun. 14, 2010.

Bae et al., Vinyl sulfone-terminated PEG-PLLA diblock copolymer for thiol-reactive polymeric micelle. Apr. 9, 2009;42(10):3437-42. Macromolecules.

Baker et al., Immunogenicity of protein therapeutics: The key causes, consequences and challenges. Self Nonself—Immune Recognition and Signaling. Dec. 1, 2010;1(4):314-22.

Barzel et al., Promoterless gene targeting without nucleases ameliorates haemophilia B in mice. Nature. Jan. 15, 2015;517(7534):360-4. doi: 10.1038/nature13864. Epub Jul. 15, 2015. 21 pages.

Battaglia et al., Rapamycin promotes expansion of functional CD4+CD25+FOXP3+ regulatory T cells of both healthy subjects and type 1 diabetic patients. J Immunol. Dec. 15, 2006;177(12):8338-47.

Bawarski et al., Emerging nanopharmaceuticals. Nanomed: Nanotechnol Biol Med. 2008;4:273-82.

Bayle et al., Rapamycin analogs with differential binding specificity permit orthogonal control of protein activity. Chem Biol. Jan. 2006;13(1):99-107.

Beevers et al., Curcumin inhibits the mammalian target of rapamycin-mediated signaling pathways in cancer cells. Int J Cancer. Aug. 15, 2006; 119(4):757-64.

Berhanu et al., Pegloticase failure and a possible solution: Immunosuppression to prevent intolerance and inefficacy in patients with gout. Semin Arthritis Rheum. Jun. 2017;46(6):754-758. doi: 10.1016/j.semarthrit.2016.09.007. Epub Sep. 20, 2016.

Bi et al., High-efficiency targeted editing of large viral genomes by RNA-guided nucleases. PLoS Pathog. May 1, 2014;10(5):e1004090. doi: 10.1371/journal.ppat.1004090. eCollection May 2014.

Binder et al., Tumor necrosis factor-inhibiting therapy preferentially targets bone destruction but not synovial inflammation in a tumor necrosis factor-driven model of rheumatoid arthritis. Arthritis Rheum. Mar. 2013;65(3):608-17. doi: 10.1002/art.37797.

Bisset et al., Therapeutic impact of systemic AAV-mediated RNA interference in a mouse model of myotonic dystrophy. Hum Mol Genet. Sep. 1, 2015;24(17):4971-83. doi: 10.1093/hmg/ddv219. Epub Jun. 16, 2015.

Bocian et al., Rapamycin, unlike cyclosporine A, enhances suppressive functions of in vitro-induced CD4+CD25+ Tregs. Nephrol Dial Transplant. Mar. 2010;25(3):710-7. doi: 10.1093/ndt/gfp586. Epub Nov. 9, 2009.

Boden et al., Regulatory T cells in inflammatory bowel disease. Curr Opin Gastroenterol. Nov. 2008;24(6):733-41.

Bouaziz et al., Regulatory B cells as inhibitors of immune responses and inflammation. Immunol Rev. Aug. 2008;224:201-14. doi: 10.1111/j.1600-065X.2008.00661.x. Review.

Brown et al., Endogenous microRNA regulation suppresses transgene expression in hematopoietic lineages and enables stable gene transfer. Nat Med. May 2006;12(5):585-91. Epub Apr. 23, 2006.

Bryant et al., Nanoparticle delivery of donor antigens for transplant tolerance in allogeneic islet transplantation. Biomaterials. Oct. 2014;35(31):8887-94. doi: 10.1016/j.biomaterials.2014.06.044.

Caccamo et al., Rapamycin rescues TDP-43 mislocalization and the associated low molecular mass neurofilament instability. J Biol Chem. Oct. 2, 2009;284(40):27416-24. doi: 10.1074/jbc.M109.031278. Epub Aug. 3, 2009.

Cappellano et al., Subcutaneous inverse vaccination with PLGA particles loaded with a MOG peptide and IL-10 decreases the severity of experimental autoimmune encephalomyelitis. Vaccine. Aug. 20, 2014. pii: S0264-410X(14)01129-3. doi: 10.1016/j.vaccine.2014.08.016. 9 pages.

Carpentier et al., Effect of alipogene tiparvovec (AAV1-LPL(S447X)) on postprandial chylomicron metabolism in lipoprotein lipase-deficient patients. J Clin Endocrinol Metab. May 2012;97(5):1635-44. doi: 10.1210/jc.2011-3002. Epub Mar. 21, 2012.

Chandler et al., Liver-directed adeno-associated virus serotype 8 gene transfer rescues a lethal murine model of citrullinemia type 1. Gene Ther. Dec. 2013;20(12):1188-91. doi: 10.1038/gt.2013.53. Epub Oct. 17, 2013.

(56) References Cited

OTHER PUBLICATIONS

Chen et al., Targeting transgene to the heart and liver with AAV9 by different promoters. Clin Exp Pharmacol Physiol. Oct. 2015;42(10):1108-17. doi: 10.1111/1440-1681.12453. Original Article. 24 pages.
Cheng et al., Efficient gene editing in adult mouse livers via adenoviral delivery of CRISPR/Cas9. FEBS Lett. Nov. 3, 2014;588(21):3954-8. doi: 10.1016/j.febslet.2014.09.008. Epub Sep. 19, 2014.
Colman et al., Effects of amino acid sequence changes on antibody-antigen interactions. Res Immunol. Jan. 1994;145(1):33-6.
Comas et al., New nanoformulation of rapamycin Rapatar extends lifespan in homozygous p53-/- mice by delaying carcinogenesis. Aging (Albany NY). Oct. 2012;4(10):715-22.
Coombes et al., A functionally specialized population of mucosal CD103+ DCs induces Foxp3+ regulatory T cells via a TGF-beta and retinoic acid-dependent mechanism. J Exp Med. Aug. 6, 2007;204(8): 1757-64. Epub Jul. 9, 2007.
Corti et al., B-Cell Depletion is Protective Against Anti-AAV Capsid Immune Response: A Human Subject Case Study. Mol Ther Methods Clin Dev. 2014;1. pii: 14033. 7 pages.
Crittenden et al., New therapies for gout. Annu Rev Med. 2013;64:325-37. doi: 10.1146/annurev-med-080911-105830.
Cvetanovich et al., Human regulatory T cells in autoimmune diseases. Curr Opin Immunol. Dec. 2010;22(6):753-60. Epub Sep. 24, 2010.
Dai et al., Cellular and humoral immune responses to adenoviral vectors containing factor IX gene: tolerization of factor IX and vector antigens allows for long-term expression. Proc Natl Acad Sci USA. Feb. 28, 1995;92(5):1401-5.
Das et al., Delivery of rapamycin-loaded nanoparticle down regulates ICAM-1 expression and maintains an immunosuppressive profile in human CD34+ progenitor-derived dendritic cells. J Biomed Mater Res A. Jun. 15, 2008;85(4):983-92.
Davila et al., Cell-based immunotherapy with suppressor CD8+ T cells in rheumatoid arthritis. J Immunol. Jun. 1, 2005;174(11):7292-301.
De Sabbata et al., Development of a novel AAV vector in combination with tolerogenic nanoparticles for the treatment of ornithine transcarbamylase deficiency. Human Gene Ther. 2017; 28(12): A71. Abstract P197.
Delgoffe et al., The mTOR kinase differentially regulates effector and regulatory T cell lineage commitment. Immunity. Jun. 1, 20099;30(6):832-44. doi: 10.1016/j.immuni.2009.04.014.
Denti et al., Body-wide gene therapy of Duchenne muscular dystrophy in the mdx mouse model. Proc Natl Acad Sci USA. Mar. 7, 2006;103(10):3758-63. Epub Feb. 24, 2006.
Dilillo et al., B10 cells and regulatory B cells balance immune responses during inflammation, autoimmunity, and cancer. Ann N Y Acad Sci. Jan. 2010;1183:38-57. doi: 10.1111/j.1749-6632.2009. 05137.x. Review.
Dinarvand et al., Polylactide-co-glycolide nanoparticles for controlled delivery of anticancer agents. Int J Nanomedicine. 2011;6:877-95. doi: 10.2147/IJN.S18905. Epub May 27, 2011.
Dinesh et al., CD8+ Tregs in lupus, autoimmunity, and beyond. Autoimmun Rev. Jun. 2010;9(8):560-8. doi: 10.1016/j.autrev.2010. 03.006. Epub Jun. 1, 2011. 21 pages.
Dobrolovskaja et al., Immunological properties of engineered nonomaterials. Nat Nanotechnol. Aug. 2007;2(8):469-78. Review.
Düchs, Dissertation entitled: Effects of Toll-like receptor agonists on the pathogenesis of atopic asthma in mice, University of Würzburg, Sep. 2011. 147 pages.
Dupont et al., The evolving role of sirolimus in renal transplantation. QJM. Jun. 2003;96(6):401-9. Review.
Eghtesad et al., Effect of rapamycin on immunity induced by vector-mediated dystrophin expression in mdx skeletal muscle. Sci Rep. 2012;2:399. doi: 10.1038/srep00399. Epub May 8, 2012. 6 pages.

Endharti et al., Cutting edge: CD8+CD122+ regulatory T cells produce IL-10 to suppress IFN-gamma production and proliferation of CD8+ T cells. J Immunol. Dec. 1, 2005;175(11):7093-7.
Esposito et al., Rapamycin inhibits relapsing experimental autoimmune encephalomyelitis by both effector and regulatory T cells modulation. J Neuroimmunol. Mar. 30, 2010;220(1-2):52-63. doi: 10.1016/j.jneuroim.2010.01.001. Epub Feb. 11, 2010.
Falk et al., Induction and suppression of an autoimmune disease by oligomerized T cell epitopes: enhanced in vivo potency of encephalitogenic peptides. J Exp Med. Feb. 21, 2000;191(4):717-30.
Fasier et al., Antagonistic peptides specifically inhibit proliferation, cytokine production, CD40L expression, and help for IgE synthesis by Der p 1-speciftc human T-cell clones. J Allergy Clin Immunol. Apr. 1998;101(4 Pt 1):521-30.
Faunce et al., Cutting edge: in vitro-generated tolerogenic APC induce CD8+ T regulatory cells that can suppress ongoing experimental autoimmune encephalomyelitis. J Immunol. Feb. 15, 2004;172(4):1991-5.
Fifis et al., Size-dependent immunogenicity: therapeutic and protective properties of nano-vaccines against tumors. J Immunol. Sep. 1, 2004;173(5):3148-54.
Fiorino et al., A single cohort, dose escalation phase 1 study of intravenous infusion of pegsiticase (formerly Uricase-PEG 20), a drug for managing hyperuricemia in refractory gout [Abstract]. Abstracts of the American College of Rheumatology/Association of Rheumatology Health Professionals Annual Scientific Meeting. Atlanta, Georgia. Nov. 6-11, 2010. Arthritis Rheum. Nov. 2010;62 Suppl 10: 144. DOI: 10.1002/art.27913. 2 pages.
Fischer et al., Rapamycin-conditioned, alloantigen-pulsed myeloid dendritic cells present donor MHC class I/peptide via the semi-direct pathway and inhibit survival of antigen-specific CD8(+) T cells in vitro and in vivo. Transpl Immunol. Jul. 2011;25(1):20-6. Epub May 10, 2011.
Fourtounas et al., Different immunosuppressive combinations on T-cell regulation in renal transplant recipients. Am J Nephrol. 2010;32(1):1-9. doi: 10.1159/000313940. Epub May 20, 2010.
Fraser et al., Nanoparticle therapy for allergic and inflammatory disease. Anti-Inflammatory & Anti-Allergy Agents Med Chem. Mar. 2010;9(1):54-70.
Gajofatto et al., Treatment strategies for multiple sclerosis: When to start, when to change, when to stop? World J Clin Cases. Jul. 16, 2015;3(7):545-55. doi: 10.12998/wjcc.v3.i7.545.
Gao et al., Contrasting effects of cyclosporine and rapamycin in de novo generation of alloantigen-specific regulatory T cells. Am J Transplant. Jul. 2007;7(7):1722-32. Epub May 19, 2007.
Garay et al., Therapeutic perspectives on uricases for gout. Joint Bone Spine. May 2012;79(3):237-42. doi: 10.1016/j.jbspin.2012. 01.004. Epub Feb. 25, 2012. Review.
Garcia et al., CCR9+ and CD 103+ tolerogenic dendritic cell populations in food allergy patients undergoing oral immunotherapy. Clin Transl Allergy. 2011; l(Suppl 1): O51.
Getts et al., Harnessing nanoparticles for immune modulation. Trends Immunol. Jul. 2015;36(7):419-27.
Goyenvalle et al., Engineering multiple U7snRNA constructs to induce single and multiexon-skipping for Duchenne muscular dystrophy. Mol Ther. Jun. 2012;20(6):1212-21. doi: 10.1038/mt.2012.26. Epub Feb. 21, 2012.
Goyenvalle et al., Rescue of dystrophic muscle through U7 snRNA-mediated exon skipping. Science. Dec. 3, 2004;306(5702):1796-9. Epub Nov. 4, 2004.
Gray et al., Apoptotic cells protect mice from autoimmune inflammation by the induction of regulatory B cells. Proc Natl Acad Sci U S A. Aug. 28, 2007;104(35):14080-5. Epub Aug. 21, 2007.
Gray et al., What are regulatory B cells? Eur J Immunol. Oct. 2010;40(10):2677-9.
Haddadi et al., Delivery of rapamycin by PLGA nanoparticles enhances its suppressive activity on dendritic cells. J Biomed Mater Res A. Mar. 15, 2008;84(4):885-98.
Hahn et al., Cellular and molecular mechanisms of regulation of autoantibody production in lupus. Ann N Y Acad Sci. Jun. 2005;1051:433-41. Review. Epub Apr. 10, 2008. 9 pages.

(56) References Cited

OTHER PUBLICATIONS

Hahn et al., Tolerogenic treatment of lupus mice with consensus peptide induces Foxp3-expressing, apoptosis-resistant, TGFbeta-secreting CD8+ T cell suppressors. J Immunol. Dec. 1, 2005;175(11):7728-37.
Hamdy et al., Co-delivery of cancer-associated antigen and Toll-like receptor 4 ligand in PLGA nanoparticles induces potent CD8+ T cell-mediated anti-tumor immunity. Vaccine. Sep. 15, 2008;26(39):5046-57. doi: 10.1016/j.vaccine.2008.07.035. Epub Aug. 3, 2008.
Hamdy et al., Part I: targeted particles for cancer immunotherapy. Curr Drug Deliv. May 2011;8(3):261-73.
Hamdy et al., Targeting dendritic cells with nano-particulate PLGA cancer vaccine formulations. Adv Drug Deliv Rev. Sep. 10, 2011;63(10-11):943-55. doi:10.1016/j.addr.2011.05.021. Epub Jun. 6, 2011. Review.
Hamdy et al., The immunosuppressive activity of polymeric micellar formulation of cyclosporine A: in vitro and in vivo studies. AAPS J. Jun. 2011;13(2):159-68. doi: 10.1208/S12248-011-9259-8. Epub Feb. 19, 2011.
Händel et al., Versatile and efficient genome editing in human cells by combining zinc-finger nucleases with adeno-associated viral vectors. HumGene Ther. Mar. 2012;23(3):321-9. doi: 10.1089/hum.2011.140. Epub Dec. 14, 2011.
Hashimoto et al., Stimulation of host NKT cells by synthetic glycolipid regulates acute graft-versus-host disease by inducing Th2 polarization of donor T cells. J Immunol. Jan. 1, 2005;174(1):551-6.
Hassan et al., Major cancer regressions in mesothelioma after treatment with an anti-mesothelin immunotoxin and immune suppression. Sci Transl Med. Oct. 23, 2013;5(208):208ra147. doi: 10.1126/scitranslmed.3006941.
Heidt et al., Effects of immunosuppressive drugs on purified human B cells: evidence supporting the use of MMF and rapamycin. Transplantation. Nov. 2008;86(9):1292-1300. doi: 10.1097/TP.0b013e3181874a36.
Hershfield et al., Induced and pre-existing anti-polyethylene glycol antibody in a trial of every 3-week dosing of pegloticase for refractory gout, including in organ transplant recipients. Arthritis Res Ther. Mar. 7, 2014;16(2):R63. doi: 10.1186/ar4500.
Horibe et al., Rapamycin-conditioned, alloantigen-pulsed dendritic cells promote indefinite survival of vascularized skin allografts in association with T regulatory cell expansion. Transplant Immunol. Feb. 2008;18(4):307-318. doi: 10.1016/j.trim.2007.10.007.
Hui et al., Modulation of CD8+ T cell responses to AAV vectors with IgG-derived MHC class II epitopes. Mol Ther. Sep. 2013;21(9):1727-37. doi: 10.1038/mt.2013.166. Epub Jul. 16, 2013.
Hushmendy et al., Select phytochemicals suppress human T-lymphocytes and mouse splenocytes suggesting their use in autoimmunity and transplantation. Nutr Res. Aug. 2009;29(8):568-78. doi: 10.1016/j.nutres.2009.08.003. PubMed PMID: 19761891.
Imamura et al., Pravastatin attenuates allergic airway inflammation by suppressing antigen sensitisation, interleukin 17 production and antigen presentation in the lung. Thorax. Jan. 2009;64(1):44-9. doi: 10.1136/thx.2007.094540. Epub Oct. 3, 2008.
Ishii, [Allergen-specific immunotherapy utilizing mechanisms for immune regulation]. Nihon Rinsho Meneki Gakkai Kaishi. Oct. 2008;31(5):392-8. Review.
Ito et al., A convenient enzyme-linked immunosorbent assay for rapid screening of anti-adeno-associated virus neutralizing antibodies. Ann Clin Biochem. Nov. 2009;46(Pt 6):508-10. doi: 10.1258/acb.2009.009077. Epub Sep. 3, 2009.
Jhunjhunwala et al., Delivery of rapamycin to dendritic cells using degradable microparticles. J Control Release. Feb. 10, 2009;133(3):191-7. doi: 10.1016/j.jconrel.2008.10.011. Epub Oct. 26, 2008.
Jiang et al., Effects of transient immunosuppression on adenoassociated, virus-mediated, liver-directed gene transfer in rhesus macaques and implications for human gene therapy. Blood. Nov. 15, 2006;108(10):3321-8. Epub Jul. 25, 2006.
Jones, Critically assessing the state-of-the-art in protein structure prediction. Pharmacogenomics J. 2001; 1(2):126-34. Review.
Kang et al., Very low-dose tolerance with nucleosomal peptides controls lupus and induces potent regulatory T cell subsets. J Immunol. Mar. 15, 2005;174(6):3247-55.
Kaplan et al., Transient immunosuppression with deoxyspergualin improves longevity of transgene expression and ability to readminister adenoviral vector to the mouse lung. Hum Gene Ther. Jun. 10, 1997;8(9):1095-104.
Karamloo et al., Prevention of allergy by a recombinant multi-allergen vaccine with reduced IgE binding and preserved T cell epitopes. Eur J Immunol. Nov. 2005;35(11):3268-76.
Keselowsky et al., Multifunctional dendritic cell-targeting polymeric microparticles: engineering new vaccines for type 1 diabetes. Hum Vaccin. Jan. 1, 2011;7(1):37-44. Epub Jan. 1, 2011. Review.
Kim et al., Effects of cyclosporine and rapamycin on immunoglobulin production by preactivated human B cells. Clin Exp Immunol. Jun. 1994;96(3):508-12.
Kim et al., Inhibition of follicular T-helper cells by CD8(+) regulatory T cells is essential for self. Nature. Sep. 16, 2010;467(7313):328-32.
Kim et al., Simvastatin induces Foxp3+ T regulatory cells by modulation of transforming growth factor-beta signal transduction. Immunology. Aug. 2010;130(4):484-93. doi: 10.1111/j.1365-2567.2010.03269.x. Epub Apr. 12, 2010.
Kingsley et al., Transplantation tolerance: lessons from experimental rodent models. Transpl Int. Oct. 2007;20(10):828-41. Epub Aug. 17, 2007.
Kishimoto et al., Improving the efficacy and safety of biologic drugs with tolerogenic nanoparticles. Nat Nanotechnol. Oct. 2016;11(10):890-899. doi: 10.1038/nnano.2016.135. Epub Aug. 1, 2016.
Konya et al., Treating autoimmune disease by targeting CD8(+) T suppressor cells. Expert Opin Biol Ther. Aug. 2009;9(8):951-65. doi: 10.1517/14712590903020759. Review. Epub Aug. 1, 2010. 22 pages.
Kunisawa et al., Fusogenic liposome functions as an efficient immunoadjuvant in inducing humoral immune-responses to soluble antigen. Drug Delivery System. Jan. 1998;13(1):21-26.
Lassmann et al., The molecular basis of neurodegeneration in multiple sclerosis. FEBS Lett. Dec. 1, 2011;585(23):3715-23. doi: 10.1016/j.febslet.2011.08.004. Epub Aug. 16, 2011.
Le Hir et al., AAV genome loss from dystrophic mouse muscles during AAV-U7 snRNA-mediated exon-skipping therapy. Mol Ther. Aug. 2013;21(8):1551-8. doi: 10.1038/mt.2013.121. Epub Jun. 11, 2013.
Lipsky et al., Pegloticase immunogenicity: the relationship between efficacy and antibody development in patients treated for refractory chronic gout. Arthritis Res Ther. Mar. 4, 2014;16(2):R60. doi: 10.1186/ar4497.
Louis Jeune et al., Pre-existing anti-adeno-associated virus antibodies as a challenge in AAV gene therapy. Hum Gene Ther Methods. Apr. 2013;24(2):59-67. doi: 10.1089/hgtb.2012.243. Epub Apr. 3, 2013. Review.
Lowenstein, The case for immunosuppression in clinical gene transfer. Mol Ther. Aug. 2005;12(2):185-6.
Lu et al., Rapamycin promotes the expansion of CD4(+) Foxp3(+) regulatory T cells after liver transplantation. Transplant Proc. Jun. 2010;42(5):1755-7. doi: 10.1016/j.transproceed.2009.10.008.
Lu et al., The regulation of immune tolerance by FOXP3. Nat Rev Immunol. Nov. 2017;17(11):703-717. doi: 10.1038/nri.2017.75. Epub Jul. 31, 2017. Review.
Lutsiak et al., Analysis of poly(D,L-lactic-co-glycolic acid) nanosphere uptake by human dendritic cells and macrophages in vitro. Pharm Res. Oct. 2002;19(10):1480-7.
Macary et al., Ovalbumin-specific, MHC class I-restricted, alpha beta-positive, Tc1 and Tc0 CD8+ T cell clones mediate the in vivo inhibition of rat IgE. J Immunol. Jan. 15, 1998;160(2):580-7.
Maher et al., Targeting cytotoxic T lymphocytes for cancer immunotherapy. Br J Cancer. Aug. 31, 2004;91(5):817-21. Review.
Maldonado et al., How tolerogenic dendritic cells induce regulatory T cells. Adv Immunol. 2010;108:111-65. doi: 10.1016/B978-0-12-380995-7.00004-5. Review.
Maldonado et al., Polymeric synthetic nanoparticles for the induction of antigen-specific immunological tolerance. Proc Natl Acad

(56) References Cited

OTHER PUBLICATIONS

Sci U S A. Jan. 13, 2015;112(2):E156-65. doi: 10.1073/pnas. 1408686111. Epub Dec. 29, 2014.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592.

Martino et al., Engineered AAV vector minimizes in vivo targeting of transduced hepatocytes by capsid-specific CD8+ T cells. Blood. Mar. 21, 2013;121(12):2224-33. doi: 10.1182/blood-2012-10-460733. Epub Jan. 16, 2013.

Mason, Functional Analysis of the Cysteine Residues of Activin A. Mol Endocrinol. 1994;8(3):325-32.

Matsui et al., Delivery of full-length factor VIII using a piggyBac transposon vector to correct a mouse model of hemophilia A. PLoS One. Aug. 15, 2014;9(8):e104957. doi:10.1371/journal.pone. 0104957. eCollection 2014.

Mazor et al., Immunogenicity of therapeutic recombinant immunotoxins. Immunol Rev. Mar. 2016;270(1):152-64. doi: 10.1111/imr.12390. Review.

McFarland et al., Ovalbumin(323-339) peptide binds to the major histocompatibility complex class II I-A(d) protein using two functionally distinct registers. Biochemistry. Dec. 14, 1999;38(50):16663-70.

McKay et al., A novel anti-inflammatory role of simvastatin in a murine model of allergic asthma. J Immunol. Mar. 1, 2004;172(5):2903-8.

McMahon et al., Epitope spreading initiates in the CNS in two mouse models of multiple sclerosis. Nat Med. Mar. 2005;11(3):335-9. Epub Feb. 27, 2005.

Meliani et al., Determination of anti-adeno-associated virus vector neutralizing antibody titer with an in vitro reporter system. Hum Gene Ther Methods. Apr. 2015;26(2):45-53. doi: 10.1089/hgtb.2015. 037.

Menzies et al., Simvastatin does not exhibit therapeutic anti-inflammatory effects in asthma. J Allergy Clin Immunol. Feb. 2007;119(2):328-35. Epub Dec. 4, 2006.

Mine et al., Epitope characterization of ovalbumin in BALB/c mice using different entry routes. Biochim Biophys Acta. Feb. 2007;1774(2):200-12. Epub Dec. 19, 2006.

Mingozzi et al., Modulation of tolerance to the transgene product in a nonhuman primate model of AAV-mediated gene transfer to liver. Blood. Oct. 1, 2007;110(7):2334-41. Epub Jul. 3, 2007.

Miyara et al., Therapeutic approaches to allergy and autoimmunity based on FoxP3+ regulatory T-cell activation and expansion. J Allergy Clin Immunol. Apr. 2009;123(4):749-55.

Moghimi et al., Induction of tolerance to factor VIII by transient co-administration with rapamycin. J Thromb Haemost. Aug. 2011;9(8):1524-33. doi: 10.1111/j.1538-7836.2011.04351.x.

Moraes-Fontes et al., Steroid treatments in mice do not alter the number and function of regulatory T cells, but amplify cyclophosphamide-induced autoimmune disease. J Autoimmun. Sep. 2009;33(2):109-20. doi: 10.1016/j.jaut.2009.03.008. Epub Apr. 11, 2009.

Mottram et al., Type 1 and 2 immunity following vaccination is influenced by nanoparticle size: formulation of a model vaccine for respiratory syncytial virus. Mol Pharm. Jan.-Feb. 2007;4(1):73-84.

Nathwani et al., Adenovirus-associated virus vector-mediated gene transfer in hemophilia B. N Engl J Med. Dec. 22, 2011;365(25):2357-65. doi: 10.1056/NEJMoa1108046. Epub Dec. 10, 2011.

Nathwani et al., Long-term safety and efficacy of factor IX gene therapy in hemophilia B. N Engl J Med. Nov. 20, 2014;371(21):1994-2004. doi: 10.1056/NEJMoa1407309. Epub May 20, 2015. 17 pages.

Nathwani et al., Self-complementary adeno-associated virus vectors containing a novel liverspecific human factor IX expression cassette enable highly efficient transduction of murine and nonhuman primate liver. Blood. Apr. 1, 2006;107(7):2653-61. doi: 10.1182/blood2005104035. Epub Dec. 1, 2005.

Nayak et al., Prevention and Reversal of Antibody Responses Against Factor IX in Gene Therapy for Hemophilia B. Front Microbiol. Dec. 7, 2011;2:244. doi: 10.3389/fmicb.2011.00244. eCollection 2011.

Nayak et al., Prophylactic immune tolerance induced by changing the ratio of antigen-specific effector to regulatory T cells. J Thromb Haemost. Sep. 2009;7(9):1523-32. doi: 10.1111/j.1538-7836.2009. 03548.x. Epub Jul. 6, 2009.

Neuhaus et al., mTOR inhibitors: an overview. Liver Transpl. Jun. 2001;7(6):473-84.

Ngo et al., In The Protein Folding Problem and Tertiary Structure Prediction, 1994. Eds Mertz et al. Birkhauser. Boston, MA. 1994:433,491-5.

Oh et al., CD4+CD25+ regulatory T cells in autoimmune arthritis. Immunol Rev. Jan. 2010;233(1):97-111.

Oh et al., Foxp3-independent mechanism by which TGF-β controls peripheral T cell tolerance. Proc Natl Acad Sci U S A. Sep. 5, 2017;114(36):E7536-E7544. doi: 10.1073/pnas.1706356114. Epub Aug. 21, 2017.

Oleinika et al., Suppression, subversion and escape: the role of regulatory T cells in cancer progression. Clin Exp Immunol. Jan. 2013;171(1):36-45. doi: 10.1111/j.1365-2249.2012.04657.x. Review.

Omata et al., Ovalbumin-specific IgE modulates ovalbumin-specific T-cell response after repetitive oral antigen administration. J Allergy Clin Immunol. Apr. 2005;115(4):822-7.

Onda et al., Tofacitinib suppresses antibody responses to protein therapeutics in murine hosts. J Immunol. Jul. 1, 2014;193(1):48-55. doi: 10.4049/jimmunol.1400063. Epub Jun. 2, 2014.

"Pluronic."Oxford Dictionary entry accessed via www.oxforddictionary. com on May 6, 2016. 8 pages.

Paolicelli et al., Surface-modified PLGA-based nanoparticles that can efficiently associate and deliver virus-like particles. Nanomedicine (Lond). Aug. 2010;5(6):843-53.

Papisov, Acyclic polyacetals from polysaccharides: biomimetic biomedical "stealth" polymers. Chapter 19. ACS Symposium Series. Feb. 15, 2001:786:301-14.

Pastan et al., Immunotoxin therapy of cancer. Nat Rev Cancer. Jul. 2006;6(7):559-65. Review.

Perez-Ruiz et al., Lesinurad in combination with allopurinol: results of a phase 2, randomised, double-blind study in patients with gout with an inadequate response to allopurinol. Ann Rheum Dis. Jun. 2016;75(6):1074-80. doi: 10.1136/annrheumdis-2015-207919. Epub Jan. 7, 2016.

Platt et al., CRISPR-Cas9 knockin mice for genome editing and cancer modeling. Cell. Oct. 9, 2014;159(2):440-55. doi: 10.1016/j. cell.2014.09.014. Epub Sep. 25, 2014.

Post et al., Adenoviral PR39 improves blood flow and myocardial function in a pig model of chronic myocardial ischemia by enhancing collateral formation. Am J Physiol Regul Integr Comp Physiol. Mar. 2006;290(3):R494-500. Epub Oct. 27, 2005.

Quarcoo et al., Resiquimod, a new immune response modifier from the family of imidazoquinolinamines, inhibits allergen-induced Th2 responses, airway inflammation and airway hyper-reactivity in mice. Clin Exp Allergy. Aug. 2004;34(8):1314-20.

Ran et al., In vivo genome editing using Staphylococcus aureus Cas9. Nature. Apr. 9, 2015;520(7546):186-91. doi: 10.1038/nature14299. Epub Apr. 1, 2015.

Reddy et al., Detection of autoreactive myelin proteolipid protein 139-151-specific T cells by using MHC II (IAs) tetramers. J Immunol. Jan. 15, 2003;170(2):870-7.

Reichardt et al., Impact of Mammalian Target of Rapamycin Inhibition on Lymphoid Homing and Tolerogenic Function of Nanoparticle-Labeled Dendritic Cells following Allogeneic Hematopoietic Cell Transplantation. J Immunol. 2008;181:4770-9.

Reinders et al., New advances in the treatment of gout: review of pegloticase. Ther Clin Risk Manag. Oct. 27, 2010;6:543-50. doi: 10.2147/TCRM.S6043.

Renz et al., Comparison of the allergenicity of ovalbumin and ovalbumin peptide 323-339. Differential expansion of V beta-expressing T cell populations. J Immunol. Dec. 15, 1993;151(12):7206-13.

(56) References Cited

OTHER PUBLICATIONS

Rice-Ficht et al., Polymeric particles in vaccine delivery. Curr Opin Microbiol. Feb. 2010;13(1):106-12. doi: 10.1016/j.mib.2009.12.001. Epub Jan. 14, 2010. Review.

Rizvi et al., Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. Mar. 2015;16(3):257-65. doi: 10.1016/S1470-2045(15)70054-9. Epub Feb. 20, 2015.

Rybak-Smith et al., Complement activation by carbon nanotubes. Adv Drug Deliv Rev. Sep. 16, 2011;63(12):1031-41. doi: 10.1016/j.addr.2011.05.012. Epub Jun. 12, 2011. Review.

Samuel et al., Nanoparticle delivery systems for control of immunity. Proceedings of the 2004 Intl. Conference on MEMS, NANO and Smart Systems (ICMENS '04). IEEE 2004. 3 pages.

Samuel et al., Polymeric nanoparticles for targeted delivery of Therapeutic Vaccines to dendritic cells. Proceedings of the International Conference on MEMS, NANO and Smart Systems. (ICMENS '03). IEEE 2003. 5 pages.

Sato et al., Induction of immuno tolerance by the application of chase-sulzberger effect. JP J Translpant. 1995;30(3):231-9.

Sato et al., Prolongation of the immunosuppression by repeated injections of donor antigen via the portal vein. JP J Transplant. 1995;30(2):149-54.

Sbiera et al., Influence of short-term glucocorticoid therapy on regulatory T cells in vivo. PLoS One. 2011;6(9):e24345. doi: 10.1371/journal.pone.0024345. Epub Sep. 2, 2011.

Schmidt et al., CRISPR genome engineering and viral gene delivery: a case of mutual attraction. Biotechnol J. Feb. 2015;10(2):258-72. doi: 10.1002/biot.201400529. Epub Feb. 6, 2015.

Seffernick et al., Melamine deaminase and atrazine chlorohydrolase: 98 percent identical but functionally different. J Bacteriol. Apr. 2001;183(8):2405-10.

Senís et al., CRISPR/Cas9-mediated genome engineering: an adeno-associated viral (AAV) vector toolbox. Biotechnol J. Nov. 2014;9(11):1402-12. doi: 10.1002/biot.201400046. Epub Oct. 6, 2014. Supporting Information. 26 pages.

Sharabi et al., The suppression of murine lupus by a tolerogenic peptide involves foxp3-expressing CD8 cells that are required for the optimal induction and function of foxp3-expressing CD4 cells. J Immunol. Sep. 1, 2008;181(5):3243-51.

Shen et al., Combined effect of cyclosporine and sirolimus on improving the longevity of recombinant adenovirus-mediated transgene expression in the retina. Arch Ophthalmol. Jul. 2001;119(7):1033-43.

Shimizu et al., Direct anti-inflammatory mechanisms contribute to attenuation of experimental allograft arteriosclerosis by statins. Circulation. Oct. 28, 2003;108(17):2113-20. Epub Sep. 29, 2003.

Skolnick et al., From genes to protein structure and function: novel applications of computational approaches in the genomic era. Trends Biotechnol. Jan. 2000;18(1):34-9. Review.

Soroosh et al., Th9 and allergic disease. Immunology. Aug. 2009;127(4):450-8. doi: 10.1111/j.1365-2567.2009.03114.x.

Stanek et al., Silencing mutant huntingtin by adeno-associated virus-mediated RNA interference ameliorates disease manifestations in the YAC128 mouse model of Huntington's disease. Hum Gene Ther. May 2014;25(5):461-74. doi: 10.1089/hum.2013.200. Epub Mar. 21, 2014.

Stepkowski et al., Inhibition of host-versus-graft and graft-versus-host responses after small bowel transplantation in rats by rapamycin. Transplantation. Feb. 1992;53(2):258-64.

Sundy et al., Efficacy and tolerability of pegloticase for the treatment of chronic gout in patients refractory to conventional treatment: two randomized controlled trials. JAMA. Aug. 17, 2011;306(7):711-20. doi: 10.1001/jama.2011.1169. PubMed PMID: 21846852.

Sundy et al., Pharmacokinetics and pharmacodynamics of intravenous PEGylated recombinant mammalian urate oxidase in patients with refractory gout. Arthritis Rheum. Mar. 2007;56(3):1021-8. Erratum in: Arthritis Rheum. Apr. 2007;56(4):1370. PubMed PMID: 17328081.

Sundy et al., Reduction of plasma urate levels following treatment with multiple doses of pegloticase (polyethylene glycol-conjugated uricase) in patients with treatment-failure gout: results of a phase II randomized study. Arthritis Rheum. Sep. 2008;58(9):2882-91. doi: 10.1002/art.23810.

Suzuki et al., Inhibitory CD8+ T cells in Autoimmune Disease. Hum Immunol. Nov. 2008;69(11):781-9. doi:10.1016/j.humimm.2008.08.283. Epub Nov. 1, 2009.

Tai et al., A novel rapamycin-polymer conjugate based on a new poly(ethylene glycol) multiblock copolymer. PharmRes. Mar. 2014;31(3):706-19. doi: 10.1007/s11095-013-1192-3. Epub Sep. 26, 2013.

Tardieu et al., Intracerebral administration of adeno-associated viral vector serotype rh.10 carrying human SGSH and SUMF1 cDNAs in children with mucopolysaccharidosis type IIIA disease: results of a phase I/II trial. Hum Gene Ther. Jun. 2014;25(6):506-16. doi: 10.1089/hum.2013.238. Epub May 5, 2014.

Tarzi et al., Peptide immunotherapy for allergic disease. Expert Opin Biol Ther. Jul. 2003;3(4):617-26. Review.

Thomson et al., Immunoregulatory functions of mTOR inhibition. Nat Rev Immunol. May 2009;9(5):324-37. doi: 10.1038/nri2546.

Tosatto et al., Large-scale prediction of protein structure and function from sequence. Curr Pharm Des. 2006;12(17):2067-86. Review.

Tuohy, Peptide determinants of myelin proteolipid protein (PLP) in autoimmune demyelinating disease: a review. Neurochem Res. Aug. 1994;19(8):935-44.

Turnquist et al., Rapamycin-conditioned dendritic cells are poor stimulators of allogeneic CD4+ T cells, but enrich for antigen-specific Foxp3+ T regulatory cells and promote organ transplant tolerance. J Immunol. Jun. 1, 2007;178(11):7018-31.

Ulivieri et al., Simvastatin impairs humoral and cell-mediated immunity in mice by inhibiting lymphocyte homing, T-cell activation and antigen cross-presentation. Eur J Immunol. Oct. 2008;38(10):2832-44. doi: 10.1002/eji.200838278.

Vila et al., Regulatory T cells and autoimmunity. Curr Opin Hematol. Jul. 2009;16(4):274-9.

Vogt et al., Urate oxidase (rasburicase) for treatment of severe tophaceous gout. Nephrol Dial Transplant. Feb. 2005;20(2):431-3.

Wang et al., A systematic assessment of MHC class II peptide binding predictions and evaluation of a consensus approach. PLoS Comput Biol. Apr. 4, 2008;4(4):e1000048. doi: 10.1371/journal.pcbi.1000048.

Wang et al., Sustained AAV-mediated dystrophin expression in a canine model of Duchenne muscular dystrophy with a brief course of immunosuppression. Mol Ther. Jun. 2007;15(6):1160-6. Epub Apr. 10, 2007.

Weber et al., AAV-mediated delivery of zinc finger nucleases targeting hepatitis B virus inhibits active replication. PLoS One. May 14, 2014;9(5):e97579. doi: 10.1371/journal.pone.0097579. eCollection 2014. 14 pages.

Witkowski et al., Conversion of a beta-ketoacyl synthase to a malonyl decarboxylase by replacement of the active-site cysteine with glutamine. Biochemistry. Sep. 7, 1999;38(36):11643-50.

Wu et al., Humanization of a murine monoclonal antibody by simultaneous optimization of framework and CDR residues. J Mol Biol. Nov. 19, 1999;294(1):151-62.

Yamaguchi et al., Around hematological malignancies. Trends in Hematological Malignancies. 2010;2(2):96-98.

Yamaki et al., Preventive and therapeutic effects of rapamycin, a mammalian target of rapamycin inhibitor, on food allergy in mice. Allergy. Oct. 2012;67(10):1259-70. doi: 10.1111/aII.12000. Epub Aug. 23, 2012.

Yeste et al., Nanoparticle-mediated codelivery of myelin antigen and a tolerogenic small molecule suppresses experimental autoimmune encephalomyelitis. Proc Natl Acad Sci USA. Jul. 10, 2012;109(28):11270-5. doi: 10.1073/pnas.1120611109. Epub Jun. 27, 2012.

Yuan et al., Preparation of rapamycin-loaded chitosan/PLA nanoparticles for immunosuppression in corneal transplantation. Int J Pharm. Feb. 12, 2008;349(1-2):241-8. Epub Aug. 11, 2007.

Zhang et al., Induction of tolerance to FVIII using nanoparticles in a murine model of hemophilia A. Blood. Nov. 15, 2013;122:2337.

(56) References Cited

OTHER PUBLICATIONS

Zhang et al., The mechanism of B lymphocytes in inducing immune tolerance. Immunol J. Jul. 2010;26(7):643-6.
Zhang-Hoover et al., Tolerogenic APC generate CD8+ T regulatory cells that modulate pulmonary interstitial fibrosis. J Immunol. Jan. 1, 2004;172(1):178-85.
Zhou et al., Updates of mTOR inhibitors. Anticancer Agents Med Chem. Sep. 2010;10(7):571-81.
Zweers, Biodegradable nanoparticles of intravascular drug delivery. Unversiteit Twente, 2003.
Antignani et al., Chemical Screens Identify Drugs that Enhance or Mitigate Cellular Responses to Antibody-Toxin Fusion Proteins. PLoS One. Aug. 24, 2016;11(8):e0161415. doi: 10.1371/journal.pone.0161415. eCollection 2016. PubMed PMID: 27556570; PubMed Central PMCID: PMC4996465.
Avramis et al., Asparaginase (native ASNase or pegylated ASNase) in the treatment of acute lymphoblastic leukemia. Int J Nanomedicine. 2006;1(3):241-54. Review. PubMed PMID: 17717965; PubMed Central PMCID: PMC2426805.
Bauss et al., Characterization of a re-engineered, mesothelin-targeted Pseudomonas exotoxin fusion protein for lung cancer therapy. Mol Oncol. Oct. 2016;10(8):1317-29. doi: 10.1016/j.molonc.2016.07.003. Epub Jul. 14, 2016. PubMed PMID: 27507537; PubMed Central PMCID: PMC5423209.
Becker et al., Febuxostat compared with allopurinol in patients with hyperuricemia and gout. N Engl J Med. Dec. 8, 2005;353(23):2450-61. PubMed PMID: 16339094.
Bell et al., Analysis of tumors arising in male B6C3F1 mice with and without AAV vector delivery to liver. Mol Ther. Jul. 2006;14(1):34-44. Epub May 6, 2006.
CAS Registry No. 1841500-93-3. LMB-100 Substance. 2020.
Chung et al., Cetuximab-induced anaphylaxis and IgE specific for galactose-alpha-1,3-galactose. N Engl J Med. Mar. 13, 2008;358(11):1109-17. doi: 10.1056/NEJMoa074943. PubMed PMID: 18337601; PubMed Central PMCID: PMC2361129.
Cuburu et al., Intravaginal immunization with HPV vectors induces tissue-resident CD8+ T cell responses. J Clin Invest. Dec. 2012;122(12):4606-20. doi: 10.1172/JCI63287. Epub Nov. 12, 2012. PubMed PMID: 23143305; PubMed Central PMCID: PMC3533540.
Cunningham et al., Induction and prevention of severe hyperammonemia in the spfash mouse model of ornithine transcarbamylase deficiency using shRNA and rAAV-mediated gene delivery. Mol Ther. May 2011;19(5):854-9. doi: 10.1038/mt.2011.32. Epub Mar. 8, 2011.
Dreaden et al., Size matters: gold nanoparticles in targeted cancer drug delivery. Ther Deliv. Apr. 2012;3(4):457-78. Review. PubMed PMID: 22834077; PubMed Central PMCID: PMC3596176.
Gordon, Ornithine transcarbamylase deficiency: a urea cycle defect. Eur J Paediatr Neurol. 2003;7(3):115-21. Review.
Guo et al., PD-1 blockade and 0X40 triggering synergistically protects against tumor growth in a murine model of ovarian cancer. PLoS One. Feb. 27, 2014;9(2):e89350. doi: 10.1371/journal.pone.0089350. eCollection 2014. Erratum in: PLoS One. Oct. 18, 2017; 12 (10 ):e0186965. PubMed PMID: 24586709; PubMed Central PMCID: PMC3937343.
Hassan et al., Phase 1 study of the antimesothelin immunotoxin SS1P in combination with pemetrexed and cisplatin for front-line therapy of pleural mesothelioma and correlation of tumor response with serum mesothelin, megakaryocyte potentiating factor, and cancer antigen 125. Cancer. Nov. 1, 2014;120(21):3311-9. doi: 10.1002/cncr.28875. Epub Jul. 2, 2014. PubMed PMID: 24989332.
Hassan et al., Phase I study of SS1P, a recombinant anti-mesothelin immunotoxin given as a bolus I.V. infusion to patients with mesothelin-expressing mesothelioma, ovarian, and pancreatic cancers. Clin Cancer Res. Sep. 1, 2007;13(17):5144-9. PubMed PMID: 17785569.
Hassan et al., Pretreatment with rituximab does not inhibit the human immune response against the immunogenic protein LMB-1. Clin Cancer Res. Jan. 1, 2004; 10(1 Pt 1): 16-8. PubMed PMID: 14734446.

Hollevoet et al., In vitro and in vivo activity of the low-immunogenic antimesothelin immunotoxin RG7787 in pancreatic cancer. Mol Cancer Ther. Aug. 2014;13(8):2040-9. doi: 10.1158/1535-7163.MCT-14-0089-T. Epub Jun. 1, 20143. Erratum in: Mol Cancer Ther. Jul. 2015;14(7):1763. PubMed PMID: 24928849; PubMed Central PMCID: PMC4142475.
Jing et al., Comparison of immunosuppressive effects and ND4 expression among different immunosuppressive strategies following AAV2-ND4 gene treatment for leber hereditary optic neuropathy. Acta Med Univ Sci Technol Huazhong. Apr. 2013;42(2):187-191.
Koerber et al., Molecular evolution of adeno-associated virus for enhanced glial gene delivery. Mol Ther. Dec. 2009;17(12):2088-95. doi: 10.1038/mt.2009.184. Epub Aug. 11, 2009. PubMed PMID: 19672246; PubMed Central PMCID: PMC2788045.
Kreitman et al., Phase I trial of anti-CD22 recombinant immunotoxin moxetumomab pasudotox (CAT-8015 or HA22) in patients with hairy cell leukemia. J Clin Oncol. May 20, 2012;30(15):1822-8. doi: 10.1200/JCO.2011.38.1756. Epub Feb. 21, 2012. PubMed PMID: 22355053; PubMed Central PMCID: PMC3383181.
Kreitman et al., Phase I trial of continuous infusion anti-mesothelin recombinant immunotoxin SS1P. Clin Cancer Res. Aug. 15, 2009;15(16):5274-9. doi: 10.1158/1078-0432.CCR-09-0062. Epub Aug. 11, 2009. PubMed PMID: 19671873; PubMed Central PMCID: PMC2754261.
Kreitman et al., Phase I trial of recombinant immunotoxin anti-Tac(Fv)-PE38 (LMB-2) in patients with hematologic malignancies. J Clin Oncol. Apr. 2000;18(8):1622-36. PubMed PMID: 10764422.
Kreitman, Recombinant immunotoxins for the treatment of chemoresistant hematologic malignancies. Curr Pharm Des. 2009;15(23):2652-64. Review. PubMed PMID: 19689336.
Law. Rapamycin: an anti-cancer immunosuppressant? Crit Rev Oncol Hematol. Oct. 2005;56(1):47-60. Review. PubMed PMID: 16039868.
Leshem et al., Combining Local Immunotoxins Targeting Mesothelin with CTLA-4 Blockade Synergistically Eradicates Murine Cancer by Promoting Anticancer Immunity. Cancer Immunol Res. Aug. 2017;5(8):685-694. doi: 10.1158/2326-6066.CIR-16-0330. Epub Jul. 3, 2017. PubMed PMID: 28674083; PubMed Central PMCID: PMC5549555.
Liu et al., Recombinant immunotoxin engineered for low immunogenicity and antigenicity by identifying and silencing human B-cell epitopes. Proc Natl Acad Sci U S A. Jul. 17, 2012;109(29):11782-7. doi: 10.1073/pnas.1209292109. Epub Jul. 2, 2012. PubMed PMID: 22753489; PubMed Central PMCID: PMC3406843.
Maeda. Tumor-selective delivery of macromolecular drugs via the EPR effect: background and future prospects. Bioconjug Chem. May 19, 2010;21(5):797-802. doi: 10.1021/bc100070g. Review. PubMed PMID: 20397686.
Manoli et al., FGF21 underlies a hormetic response to metabolic stress in methylmalonic acidemia. JCI Insight. Dec. 6, 2018;3(23). pii:124351. doi: 10.1172/jci.insight.124351.
Maus et al., T cells expressing chimeric antigen receptors can cause anaphylaxis in humans. Cancer Immunol Res. Jul. 2013;1:26-31. PubMed PMID: 24432303; PubMed Central PMCID: PMC3888798.
Mazor et al., Elimination of murine and human T-cell epitopes in recombinant immuno toxin eliminates neutralizing and anti-drug antibodies in vivo. Cell Mol Immunol. May 2017;14(5):432-442. doi: 10.1038/cmi.2015.91. Epub Oct. 19, 2015. PubMed PMID: 26477977; PubMed Central PMCID: PMC5423085.
Mezzapelle et al., Human malignant mesothelioma is recapitulated in immunocompetent BALB/c mice injected with murine AB cells. Sci Rep. Mar. 10, 2016;6:22850. doi: 10.1038/srep22850. PubMed PMID: 26961782; PubMed Central PMCID: PMC4785401.
Mossoba et al., Pentostatin plus cyclophosphamide safely and effectively prevents immunotoxin immunogenicity in murine hosts. Clin Cancer Res. Jun. 1, 2011;17(11):3697-705. doi: 10.1158/1078-0432.CCR-11-0493. Epub Apr. 26, 2011. PubMed PMID: 21521777; PubMed Central PMCID: PMC3107891.
O'Donnell et al., PI3K-AKT-mTOR inhibition in cancer immunotherapy, redux. Semin Cancer Biol. Feb. 2018;48:91-103. doi: 10.1016/j.semcancer.2017.04.015. Epub May 2, 2017. Review. PubMed PMID: 28467889.

(56) References Cited

OTHER PUBLICATIONS

Pastan et al., Discovery of mesothelin and exploiting it as a target for immunotherapy. Cancer Res. Jun. 1, 2014;74(11):2907-12. doi: 10.1158/0008-5472.CAN-14-0337. Epub May 13, 2014. Review. PubMed PMID: 24824231; PubMed Central PMCID: PMC4062095.
Piconese et al., OX40 triggering blocks suppression by regulatory T cells and facilitates tumor rejection. J Exp Med. Apr. 14, 2008;205(4):825-39. doi: 10.1084/jem.20071341. Epub Mar. 24, 2008. Erratum in: J Exp Med. Jun. 9, 2008;205(6):1505. PubMed PMID: 18362171; PubMed Central PMCID:PMC2292222.
Ronzitti et al., A translationally optimized AAV-UGT1A1 vector drives safe and long-lasting correction of Crigler-Najjar syndrome. Mol Ther Methods Clin Dev. Jul. 20, 2016;3:16049. eCollection 2016.
Schlesinger et al., Treatment of chronic gouty arthritis: it is not just about urate-lowering therapy. Semin Arthritis Rheum. Oct. 2012;42(2):155-65. doi: 10.1016/j.semarthrit.2012.03.010. Epub Apr. 26, 2012. Review. PubMed PMID: 22542277.
Selby et al., Anti-CTLA-4 antibodies of IgG2a isotype enhance antitumor activity through reduction of intratumoral regulatory T cells. Cancer Immunol Res. Jul. 2013;1(1):32-42. doi: 10.1158/2326-6066.CIR-13-0013. Epub Apr. 7, 2013. PubMed PMID: 24777248.
Setiady et al., In vivo depletion of CD4+FOXP3+ Treg cells by the PC61 anti-CD25 monoclonal antibody is mediated by FcgammaRIII+ phagocytes. Eur J Immunol. Mar. 2010;40(3):780-6. doi: 10.1002/eji.200939613. PubMed PMID: 20039297.
Stallone et al., mTOR inhibitors effects on regulatory T cells and on dendritic cells. J Transl Med. May 31, 2016;14(1):152. doi: 10.1186/s12967-016-0916-7. Review. PubMed PMID: 27245075; PubMed Central PMCID: PMC4886438.
Sun et al., Immunogenic issues concerning recombinant adeno-associated virus vectors for gene therapy. Curr Gene Ther. Dec. 2002;2(4):485-500. Review. PubMed PMID: 12477257.
Tange et al., The antineoplastic drug Paclitaxel has immunosuppressive properties that can effectively promote allograft survival in a rat heart transplant model. Transplantation. Jan. 27, 2002;73(2):216-23.
Velazquez et al., Effective Depletion of Pre-existing Anti-AAV Antibodies Requires Broad Immune Targeting. Mol Ther Methods Clin Dev. Jan. 25, 2017;4:159-168. doi: 10.1016/j.omtm.2017.01.003. eCollection Mar. 17, 2017. PubMed PMID: 28345001; PubMed Central PMCID: PMC5363314.
Vilar et al., Pushing the envelope in the mTOR pathway: the second generation of inhibitors. Mol Cancer Ther. Mar. 2011;10(3):395-403. doi: 10.1158/1535-7163.MCT-10-0905. Epub Jan. 7, 2011.
Wang et al., Preclinical evaluation of a clinical candidate AAV8 vector for ornithine transcarbamylase (OTC) deficiency reveals functional enzyme from each persisting vector genome. Mol Genet Metab. Feb. 2012;105(2):203-11. doi: 10.1016/j.ymgme.2011.10.020. Epub Nov. 7, 2011.
Weng et al., The toxin component of targeted anti-tumor toxins determines their efficacy increase by saponins. Mol Oncol. Jun. 2012;6(3):323-32. doi: 10.1016/j.molonc.2012.01.004. Epub Jan. 24, 2012. PubMed PMID: 22309811; PubMed Central PMCID: PMC5528334.
Yanwei et al., High-efficiency targeted editing of large viral genomes by RNA-guided nucleases. PLoS Pathog. May 1, 2014;10(5):e1004090. doi: 10.1371/journal.ppat.1004090. eCollection May 2014.
Youn et al., Subsets of myeloid-derived suppressor cells in tumor-bearing mice. J Immunol. Oct. 15, 2008;181(8):5791-802. PubMed PMID: 18832739; PubMed Central PMCID: PMC2575748.
Youn et al., The biology of myeloid-derived suppressor cells: the blessing and the curse of morphological and functional heterogeneity. Eur J Immunol. Nov. 2010;40(11):2969-75. doi: 10.1002/eji.201040895. Review. PubMed PMID: 21061430; PubMed Central PMCID: PMC3277452.
Zhang et al., Tolerogenic nanoparticles to induce immunologic tolerance: Prevention and reversal of FVIII inhibitor formation. Cell Immunol. Mar. 2016;301:74-81. doi: 10.1016/j.cellimm.2015.11.004. Epub Dec. 11, 2015. PubMed PMID: 26687613.

U.S. Appl. No. 14/810,466, filed Jul. 27, 2015, Kishimoto et al.
U.S. Appl. No. 14/269,047, filed May 2, 2014, Maldonado et al.
U.S. Appl. No. 16/140,876, filed May 13, 2019, Kishimoto.
Chandler et al., Anc80 and SVP Rapamycin: A novel approach to AAV gene therapy for methylmalonic acidemia (P195). Human Gene Therapy. Jan. 1, 2017;28:A70.
Krensky et al., Immunosuppressants, Tolerogens, and Immunostimulants. In: Goodman and Gilman's The Pharmacological Basis of Therapeutics 12th Edition. Chapter 35. Ed.: Laurence L. Brunton. McGraw Hill Medical. 2011.
Mikuls, Antihyperuricemic Agents. Section: Uricases. Chapter 65 in Kelley's Textbook of Rheumatology (Ninth ed.). 2013:1001-1003.
Pandey et al., Photochemical linking of primary aromatic amines to carrier proteins to elicit antibody response against the amine haptens. J Immunol Methods. Nov. 20, 1986;94(1-2):237-46.
Zou et al., Rapamycin-loaded nanoparticles for inhibition of neointimal hyperplasia in experimental vein grafts. Ann Vase Surg. 2011;25(4):538-546. doi:10.1016/j.avsg.2011.01.003.
U.S. Appl. No. 15/846,958, filed Sep. 7, 2015, Kishimoto.
U.S. Appl. No. 14/934,135, filed Nov. 5, 2015, Griset et al.
U.S. Appl. No. 16/054,204, filed Aug. 6, 2018, Altreuter et al.
U.S. Appl. No. 17/186,512, filed Feb. 26, 2021, Ilyinskii et al.
[No Author Listed] Highlights of Prescribing Information, Krystexxa (pegloticase). Apr. 2012, pp. 1-14. Retrieved from https://www.accessdata.fda.gov/drugsatfda_docs/label/2012/125293s0341bl.pdf.
Aldhamen et al., Immune recognition of gene transfer vectors: focus on adenovirus as a paradigm. Frontiers in Immunology. 2011 ;2:40. DOI: 10.3389/fimmu.2011.00040.
Azeem et al., 11 Initial Phase 2 Clinical Data of SEL-212 in Symptomatic Gout Patients: Monthly Dosing of a Pegylated Uricase (Pegadricase) with Svp-Rapamycin Enables Sustained Reduction of Acute Gout Flares. Arthritis Rheumatol., Oct. 22, 2018. Retrieved from the Internet https://acrabstracts.org/abstract/initial-phase-2-clinical-data-of-sel-212-in-symptomatic-gout-patients-monthly-dosing-ofa-pegylated-uricase-pegadricase-with-svp-rapamycin-enables-sustained-reduction-of-acute-gout-flares/.
Biosis, Accession No. 2011:426302. Blood, 2010, vol. 116, No. 21, pp. 1541, STN [online], retrieved on Mar. 19, 2021.
Czock et al., Pharmacokinetics and pharmacodynamics of systemically administered glucocorticoids. Clin Pharmacokinet 2005;44(1):61-98. doi: 10.2165/00003088-200544010-00003.
Dehaan et al., Monthly Dosing of InmTOR Tolerogenic Nanoparticles Combined with Pegylated Uricase (Pegadricase) Mitigates Formation of Anti-Drug Antibodies Resulting in Sustained Uricas. American College of Rheumatology (ACR) and Association for Rheumatology Professionals (ARP) Annual Meeting, Nov. 1, 2019 (Nov. 1, 2019) Retrieved from the Internet https://acrabstracts.org/abstract/monthly-dosing-of-inmtor-tolerogenic-nanoparticles-combined-with-pegylated-uricase-pegadricase-mitigates-formation-of-anti-drug-antibodies-resulting-in-sustained-uricase-activity-in-symptomatic-gout/.
Garay et al., Therapeutic perspectives on uricases for gout. Joint Bone Spine. May 2012;79(3):237-42. doi: 10.1016/j.jbspin.2012.01.004. Epub Feb. 25, 2012.
Hao, Rehabilitation Guidelines for Kidney Transplant. Tianjin Science & Tehcnology Translation & Publishing Co., Ltd. Jun. 2006. p. 43.
Horisawa et al., Prolonged anti-inflammatory action of DL-lactide/glycolide copolymer nanospheres containing betamethasone sodium phosphate for an intra-articular delivery system in antigen-induced arthritic rabbit. Pharm Res. Apr. 2002;19(4):403-10. doi: 10.1023/a:1015123024113. PMID: 12033371.
Ilyinskii et al., Combination of an engineered AAV vector Anc80 and tolerogenic nanoparticles encapsulating rapamycin enables efficient transgene expression in mice with pre-existing neutralizing antibodies and provides a therapeutic benefit in a mouse model of methylmalonic acidemia. Changing The Face of Modern Medicine: Stem Cell and Gene Therapy. vol. 29 ( 12). Dec. 13, 2018 (Dec. 13, 2018), p. A168. DOI: 10.1089/hum.2018.29077.abstracts p. P491.
Ilyinskii et al., ImmTOR Tolerogenic Nanoparticles Enhance Transgene Expression after Both Initial and Repeat Dosing in a Mouse Model

(56) References Cited

OTHER PUBLICATIONS of Methylmalonic Acidemia Treated with an Anc80 AAV Vector. ASGCT 22nd Annual Meeting. 27(4S1);Apr. 12, 2019:pp. 14-15.

Ilyinskii et al., Tolerogenic ImmTOR™ Nanoparticles Enhance Vector Transduction, mRNA Synthesis and Transgene Expression after Initial and Repeated Administrations of AAV-Based Gene Therapy Vectors through Immunological and Non-Immunological Mechanisms. Mol Ther. Apr. 2019;29:77-78.

Jiang et al., Rapamycin enhances adenovirus-mediated cancer imaging and therapy in pre-immunized murine hosts. PLoS One. Sep. 2, 2013;8(9):e73650. doi: 10.1371/journal.pone.0073650. PMID: 24023896; PMCID: PMC3759448.

Kishimoto, Development of ImmTOR Tolerogenic Nanoparticles for the Mitigation of Anti-drug Antibodies. Front Immunol. May 20, 2020;11:969. doi: 10.3389/fimmu.2020.00969.

Kontos et al., Engineering antigens for in situ erythrocyte binding induces T-cell deletion. Proc Natl Acad Sci U S A. Jan. 2, 2013;110(1):E60-8. doi: 10.1073/pnas.1216353110. Epub Dec. 17, 2012. PMID: 23248266; PMCID: PMC3538192.

Meliani et al., Antigen-selective modulation of AAV immunogenicity with tolerogenic rapamycin nanoparticles enables successful vector re-administration. Nat Commun. Oct. 5, 2018;9(1):4098. doi: 10.1038/s41467-018-06621-3.

Nayak et al., Progress and prospects: immune responses to viral vectors. Gene Ther. Mar. 2010;17(3):295-304. doi: 10.1038/gt.2009. 148. Epub Nov. 12, 2009. Erratum in: Gene Ther. Feb. 2010;17(2):294.

Qiu et al., Impact of natural IgM concentration on gene therapy with adenovirus type 5 vectors. J Virol. Mar. 2015;89(6):3412-6. doi: 10.1128/JVI.03217-14. Epub Dec. 31, 2014. PMID: 25552715.

Sands et al., Session Title: Metabolic and Crystal Arthropathies Poster II Session Type: ACR Poster Session C Initial Phase 2 Clinical Data of SEL-212 in Symptomatic Gout Patients: Monthly Dosing of a Pegylated Uricase (Pegsiticase) with Svp-Rapamycin Enables Sustained Reduction of Serum Uric Acid Levels By Mitig 11 , 1' Sep. 8, 2017 (Sep. 18, 2017). Retrieved from https://acrabstracts.org/abstract/initial-phase-2-clinical-data-of-sel-212-in-sy mptomatic-gout-patients-monthly-dosing-ofa-pegylated-uricase-pegsiticase-with-svp-rapamycin-enables-sustained-reduction-of-serum-uric-acid-levels-by-m/ on Sep. 14, 2020.

Smolinksi, SAT0402 SEL-212 Phase 2 Clinical Study In Symptomatic Gout Patients: Immtor Tolerogenic Nanoparticles Combined With Pegadricase Mitigates Immunogenicity and Enables Sustained Reduction of Serum Uric Acid Levels, Low Rate of Gout Flares and Monthly Dosing. Annals Rheum Dis. Jun. 2019;78(Suppl 2):1288-1289.

U.S. Appl. No. 12/764,569, filed Apr. 21, 2010, Lipford et al.
U.S. Appl. No. 12/788,261, filed May 26, 2010, Lipford et al.
U.S. Appl. No. 12/862,076, filed Aug. 24, 2010, Fraser et al.
U.S. Appl. No. 13/116,453, filed May 26, 2011, Bratzler et al.
U.S. Appl. No. 13/116,488, filed May 26, 2011, Bratzler et al.
U.S. Appl. No. 13/116,556, filed May 26, 2011, Bratzler et al.
U.S. Appl. No. 13/428,340, filed Mar. 23, 2012, Altreuter et al.
U.S. Appl. No. 13/457,994, filed Apr. 27, 2012, Fraser et al.
U.S. Appl. No. 13/560,955, filed Jul. 27, 2012, Altreuter et al.
U.S. Appl. No. 13/948,129, filed Jul. 22, 2013, Zepp et al.
U.S. Appl. No. 14/269,048, filed May 2, 2014, Maldonado.
U.S. Appl. No. 14/269,056, filed May 2, 2014, Maldonado et al.
U.S. Appl. No. 14/269,042, filed May 2, 2014, Kishimoto et al.
U.S. Appl. No. 14/296,204, filed Jun. 4, 2014, Maldonado et al.
U.S. Appl. No. 14/742,583, filed Jun. 17, 2015, Kishimoto.
U.S. Appl. No. 14/751,106, filed Jun. 25, 2015, Kishimoto et al.
U.S. Appl. No. 14/810,418, filed Jul. 27, 2015, Fraser et al.
U.S. Appl. No. 14/810,427, filed Jul. 27, 2015, Fraser et al.
U.S. Appl. No. 14/810,442, filed Jul. 27, 2015, Fraser et al.
U.S. Appl. No. 14/810,450, filed Jul. 27, 2015, Fraser et al.
U.S. Appl. No. 14/810,457, filed Jul. 27, 2015, Kishimoto et al.
U.S. Appl. No. 14/810,476, filed Jul. 27, 2015, Maldonado.
U.S. Appl. No. 14/846,949, filed Sep. 7, 2015, Kishimoto.
U.S. Appl. No. 14/846,952, filed Sep. 7, 2015, Kishimoto.
U.S. Appl. No. 14/846,958, filed Sep. 7, 2015, Kishimoto.
U.S. Appl. No. 14/934,132, filed Nov. 5, 2015, Griset et al.
U.S. Appl. No. 14/934,134, filed Nov. 5, 2015, Griset et al.
U.S. Appl. No. 15/050,397, filed Feb. 22, 2016, Fraser et al.
U.S. Appl. No. 15/061,096, filed Mar. 4, 2016, Fraser et al.
U.S. Appl. No. 15/061,204, filed Mar. 4, 2016, Kishimoto et al.
U.S. Appl. No. 15/456,520, filed Mar. 11, 2017, Johnston.
U.S. Appl. No. 15/629,973, filed Jun. 22, 2017, Lipford et al.
U.S. Appl. No. 15/684,896, filed Aug. 23, 2017, Ilyinskii et al.
U.S. Appl. No. 15/685,648, filed Aug. 24, 2017, O'Neil.
U.S. Appl. No. 15/717,710, filed Sep. 27, 2017, Kishimoto.
U.S. Appl. No. 15/863,076, filed Jan. 5, 2018, Ilyinskii et al.
U.S. Appl. No. 15/889,014, filed Feb. 5, 2018, Zepp et al.
U.S. Appl. No. 16/056,204, filed Aug. 6, 2018, Altreuter et al.
U.S. Appl. No. 16/100,040, filed Aug. 9, 2018, Kishimoto.
U.S. Appl. No. 16/159,166, filed Oct. 12, 2018, Ilyinskii et al.
U.S. Appl. No. 16/410,876, filed May 13, 2019, Kishimoto.
U.S. Appl. No. 16/433,622, filed Jun. 6, 2019, Maldonado et al.
U.S. Appl. No. 16/438,147, filed Jun. 11, 2019, Maldonado.
U.S. Appl. No. 16/513,566, filed Jul. 16, 2019, Keller.
U.S. Appl. No. 16/513,576, filed Jul. 16, 2019, Keller.
U.S. Appl. No. 16/536,154, filed Aug. 8, 2019, Fraser et al.
U.S. Appl. No. 16/550,725, filed Aug. 26, 2019, Maldonado et al.
U.S. Appl. No. 16/560,419, filed Sep. 4, 2019, Kishimoto et al.
U.S. Appl. No. 16/739,450, filed Jan. 10, 2020, Zepp et al.
U.S. Appl. No. 16/773,551, filed Jan. 27, 2020, Lipford et al.
U.S. Appl. No. 16/858,349, filed Apr. 24, 2020, Maldonado.
U.S. Appl. No. 16/860,729, filed Apr. 28, 2020, Kishimoto et al.
U.S. Appl. No. 16/885,758, filed May 28, 2020, Kishimoto et al.
U.S. Appl. No. 16/893,153, filed Jun. 4, 2020, Johnston et al.
U.S. Appl. No. 17/076,080, filed Oct. 21, 2020, Ilyinskii et al.
U.S. Appl. No. 17/092,148, filed Nov. 6, 2020, Johnston et al.
U.S. Appl. No. 17/154,414, filed Jan. 21, 2021, Altreuter et al.
U.S. Appl. No. 17/187,512, filed Feb. 26, 2021, Ilyinskii et al.
U.S. Appl. No. 17/199,130, filed Mar. 11, 2021, Johnston.
U.S. Appl. No. 17/211,459, filed Mar. 24, 2021, Kishimoto.
U.S. Appl. No. 17/519,413, filed Nov. 4, 2021, Kishimoto.
U.S. Appl. No. 17/552,392, filed Dec. 16, 2021, Altreuter et al.
U.S. Appl. No. 17/690,437, filed Mar. 9, 2022, Maldonado.

[No Author Listed] 3SBio Inc. Exclusively Licenses Pegsiticase (Uricase PEG-20) to Selecta Biosciences to Develop Drug Candidate to Treat Gout. Cision PR Newswire. Jun. 18, 2014.

Davis et al., Hypouricaemic effect of polyethyleneglycol modified urate oxidase. Lancet. Aug. 8, 1981;2(8241):281-3. doi: 10.1016/s0140-6736(81)90528-6. PMID: 6114326.

Franks et al. Non-equivalence of different evaluation algorithms to derive mean particle size from dynamic light scattering data. J Nanopart Res 21, 195 (2019). https://doi.org/10.1007/s11051-019-4630-2.

Kang et al., De novo induction of antigen-specific CD4+CD25+ Foxp3+ regulatory T cells in vivo following systemic antigen administration accompanied by blockade of mTOR. J Leukoc Biol. May 2008;83(5):1230-9. doi: 10.1189/jlb.1207851. Epub Feb. 12, 2008.

Marwa et al., Type IV Hypersensitivity Reaction. Aug. 14, 2021. In: StatPearls [Internet]. Treasure Island (FL): StatPearls Publishing; Jan. 2021.

Taniguchi, Treatment of refractory gout with Pegloticase. Hyperuricemia and Gout. 2014;22(2):147-152.

Uermosi et al., Mechanisms of allergen-specific desensitization. J Allergy Clin Immunol. Aug. 2010;126(2):375-83. doi: 10.1016/j.jaci.2010.05.040. Epub Jul. 10, 2010. PMID: 20624641.

\* cited by examiner

Fig. 4

Phase 1a Cohort #3

Uricase-Specific ADA Titers and Serum Uric Acid Level

| Subject number | Baseline | | Day 7 | | Day 14 | | Day 21 | | Day 30 | |
|---|---|---|---|---|---|---|---|---|---|---|
| | Uric acid (mg/dl) | ADA (Titer) | Uric acid (mg/dl) | ADA (Titer) | Uric acid (mg/dl) | ADA (Titer) | Uric acid (mg/dl) | ADA (Titer) | Uric acid (mg/dl) | ADA (Titer) |
| 1 | 7.4 | Neg | <0.1 | Neg | 5 | 9720 | 6 | N.A. | 6.9 | 3240 |
| 2 | 7.5 | Neg | <0.1 | 40 | <0.1 | 40 | <0.1 | N.A. | 0.4 | 40 |
| 3 | 7.3 | 120 | <0.1 | 120 | 6.9 | 9720 | 7.6 | N.A. | 7.9 | 3240 |
| 4 | 7.6 | Neg | <0.1 | Neg | 6.1 | 3240 | 7.5 | N.A. | 7.6 | 1080 |
| 5 | 4.9 | Neg | <0.1 | Neg | <0.1 | 1080 | 0.3 | N.A. | 5.1 | 1080 |

Phase 1b Cohort #9

Uricase-Specific ADA Titers and Serum Uric Acid Level

| Subject number | Baseline | | Day 7 | | Day 14 | | Day 21 | | Day 30 | |
|---|---|---|---|---|---|---|---|---|---|---|
| | Uric acid (mg/dl) | ADA (Titer) | Uric acid (mg/dl) | ADA (Titer) | Uric acid (mg/dl) | ADA (Titer) | Uric acid (mg/dl) | ADA (Titer) | Uric acid (mg/dl) | ADA (Titer) |
| 1 | 5.4 | Neg | <0.1 | N.A. | 5.6 | 1080 | 5.8 | 1080 | 7 | 1080 |
| 2 | 5.3 | Neg | <0.1 | N.A. | 5.8 | 29160 | 6.5 | 29160 | 6 | 9720 |
| 3 | 7.4 | Neg | <0.1 | N.A. | <0.1 | 3240 | <0.1 | 1080 | 1.9 | 1080 |
| 4 | 7.2 | Neg | <0.1 | N.A. | 3.2 | 3240 | 7 | 3240 | 6.3 | 1080 |
| 5 | 8.1 | Neg | <0.1 | N.A. | <0.1 | 29160 | 7.8 | 9720 | 8.8 | 9720 |

Phase 1b Cohort #4

Uricase-Specific ADA Titers and Serum Uric Acid Level

| Subject number | Baseline | | Day 7 | | Day 14 | | Day 21 | | Day 30 | |
|---|---|---|---|---|---|---|---|---|---|---|
| | Uric acid (mg/dl) | ADA (Titer) | Uric acid (mg/dl) | ADA (Titer) | Uric acid (mg/dl) | ADA (Titer) | Uric acid (mg/dl) | ADA (Titer) | Uric acid (mg/dl) | ADA (Titer) |
| 1 | 6.7 | Neg | <0.1 | N.A. | <0.1 | Neg | <0.1 | Neg | <0.1 | Neg |
| 2 | 5.8 | Neg | <0.1 | N.A. | <0.1 | Neg | <0.1 | Neg | <0.1 | Neg |
| 3 | 7.3 | Neg | <0.1 | N.A. | <0.1 | 1080 | 4.8 | 29160 | 6.1 | 29160 |
| 4 | 6.2 | Neg | <0.1 | N.A. | <0.1 | Neg | <0.1 | Neg | <0.1 | 120 |
| 5 | 5.5 | Neg | <0.1 | N.A. | <0.1 | 40 | <0.1 | Neg | <0.1 | Neg |

Phase 1b Cohort #6

Uricase-Specific ADA Titers and Serum Uric Acid Level

| Subject number | Baseline | | Day 7 | | Day 14 | | Day 21 | | Day 30 | |
|---|---|---|---|---|---|---|---|---|---|---|
| | Uric acid (mg/dl) | ADA (Titer) | Uric acid (mg/dl) | ADA (Titer) | Uric acid (mg/dl) | ADA (Titer) | Uric acid (mg/dl) | ADA (Titer) | Uric acid (mg/dl) | ADA (Titer) |
| 1 | 7 | Neg | <0.1 | N.A. | <0.1 | Neg | <0.1 | Neg | <0.1 | Neg |
| 2 | 7.4 | Neg | <0.1 | N.A. | <0.1 | Neg | <0.1 | Neg | <0.1 | Neg |
| 3 | 7.5 | Neg | <0.1 | N.A. | <0.1 | Neg | <0.1 | Neg | <0.1 | Neg |
| 4 | 5.6 | 120 | <0.1 | N.A. | <0.1 | 120 | <0.1 | 120 | <0.1 | 120 |
| 5 | 5.9 | Neg | <0.1 | N.A. | <0.1 | Neg | <0.1 | Neg | <0.1 | Neg |

(Neg = Negative; N.A. = Sample not available)

Fig. 7

Serum Uric Acid Levels by Cohort

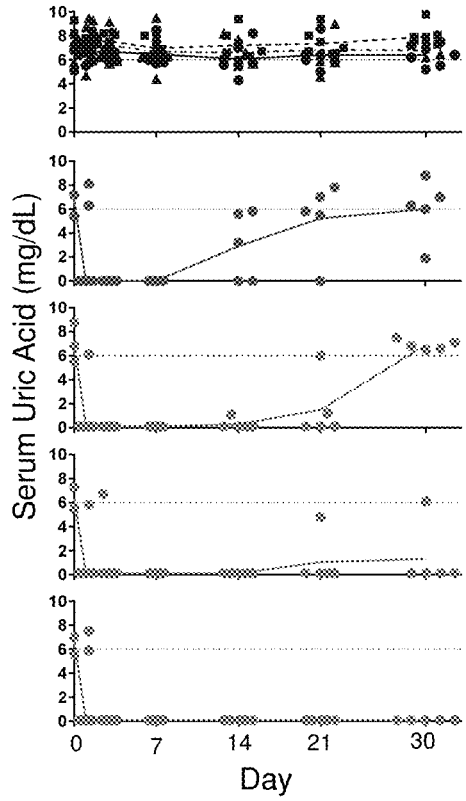

SVP-Rapamycin only
(0.03●, 0.1■, and 0.3▲mg/kg)

Pegsiticase only
(0.4mg/kg)

SEL-212
(0.03mg/kg SVP-Rapamycin
+ 0.4mg/kg pegsiticase)

SEL-212
(0.1mg/kg SVP-Rapamycin
+ 0.4mg/kg pegsiticase)

SEL-212
(0.3mg/kg SVP-Rapamycin
+ 0.4mg/kg pegsiticase)

Day 30 sUA levels and ADA levels

Pegsiticase alone (0.4 mg/kg)

| Subject number | Day 30 ||
|---|---|---|
| | Uric acid (mg/dL) | ADA (Titer) |
| 108-0010 | 7 | 1080 |
| 103-0015 | 6 | 9720 |
| 104-0032 | 1.9 | 1080 |
| 109-0012 | 6.3 | 1080 |
| 104-0036 | 8.8 | 9720 |

SEL-212 0.1 mg/kg SVP-Rapamycin + 0.4 mg/kg Pegsiticase

| Subject number | Day 30 ||
|---|---|---|
| | Uric acid (mg/dL) | ADA (Titer) |
| 107-0018 | <0.1 | Neg |
| 107-0021 | <0.1 | Neg |
| 104-0027 | 6.1 | 29160 |
| 108-0008 | <0.1 | 120 |
| 102-0005 | <0.1 | Neg |

SEL-212 0.3 mg/kg SVP-Rapamycin + 0.4 mg/kg Pegsiticase

| Subject number | Day 30 ||
|---|---|---|
| | Uric acid (mg/dL) | ADA (Titer) |
| 107-0027 | <0.1 | Neg |
| 107-0028 | <0.1 | Neg |
| 104-0050 | <0.1 | Neg |
| 104-0060 | <0.1 | 120 |
| 103-0019 | <0.1 | Neg |

(Neg = Negative)

Fig. 8

| Cohort | SEL-110 | SEL-037 |
|---|---|---|
| 1 | NA | 0.2 mg/kg |
| 2 | NA | 0.4 mg/kg |
| 3 | 0.05mg/kg | 0.2 mg/kg |
| 4 | 0.05mg/kg | 0.4 mg/kg |
| 5 | 0.08mg/kg | 0.2 mg/kg |
| 6 | 0.08mg/kg | 0.4 mg/kg |

# METHODS AND COMPOSITIONS RELATED TO COMBINED TREATMENT WITH ANTIINFLAMMATORIES AND SYNTHETIC NANOCARRIERS COMPRISING AN IMMUNOSUPPRESSANT

RELATED APPLICATION

This application claims the benefit of priority under 35 U.S.C. § 119 of U.S. provisional application 62/470,250 filed Mar. 11, 2017, the entire contents of which are incorporated herein by reference.

FIELD OF THE INVENTION

Provided herein are methods and compositions, such as kits, related to compositions comprising synthetic nanocarriers comprising an immunosuppressant and compositions comprising an uricase and a composition comprising an anti-inflammatory therapeutic. Also provided herein are methods and compositions for the treatment of subjects in need of administration or treatment with the uricase.

SUMMARY OF THE INVENTION

In one aspect, a method, comprising concomitantly administering to a subject in need thereof 1) a composition comprising synthetic nanocarriers comprising an immunosuppressant and 2) a composition comprising an uricase; and further comprising administering 3) a composition comprising an anti-inflammatory therapeutic, wherein the composition comprising an anti-inflammatory therapeutic is administered concomitantly with the composition comprising synthetic nanocarriers comprising an immunosuppressant and the composition comprising an uricase is provided.

In one embodiment of any one of the methods or compositions provided herein the composition comprising an anti-inflammatory therapeutic is administered prior to the composition comprising synthetic nanocarriers comprising an immunosuppressant and the composition comprising an uricase. In one embodiment of any one of the methods or compositions provided herein the anti-inflammatory therapeutic is administered at least once prior. In one embodiment of any one of the methods or compositions provided herein the anti-inflammatory therapeutic is administered a week prior.

In one embodiment of any one of the methods or compositions provided herein the anti-inflammatory therapeutic is a NSAID. In one embodiment of any one of the methods or compositions provided herein the anti-inflammatory therapeutic is colchicine or ibuprofen.

In one embodiment of any one of the methods provided herein the method further comprises administering to the subject one or more compositions comprising an infusion reaction therapeutic. In one embodiment of any one of the methods provided herein the method comprises the administration of at least two infusion reaction therapeutics.

In one embodiment of any one of the methods or compositions provided herein the infusion reaction therapeutic(s) comprise an antihistamine and/or a corticosteroid. In one embodiment of any one of the methods or compositions provided herein the antihistamine is fexofenadine. In one embodiment of any one of the methods or compositions provided herein the corticosteroid is methylprednisolone, prednisone or dexamethasone.

In one embodiment of any one of the methods provided herein the composition(s) comprising an infusion reaction therapeutic is/are administered concomitantly with the composition comprising synthetic nanocarriers comprising an immunosuppressant and the composition comprising an uricase. In one embodiment of any one of the methods provided herein the composition(s) comprising an infusion reaction therapeutic is/are administered at least once prior to the composition comprising synthetic nanocarriers comprising an immunosuppressant and the composition comprising an uricase. In one embodiment of any one of the methods provided herein the composition(s) comprising an infusion reaction therapeutic is/are administered at least twice prior to the composition comprising synthetic nanocarriers comprising an immunosuppressant and the composition comprising an uricase. In one embodiment of any one of the methods provided herein the composition(s) comprising an infusion reaction therapeutic is/are administered within 24 hours of the composition comprising synthetic nanocarriers comprising an immunosuppressant and the composition comprising an uricase.

In one embodiment of any one of the methods or compositions provided herein the uricase is pegylated uricase. In one embodiment of any one of the methods or compositions provided herein the pegylated uricase is pegsiticase (i.e., pegadricase) or pegloticase. In one embodiment of any one of the methods or compositions provided herein the immunosuppressant is an mTOR inhibitor. In one embodiment of any one of the methods or compositions provided herein the mTOR inhibitor is a rapalog. In one embodiment of any one of the methods or compositions provided herein the rapalog is rapamycin.

In one embodiment of any one of the methods provided herein the subject is human. In one embodiment of any one of the methods provided herein the subject is a subject with an elevated serum uric acid level and/or undesired uric acid deposits. In one embodiment of any one of the methods provided herein the subject has hyperuricemia. In one embodiment of any one of the methods provided herein the subject has gout or a condition associated with gout. In one embodiment of any one of the methods provided herein the subject has acute gout; chronic gout with or without tophi; idiopathic gout; refractory gout, such as chronic refractory gout; secondary gout; unspecified gout; gout associated with a cardiovascular condition, renal condition, pulmonary condition, neurological condition, ocular condition, dermatological condition or hepatic condition; or has had a gout attack or gout flare.

In one embodiment of any one of the methods or compositions provided herein the immunosuppressant is encapsulated in the synthetic nanocarriers. In one embodiment of any one of the methods or compositions provided herein the synthetic nanocarriers are polymeric synthetic nanocarriers. In one embodiment of any one of the methods or compositions provided herein the polymeric synthetic nanocarriers comprise a hydrophobic polyester. In one embodiment of any one of the methods or compositions provided herein the hydrophobic polyester comprises PLA, PLG, PLGA or polycaprolactone. In one embodiment of any one of the methods or compositions provided herein the polymeric synthetic nanocarriers further comprise PEG. In one embodiment of any one of the methods or compositions provided herein the PEG is conjugated to the PLA, PLG, PLGA or polycaprolactone. In one embodiment of any one of the methods or compositions provided herein the polymeric synthetic nanocarriers comprise PLA, PLG, PLGA or polycaprolactone and PEG conjugated to PLA, PLG, PLGA or polycaprolactone. In one embodiment of any one of the methods or compositions provided herein the polymeric synthetic nanocarriers comprise PLA and PLA-PEG.

In one embodiment of any one of the methods or compositions provided herein the mean of a particle size distribution obtained using dynamic light scattering of the synthetic nanocarriers is a diameter greater than 120 nm. In one embodiment of any one of the methods or compositions provided herein the diameter is greater than 150 nm. In one embodiment of any one of the methods or compositions provided herein the diameter is greater than 200 nm. In one embodiment of any one of the methods or compositions provided herein the diameter is greater than 250 nm. In one embodiment of any one of the methods or compositions provided herein the diameter is less than 500 nm. In one embodiment of any one of the methods or compositions provided herein the diameter is less than 450 nm. In one embodiment of any one of the methods or compositions provided herein the diameter is less than 400 nm. In one embodiment of any one of the methods or compositions provided herein the diameter is less than 350 nm. In one embodiment of any one of the methods or compositions provided herein the diameter is less than 300 nm. In one embodiment of any one of the methods or compositions provided herein the diameter is less than 250 nm. In one embodiment of any one of the methods or compositions provided herein the diameter is less than 200 nm.

In one embodiment of any one of the methods or compositions provided herein the load of the immunosuppressant of the synthetic nanocarriers is 7-12% or 8-12% by weight. In one embodiment of any one of the methods or compositions provided herein the load of the immunosuppressant of the synthetic nanocarriers is 7-10% or 8-10% by weight. In one embodiment of any one of the methods or compositions provided herein the load of the immunosuppressant of the synthetic nanocarriers is 7%, 8%, 9%, 10%, 11%, or 12% by weight.

In one embodiment of any one of the methods provided herein the administration of any one of or the set of compositions is repeated. In one embodiment of any one of the methods provided herein the repeated administrations of the composition(s) are repeated on a monthly basis. In one embodiment of any one of the methods provided herein the composition comprising the anti-inflammatory therapeutic of each repeated administration is given as in any one of the methods provided herein relative to the time of the corresponding repeated administration of the composition comprising synthetic nanocarriers comprising an immunosuppressant and the composition comprising an uricase. In one embodiment of any one of the methods provided herein the composition(s) comprising the infusion reaction therapeutic(s) of each repeated administration is given as in any one of the methods provided herein relative to the time of the corresponding repeated administration of the composition comprising synthetic nanocarriers comprising an immunosuppressant and the composition comprising an uricase.

In one embodiment of any one of the methods provided herein the administration of the composition comprising synthetic nanocarriers comprising an immunosuppressant and the composition comprising an uricase is according to the doses and/or frequencies and/or timing, respectively, of any one of the methods provided herein. In one embodiment of any one of the methods provided herein the administration of the composition comprising synthetic nanocarriers comprising an immunosuppressant, the composition comprising an uricase, and the composition comprising an anti-inflammatory therapeutic is according to the doses and/or frequencies and/or timing, respectively, of any one of the methods provided herein. In one embodiment of any one of the methods provided herein the administration of the composition comprising synthetic nanocarriers comprising an immunosuppressant, the composition comprising an uricase, the composition comprising an anti-inflammatory therapeutic, and the one or more compositions comprising an infusion reaction therapeutic is according to the doses and/or frequencies and/or timing, respectively, of any one of the methods provided herein. Any one of the respective doses and/or frequencies and/or timing can be used for any one of the methods provided herein for the respective composition.

In one embodiment of any one of the methods provided herein the administration of the composition comprising synthetic nanocarriers comprising an immunosuppressant and the composition comprising an uricase is according to any one of the regimens, respectively, provided herein. In one embodiment of any one of the methods provided herein the administration of the composition comprising synthetic nanocarriers comprising an immunosuppressant, the composition comprising an uricase and the composition comprising an anti-inflammatory therapeutic is according to any one of the regimens, respectively, provided herein. In one embodiment of any one of the methods provided herein the administration of the composition comprising synthetic nanocarriers comprising an immunosuppressant, the composition comprising an uricase, the composition comprising an anti-inflammatory therapeutic and the one or more compositions comprising an infusion reaction therapeutic is according to any one of the regimens, respectively, provided herein. Any one of the respective regimens can be used for any one of the methods provided herein for the respective composition.

In one embodiment of any one of the methods provided herein the administration of the composition comprising synthetic nanocarriers comprising an immunosuppressant is given according the any one of the modes of administration provided herein. In one embodiment of any one of the methods provided herein the administration of the composition comprising an uricase is given according the any one of the modes of administration provided herein. In one embodiment of any one of the methods provided herein the administration of the composition comprising an anti-inflammatory therapeutic is given according the any one of the modes of administration provided herein. In one embodiment of any one of the methods provided herein the administration of the composition(s) comprising an infusion reaction therapeutic is/are given according the any one of the modes of administration provided herein.

In one aspect a composition, comprising 1) a composition comprising synthetic nanocarriers comprising an immunosuppressant and 2) a composition comprising an uricase; and further comprising administering 3) a composition comprising an anti-inflammatory therapeutic is provided.

BRIEF DESCRIPTION OF THE DRAWINGS

FIG. 4 is a graphical illustration showing the serum uric acid levels and uricase-specific ADA levels for each subject in Cohort #3 of the Phase 1a clinical trial and Cohort #9, Cohort #4, and Cohort #6 in the Phase 1b clinical trial.

FIG. 7 is a graphical illustration showing the serum uric acid levels of subjects treated with pegstiticase alone, or in combination with synthetic nanocarriers comprising rapamycin (SVP-Rapamycin) (0.1 or 0.3 mg/kg).

FIG. 8 shows doses for the phase 2 clinical trial.

DETAILED DESCRIPTION OF THE INVENTION

A. Overview

Figure 1:
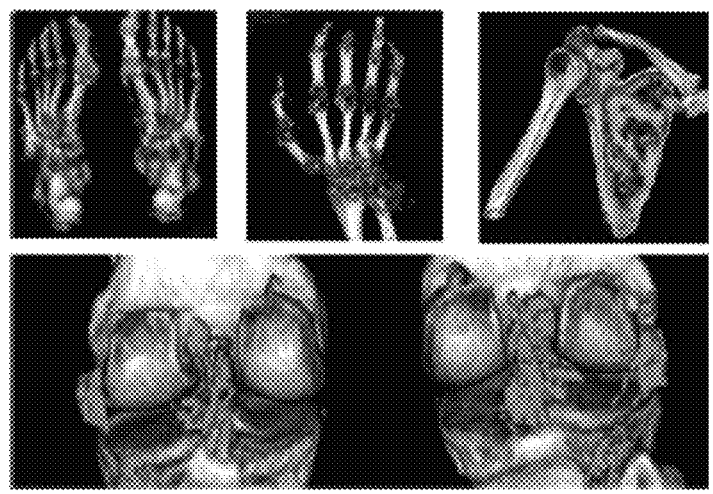
FIG. 1 is an image showing tophi/uric acid deposits visualized using DECT.

Anti-drug antibodies (ADAs) can be a complication with treatment with soluble therapeutic proteins, such as the possibility of reduced efficacy. In addition, with treatment of subjects with conditions associate with gout, gout flares can increase when efficacy is increased. It has been surprisingly found that the administration of an anti-inflammatory therapeutic with a composition comprising synthetic nanocarriers comprising an immunosuppressant and a composition comprising an uricase can result in better efficacy of treatment as well as gout flare reduction. This unexpected outcome is significantly better than with other therapies as shown in Table 4. Specifically, a combination assessment of glare frequency as well as the area under the curve of mean sUA (serum uric acid) levels over time was performed. The finding of both improved efficacy and reduced gout flares was surprising with the SEL-212 study drug and anti-inflammatory treatment.

B. Definitions

"Administering" or "administration" or "administer" means giving a material to a subject in a manner such that there is a pharmacological result in the subject. This may be direct or indirect administration, such as by inducing or directing another subject, including another clinician or the subject itself, to perform the administration.

"Amount effective" in the context of a composition or dose for administration to a subject refers to an amount of the composition or dose that produces one or more desired responses in the subject. In some embodiments, the amount effective is a pharmacodynamically effective amount. Therefore, in some embodiments, an amount effective is any amount of a composition or dose provided herein that produces one or more of the desired therapeutic effects and/or immune responses as provided herein. This amount can be for in vitro or in vivo purposes. For in vivo purposes, the amount can be one that a clinician would believe may have a clinical benefit for a subject in need thereof. Any one of the compositions or doses, including label doses, as provided herein can be in an amount effective.

Amounts effective can involve reducing the level of an undesired response, although in some embodiments, it involves preventing an undesired response altogether. Amounts effective can also involve delaying the occurrence of an undesired response. An amount that is effective can also be an amount that produces a desired therapeutic endpoint or a desired therapeutic result. In other embodiments, the amounts effective can involve enhancing the level of a desired response, such as a therapeutic endpoint or result. Amounts effective, preferably, result in a therapeutic result or endpoint and/or reduced or eliminated ADAs against the treatment and/or reduced gout flare frequency in combination with improved efficacy in any one of the subjects provided herein. The achievement of any of the foregoing can be monitored by routine methods.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

Doses of the components in any one of the compositions of the invention or used in any one of the methods of the invention may refer to the amount of the components in the composition, the actual amounts of the respective components received by an administered subject, or the amount that appears on a label (also referred to herein as label dose). The dose can be administered based on the number of synthetic nanocarriers that provide the desired amount of the component(s).

"Antihistamine" refer to agents that block the effects of histamine.

"Attach" or "Attached" or "Couple" or "Coupled" (and the like) means to chemically associate one entity (for example a moiety) with another. In some embodiments, the attaching is covalent, meaning that the attachment occurs in the context of the presence of a covalent bond between the two entities. In non-covalent embodiments, the non-covalent attaching is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In embodiments, encapsulation is a form of attaching.

"Average", as used herein, refers to the arithmetic mean unless otherwise noted.

"Concomitantly" means administering two or more materials/agents to a subject in a manner that is correlated in time, preferably sufficiently correlated in time so as to provide a modulation in a physiologic or immunologic response, and even more preferably the two or more materials/agents are administered in combination. In embodiments, concomitant administration may encompass administration of two or more materials/agents within a specified period of time, preferably within 1 month, more preferably within 1 week, still more preferably within 1 day, and even more preferably within 1 hour. In embodiments, the two or more materials/agents are sequentially administered. In embodiments, the materials/agents may be repeatedly administered concomitantly; that is concomitant administration on more than one occasion.

"Dose" refers to a specific quantity of a pharmacologically active material for administration to a subject for a given time. Unless otherwise specified, the doses recited for compositions comprising pegylated uricase refer to the weight of the uricase (i.e., the protein without the weight of the PEG or any other components of the composition comprising the pegylated uricase). Also, unless otherwise specified, the doses recited for compositions comprising synthetic nanocarriers comprising an immunosuppressant refer to the weight of the immunosuppressant (i.e., without the weight of the synthetic nanocarrier material or any of the other components of the synthetic nanocarrier composition). When referring to a dose for administration, in an embodiment of any one of the methods, compositions or kits provided herein, any one of the doses provided herein is the dose as it appears on a label/label dose.

"Encapsulate" means to enclose at least a portion of a substance within a synthetic nanocarrier. In some embodiments, a substance is enclosed completely within a synthetic nanocarrier. In other embodiments, most or all of a substance that is encapsulated is not exposed to the local environment external to the synthetic nanocarrier. In other embodiments, no more than 50%, 40%, 30%, 20%, 10% or 5% (weight/weight) is exposed to the local environment. Encapsulation is distinct from absorption, which places most or all of a substance on a surface of a synthetic nanocarrier, and leaves the substance exposed to the local environment external to the synthetic nanocarrier. In embodiments of any one of the methods or compositions provided herein, the immunosuppressants are encapsulated within the synthetic nanocarriers.

"Elevated serum uric acid level" refers to any level of uric acid in a subject's serum that may lead to an undesirable result or would be deemed by a clinician to be elevated. In an embodiment, the subject of any one of the methods provided herein can have a serum uric acid level of ≥5 mg/dL, ≥6 mg/dL, or ≥7 mg/dL. Such a subject may be a hyperuremic subject. Whether or not a subject has elevated blood uric acid levels can be determined by a clinician, and in some embodiments, the subject is one in which a clinician has identified or would identify as having elevated serum uric acid levels.

"Gout" generally refers to a disorder or condition associated with the buildup of uric acid, such as deposition of uric crystals in tissues and joints, and/or a clinically relevant elevated serum uric acid level. Accumulation of uric acid may be due to overproduction of uric acid or reduced excretion of uric acid. Gout may range from asymptomatic to severe and painful inflammatory conditions. A "condition associated with gout" refers to any condition in a subject where the subject experiences local and/or systemic effects of gout, including inflammation and immune responses, and in which the condition is caused or exacerbated by, or the condition can result in or exacerbate, gout. A gout flare is an "attack" or exacerbation of gout symptoms, which can happen at any time. Gout flares can include gout flares that occur after the administration of a uric acid lowering therapy.

"Hydrophobic polyester" refers to any polymer that comprises one or more polyester polymers or units thereof and that has hydrophobic characteristics. Polyester polymers include, but are not limited to, PLA, PLGA, PLG and polycaprolactone. "Hydrophobic" refers to a material that does not substantially participate in hydrogen bonding to water. Such materials are generally non-polar, primarily non-polar, or neutral in charge. Synthetic nanocarriers may be completely comprised of hydrophobic polyesters or units thereof. In some embodiments, however, the synthetic nanocarriers comprise hydrophobic polyesters or units thereof in combination with other polymers or units thereof. These other polymers or units thereof may by hydrophobic but are not necessarily so. In some preferred embodiments, when synthetic nanocarriers include one or more other polymers or units thereof in addition to a hydrophobic polyester, the matrix of other polymers or units thereof with the hydrophobic polyester is hydrophobic overall. Examples of synthetic nanocarriers that can be used in the invention and that comprise hydrophobic polyesters can be found in U.S. Publication Nos. US 2016/0128986 and US 2016/0128987, and such synthetic nanocarriers and the disclosure of such synthetic nanocarriers is incorporated herein by reference.

"Immunosuppressant", as used herein, means a compound that can cause a tolerogenic immune response specific to an antigen, also referred to herein as an "immunosuppressive effect". An immunosuppressive effect generally refers to the production or expression of cytokines or other factors by an antigen-presenting cell (APC) that reduces, inhibits or prevents an undesired immune response or that promotes a desired immune response, such as a regulatory immune response, against a specific antigen. When the APC acquires an immunosuppressive function (under the immunosuppressive effect) on immune cells that recognize an antigen presented by this APC, the immunosuppressive effect is said to be specific to the presented antigen. Examples of immunosuppressants include "mTOR inhibitors", a class of drugs that inhibit mTOR, a serine/threonine-specific protein kinase that belongs to the family of phosphatidylinositol-3 kinase (PI3K) related kinases (PIKKs). mTOR inhibitors include, but are not limited to, rapalogs, such as rapamycin, as well as ATP-competitive mTOR kinase inhibitors, such as mTORC1/mTORC2 dual inhibitors.

In embodiments of any one of the methods, compositions or kits provided herein, the immunosuppressants provided herein are attached to synthetic nanocarriers. In preferable embodiments, the immunosuppressant is an element that is in addition to the material that makes up the structure of the synthetic nanocarrier. For example, in one embodiment, where the synthetic nanocarrier is made up of one or more polymers, the immunosuppressant is a compound that is in addition and attached to the one or more polymers. In embodiments, such as where the material of the synthetic nanocarrier also results in an immunosuppressive effect, the immunosuppressant is an element present in addition to the material of the synthetic nanocarrier that results in an immunosuppressive effect.

"Infusion reaction therapeutics" are therapeutics that can be beneficial in reducing or preventing infusion reactions. Examples of such therapeutics include anti-inflammatories, such as corticosteroids.

"Load", when comprised in a composition comprising a synthetic nanocarrier, such as coupled thereto, is the amount of the immunosuppressant in the composition based on the total dry recipe weight of materials in an entire synthetic nanocarrier (weight/weight). Generally, such a load is calculated as an average across a population of synthetic nanocarriers. In one embodiment, the load on average across the synthetic nanocarriers is between 0.1% and 15%. In another embodiment, the load is between 0.1% and 10%. In a further embodiment, the load is between 1% and 15%. In yet a further embodiment, the load is between 5% and 15%. In still a further embodiment, the load is between 7% and 12%. In still a further embodiment, the load is between 8% and 12%. In still another embodiment, the load is between 7% and 10%. In still another embodiment, the load is between 8% and 10%. In yet a further embodiment, the load is 5%, 6%, 7%, 8%, 9%, 10%, 11%, 12%, 13%, 14%, or 15% on average across the population of synthetic nanocarriers. In any one of the methods, compositions or kits provided herein, the load of the immunosuppressant, such as rapamycin, may be any one of the loads provided herein.

The rapamycin (or other immunosuppressant) load of the nanocarrier in suspension can be calculated by dividing the rapamycin content of the nanocarrier as determined by HPLC analysis of the test article by the nanocarrier mass. The total polymer content is measured either by gravimetric yield of the dry nanocarrier mass or by the determination of the nanocarrier solution total organic content following pharmacopeia methods and corrected for PVA content.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheroidal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is equal to or greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 µm. Preferably, a minimum dimension of at least 75%, preferably at least 80%, more preferably at least 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of synthetic nanocarriers may vary depending on the embodiment. For instance, aspect ratios of the maximum to minimum dimensions of the synthetic nanocarriers may vary from 1:1 to 1,000,000:1, preferably from 1:1 to 100,000:1, more preferably from 1:1 to 10,000:1, more preferably from 1:1 to 1000:1, still more preferably from 1:1 to 100:1, and yet more preferably from 1:1 to 10:1.

Preferably, a maximum dimension of at least 75%, preferably at least 80%, more preferably at least 90%, of the synthetic nanocarriers in a sample, based on the total number of synthetic nanocarriers in the sample is equal to or less than 3 µm, more preferably equal to or less than 2 µm, more preferably equal to or less than 1 µm, more preferably equal to or less than 800 nm, more preferably equal to or less than 600 nm, and more preferably still equal to or less than 500 nm. In preferred embodiments, a minimum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120 nm, more preferably equal to or greater than 130 nm, more preferably equal to or greater than 140 nm, and more preferably still equal to or greater than 150 nm.

Measurement of synthetic nanocarrier dimensions (e.g., effective diameter) may be obtained, in some embodiments, by suspending the synthetic nanocarriers in a liquid (usually aqueous) media and using dynamic light scattering (DLS) (e.g., using a Brookhaven ZetaPALS instrument). For example, a suspension of synthetic nanocarriers can be diluted from an aqueous buffer into purified water to achieve a final synthetic nanocarrier suspension concentration of approximately 0.01 to 0.5 mg/mL. The diluted suspension may be prepared directly inside, or transferred to, a suitable cuvette for DLS analysis. The cuvette may then be placed in the DLS, allowed to equilibrate to the controlled temperature, and then scanned for sufficient time to acquire a stable and reproducible distribution based on appropriate inputs for viscosity of the medium and refractive indicies of the sample. The effective diameter, or mean of the distribution, is then reported. Determining the effective sizes of high aspect ratio, or non-spheroidal, synthetic nanocarriers may require augmentative techniques, such as electron microscopy, to obtain more accurate measurements. "Dimension" or "size" or "diameter" of synthetic nanocarriers means the mean of a particle size distribution, for example, obtained using dynamic light scattering.

"Pegylated uricase" refers to any uricase that is attached to one or more PEG (poly(ethylene glycol), poly (ethylene oxide) or poly (oxyethylene)) molecules (i.e., a poly(ethylene glycol), poly (ethylene oxide) or poly (oxyethylene) polymer or unit thereof). Preferably in some embodiments, the one or more PEG molecules are poly(ethylene glycol) molecules. The terms "pegylated" or "pegylation" refer to the conjugated form or the act of conjugating to the uricase, respectively. Such a modified uricase is referred to as pegylated uricase. Pegylated uricases include, but are not limited to pegsiticase (i.e., pegadricase) and pegloticase (KRYSTEXXA®).

"Pharmaceutically acceptable excipient" or "pharmaceutically acceptable carrier" means a pharmacologically inactive material used together with a pharmacologically active material to formulate the compositions. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers. Any one of the compositions provided herein may include a pharmaceutically acceptable excipient or carrier.

"Rapalog" refers to rapamycin and molecules that are structurally related to (an analog of) rapamycin (sirolimus), and are preferably hydrophobic. Examples of rapalogs include, without limitation, temsirolimus (CCI-779), deforolimus, everolimus (RAD001), ridaforolimus (AP-23573), zotarolimus (ABT-578). Additional examples of rapalogs may be found, for example, in WO Publication WO 1998/002441 and U.S. Pat. No. 8,455,510, the disclosure of such rapalogs are incorporated herein by reference in its entirety. In any one of the methods or compositions or kits provided herein, the immunosuppressant may be a rapalog.

"Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like. In any one of the methods, compositions and kits provided herein, the subject is human. In any one of the methods, compositions and kits provided herein, the subject is any one of the subjects provided herein, such as one that in is need thereof, such as in need of treatment with an uricase.

"Synthetic nanocarrier(s)" means a discrete object that is not found in nature, and that possesses at least one dimension that is less than or equal to 5 microns in size. Synthetic nanocarriers may be a variety of different shapes, including but not limited to spheroidal, cuboidal, pyramidal, oblong, cylindrical, toroidal, and the like. Synthetic nanocarriers comprise one or more surfaces.

A synthetic nanocarrier can be, but is not limited to, one or a plurality of lipid-based nanoparticles (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptide or protein-based particles (also referred to herein as protein particles, i.e., particles where the majority of the material that makes up their structure are peptides or proteins) (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, oblong, cylindrical, toroidal, and the like. Examples of synthetic nanocarriers include (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al., (6) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010), and (7) those of Look et al., Nanogel-based delivery of mycophenolic acid ameliorates systemic lupus erythematosus in mice" J. Clinical Investigation 123 (4):1741-1749(2013).

Synthetic nanocarriers may have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In an embodiment, synthetic nanocarriers that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers exclude virus-like particles. In embodiments, synthetic nanocarriers may possess an aspect ratio greater than 1:1, 1:1.2, 1:1.5, 1:2, 1:3, 1:5, 1:7, or greater than 1:10.

"Treating" refers to the administration of one or more therapeutics with the expectation that the subject may have a resulting benefit due to the administration. The treating may also result in the prevention of a condition as provided herein and, therefore, treating includes prophylactic treatment. When used prophylactically, the subject is one in which a clinician expects that there is a likelihood for the development of a condition or other undesired response as provided herein. In some embodiments, a subject that is expected to have a gout flare is one in which a clinician believes there is a likelihood that a gout flare will occur. Treating may be direct or indirect, such as by inducing or directing another subject, including another clinician or the subject itself, to treat the subject.

"Weight %" or "% by weight" refers to the ratio of one weight to another weight times 100. For example, the weight % can be the ratio of the weight of one component to another times 100 or the ratio of the weight of one component to a total weight of more than one component times 100. Generally, the weight % is measured as an average across a population of synthetic nanocarriers or an average across the synthetic nanocarriers in a composition or suspension.

C. Methods and Related Compositions

As mentioned elsewhere herein, it has been demonstrated that the compositions and methods provided herein are substantially more efficacious at reducing serum uric acid levels as well as reducing the frequency of gout flares than currently available treatments.

Uricase and Pegylated Uricase

The methods and compositions and kits described herein involve compositions comprising uricase. Uricase is generally thought to catalyze the conversion of uric acid to allantoin, which is soluble and may be excreted. Uricase generally is an enzyme endogenous to all mammals, except for humans and certain primates. The gene encoding the uricase enyzme may be obtained from any source known in the art, including mammalian and microbial sources as well as by recombinant and synthetic technologies. As will be evident to one of ordinary skill in the art, a gene may be obtained from a source and recombinantly (or transgenically) expressed and produced in another organism using standard methods. See Erlich, H A, (Ed.) (1989) PCR Technology. Principles and Applications for DNA Amplification. New York: Stockton Press; Sambrook, J, et al., (1989) Molecular Cloning. A Laboratory Manual, Second Edition. Cold Spring Harbor, N.Y.: Cold Spring Harbor Laboratory Press. For example, U.S. Pat. No. 5,700,674 describes recombinant production of uricase in *E. coli* cells. In some embodiments, the enzyme is produced by fermentation in *E. coli*.

In some embodiments, the gene encoding the uricase, or a portion thereof, is obtained from a mammal, for example a pig, bovine, sheep, goat, baboon, monkey mouse, rabbit, or domestic animal. In some embodiments, the gene encoding the uricase, or a portion thereof, is obtained from a microorganism, such as a bacteria or fungi (including yeast). In some embodiments, the gene encoding the uricase is obtained from a bacterial source, such as bacterium belonging to *Streptomyces* spp., *Bacillus* spp., or *E. coli*. In some embodiments, the gene encoding the uricase is obtained from a fungal (including yeast) source, such as *Candida* (e.g., *Candida utilis*), *Anthrobacter* (e.g., *Anthrobacter globiformis*), *Saccharomyces, Schizosaccaromyces, Emericella, Aspergillus* (e.g., *Aspergillus flavus*), and *Neurospora* spp. In some embodiments, the uricase is derived from *Candida utilis*. In some embodiments, the uricase is that of pegsiticase (3SBio as described in U.S. Pat. No. 6,913,915, and such uricase and description thereof is incorporated herein by reference). In some embodiments, the uricase is derived from *Aspergillus flavus*. In some embodiments, the uricase is rasburicase (ELITEK®; FASTURTEC®, from Sanofi Genzyme).

In some embodiments, the uricase is chimeric uricase, in which portions of the gene encoding the uricase are obtained from different sources. For example, a portion of the gene encoding the chimeric uricase may be obtained from one organism and one or more other portions of the gene encoding the chimeric uricase may be obtained from another organism. In some embodiments, a portion of the gene encoding the chimeric uricase is obtained from a pig and another portion of the gene encoding the chimeric uricase is obtained from a baboon. In some embodiments, the chimeric uricase is that of pegloticase/KRYSTEXXA®.

Also within the scope of the present invention are variant uricases, which may include one or more mutations (substitutions, insertions, deletions). Mutations may be made in the nucleotide sequence encoding the uricase protein, which may or may not result in an amino acid mutation. In general, mutations may be made, for example, to enhance production of the protein, turnover/half-life of the protein or mRNA encoding the protein, modulate (enhance or reduce) the enzymatic activity of the uricase.

In other embodiments, the gene encoding the uricase is obtained from a plant or invertebrate source, such as *Drosophila* or *C. elegans*.

Any of the uricase proteins described herein may be pegylated. Uricase may be covalently bonded to PEG via a biocompatible linking group, using methods known in the art, as described, for example, by Park et al, Anticancer Res., 1:373-376 (1981); and Zaplipsky and Lee, Polyethylene Glycol Chemistry: Biotechnical and Biomedical Applications, J. M. Harris, ed., Plenum Press, New York, Chapter 21 (1992). The linking group used to covalently attach PEG to uricase may be any biocompatible linking group, meaning the linking group non-toxic and may be utilized in vitro or in vivo without causing adverse effects. Alternatively, the PEG may be directly conjugated to the uricase, such as directly to a lysine residue of uricase.

Uricase may be pegylated at many different amino acid resides of the uricase protein. The number of PEG molecules and/or residue to which the PEG is conjugated may affect the activity of the uricase. In some embodiments, the pegylated uricase comprises at least one PEG molecule. In some embodiments, the pegylated uricase comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more PEG molecules on average per uricase protein. In some embodiments, the pegylated uricase comprises about 20-25 PEG molecules per uricase protein.

On average, PEG has a molecular weight between 5 kDa to 100 kDa. Both the molecular weight (size) of the PEG used as well as the number of PEG molecules used to pegylate the uricase may be varied. In some embodiment the average molecular weight of the PEG is between 5 kDa to 100 kDa, 5 kDa to 75 kDa, 5 kDa to 50 kDa, 5 kDa to 30 kDa, 5 kDa to 20 kDa, 5 kDa to 10 kDa, 10 kDa to 75 kDa, 10 kDa to 50 kDa, 10 kDa to 30 kDa, 5 kDa to 30 kDa, 15 kDa to 50 kDa, 15 kDa to 30 kDa, 15 kDa to 25 kDa, 20 kDa to 75 kDa, 30 kDa to 80 kDa, 30 kDa to 70 kDa, or 30 kDa to 50 kDa. In some embodiments, the molecular weight of the PEG is about 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 21 kDa, 22 kDa, 23 kDa, 24 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, or 100 kDa. In general, the PEG is referred to based on the molecular weight of the PEG. For example, PEG-20 refers to PEG molecules with a molecular weight of 20 kDa, and PEG-5 refers to PEG molecules with a molecular weight of 5 kDa. In some embodiments, the uricase is pegylated with PEG molecules having a molecule weight of 20 kDa (PEG-20).

Pegylated uricases include, without limitation, pegsiticase (i.e., pegadricase) (available from 3Sbio, and as described in U.S. Pat. No. 6,913,915, and such pegylated uricase and description thereof is incorporated herein by reference) and pegloticase/KRYSTEXXA® (Horizon Pharmaceuticals).

Preferably, in some embodiments of any one of the methods or compositions or kits provided herein, the pegylated uricase is pegsiticase (i.e., pegadricase), a recombinant uricase conjugated to multiple 20 kDa molecular weight poly (ethylene glycol) molecules. The uricase component of pegsiticase can be cloned from the yeast *Candida utilis* and expressed in *E. coli* for production.

The uric acid catalysis activity of uricase, including pegylated uricase, can be assessed using methods known in the art or as otherwise provided herein.

Synthetic Nanocarriers

A variety of synthetic nanocarriers can be used. In some embodiments, synthetic nanocarriers are spheres or spheroids. In some embodiments, synthetic nanocarriers are flat or plate-shaped. In some embodiments, synthetic nanocarriers are cubes or cubic. In some embodiments, synthetic nanocarriers are ovals or ellipses. In some embodiments, synthetic nanocarriers are cylinders, cones, or pyramids.

In some embodiments, it is desirable to use a population of synthetic nanocarriers that is relatively uniform in terms of size or shape so that each synthetic nanocarrier has similar properties. For example, at least 80%, at least 90%, or at least 95% of the synthetic nanocarriers, based on the total number of synthetic nanocarriers, may have a minimum dimension or maximum dimension that falls within 5%, 10%, or 20% of the average diameter or average dimension of the synthetic nanocarriers.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g. a polymeric core) and the shell is a second layer (e.g. a lipid bilayer or monolayer). Synthetic nanocarriers may comprise a plurality of different layers.

In preferred embodiments, the synthetic nanocarriers comprise a polymer as provided herein. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

The synthetic nanocarriers as provided herein, preferably, comprise hydrophobic polyesters. Such polyesters can include copolymers comprising lactic acid and glycolic acid units, such as poly(lactic acid-co-glycolic acid) and poly (lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolyesters, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, the polyester may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

The synthetic nanocarriers may comprise one or more non-polyester polymers or units thereof that are also hydrophobic and/or polymers or units thereof that are not hydrophobic. In some embodiments, it is preferred that overall the synthetic nanocarrier comprises a hydrophobic polyester and, in some embodiments, is itself hydrophobic.

The synthetic nanocarriers may comprise one or more polymers that are a non-methoxy-terminated, pluronic polymer, or a unit thereof. "Non-methoxy-terminated polymer" means a polymer that has at least one terminus that ends with a moiety other than methoxy. In some embodiments, the polymer has at least two termini that ends with a moiety other than methoxy. In other embodiments, the polymer has no termini that ends with methoxy. "Non-methoxy-terminated, pluronic polymer" means a polymer other than a linear pluronic polymer with methoxy at both termini.

The synthetic nanocarriers may comprise, in some embodiments, polyhydroxyalkanoates, polyamides, polyethers, polyolefins, polyacrylates, polycarbonates, polystyrene, silicones, fluoropolymers, or a unit thereof. Further examples of polymers that may be comprised in the synthetic nanocarriers provided herein include polycarbonate, polyamide, or polyether, or unit thereof. In other embodiments, the polymers of the synthetic nanocarriers may comprise poly(ethylene glycol) (PEG), polypropylene glycol, or unit thereof.

In some embodiments, it is preferred that the synthetic nanocarriers comprise polymer that is biodegradable. Therefore, in such embodiments, the polymers of the synthetic nanocarriers may include a polyether, such as poly(ethylene glycol) or polypropylene glycol or unit thereof. Additionally, the polymer may comprise a block-co-polymer of a polyether and a biodegradable polymer such that the polymer is biodegradable. In other embodiments, the polymer does not solely comprise a polyether or unit thereof, such as poly(ethylene glycol) or polypropylene glycol or unit thereof.

In some embodiments, polymers in accordance with the present invention include polymers which have been approved for use in humans by the U.S. Food and Drug Administration (FDA) under 21 C.F.R. § 177.2600.

Other examples of polymers suitable for use in synthetic nanocarriers include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly(β-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

Still other examples of polymers that may be included in the synthetic nanocarriers include acrylic polymers, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers.

In some embodiments, the polymers of a synthetic nanocarrier associate to form a polymeric matrix. A wide variety of polymers and methods for forming polymeric matrices therefrom are known conventionally. In some embodiments, a synthetic nanocarrier comprising a hydrophobic polyester has a hydrophobic environment within the synthetic nanocarrier.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that the synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention provided they meet the desired criteria.

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

Synthetic nanocarriers may be prepared using a wide variety of methods known in the art. For example, synthetic nanocarriers can be formed by methods such as nanoprecipitation, flow focusing using fluidic channels, spray drying, single and double emulsion solvent evaporation, solvent extraction, phase separation, milling (including cryomilling), supercritical fluid (such as supercritical carbon dioxide) processing, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

Immunosuppressants may be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010). Other methods suitable for encapsulating materials into synthetic nanocarriers may be used, including without limitation methods disclosed in U.S. Pat. No. 6,632,671 to Unger issued Oct. 14, 2003.

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be included in the synthetic nanocarriers and/or the composition of the carrier matrix.

If synthetic nanocarriers prepared by any of the above methods have a size range outside of the desired range, such synthetic nanocarriers can be sized, for example, using a sieve.

Preferably, in some embodiments of any one of the methods or compositions or kits provided herein, the synthetic nanocarriers are those that comprise synthetic nanocarriers composed of PLA and PLA-PEG. PLA is part of the broader poly(lactic co glycolic acid), or PLGA, family of biodegradable polymers that have more than 30 years of commercial use and are formulation components in a number of approved products. Polyethylene glycol, or PEG, has been widely studied in clinical trials and is also a formulation component in many approved biologic products.

As examples, the synthetic nanocarriers comprising rapamycin can be those produced or obtainable by one of the following methods:

1) PLA with an inherent viscosity of 0.41 dL/g is purchased from Evonik Industries (Rellinghauser Straße 1-11 45128 Essen, Germany), product code Resomer Select 100 DL 4A. PLA-PEG-OMe block co-polymer with a methyl ether terminated PEG block of approximately 5,000 Da and an overall inherent viscosity of 0.50 DL/g is purchased from Evonik Industries (Rellinghauser Straße 1-11 45128 Essen, Germany), product code Resomer Select 100 DL mPEG 5000 (15 wt % PEG). Rapamycin is purchased from Concord Biotech Limited (1482-1486 Trasad Road, Dholka 382225, Ahmedabad India), product code SIROLIMUS. EMPROVE® Polyvinyl Alcohol 4-88, USP (85-89% hydrolyzed, viscosity of 3.4-4.6 mPa·s) is purchased from MilliporeSigma (EMD Millipore, 290 Concord Road Billerica, Mass. 01821), product code 1.41350. Dulbecco's phosphate buffered saline 1×(DPBS) is purchased from Lonza (Muenchensteinerstrasse 38, CH-4002 Basel, Switzerland), product code 17-512Q. Sorbitan monopalmitate is purchased from Croda International (300-A Columbus Circle, Edison, N.J. 08837), product code SPAN 40. Solutions are prepared as follows. Solution 1 is prepared by dissolving PLA at 150 mg/mL and PLA-PEG-Ome at 50 mg/mL in dichloromethane. Solution 2 is prepared by dissolving rapamycin at 100 mg/mL in dichloromethane. Solution 3 is prepared by dissolving SPAN 40 at 50 mg/mL in dichloromethane. Solution 4 is prepared by dissolving PVA at 75 mg/mL in 100 mM phosphate buffer pH 8. O/W emulsions are prepared by adding Solution 1 (0.50 mL), Solution 2 (0.12 mL), Solution 3 (0.10 mL), and dichloromethane (0.28 mL), in a thick walled glass pressure tube. The combined organic phase solutions are then mixed by repeat pipetting. To this mixture, Solution 4 (3 mL), is added. The pressure tube is then vortex mixed for 10 seconds. Next, the crude emulsion is homogenized by sonication at 30% amplitude for 1 minute using a Branson Digital Sonifier 250 with a ⅛" tapered tip, and the pressure tube immersed in an ice water bath. The emulsion is then added to a 50 mL beaker containing DPBS (30 mL). This is stirred at room temperature for 2 hours to allow the dichloromethane to evaporate and for the nanocarriers to form. A portion of the nanocarriers is washed by transferring the nanocarrier suspension to a centrifuge tube and centrifuging at 75,600×g at 4° C. for 50 minutes, removing the supernatant, and re-suspended the pellet in DPBS containing 0.25% w/v PVA. The wash procedure is repeated and the pellet is re-suspended in DPBS containing 0.25% w/v PVA to achieve a nanocarrier suspension having a nominal concentration of 10 mg/mL on a polymer basis. The nanocarrier suspension is then filtered using a 0.22 µm PES membrane syringe filter from MilliporeSigma (EMD Millipore, 290 Concord Rd. Billerica Mass., product code SLGP033RB). The filtered nanocarrier suspension is stored at −20° C.

2) PLA with an inherent viscosity of 0.41 dL/g is purchased from Evonik Industries (Rellinghauser Straße 1-11 45128 Essen, Germany), product code Resomer Select 100 DL 4A. PLA-PEG-OMe block co-polymer with a methyl ether terminated PEG block of approximately 5,000 Da and an overall inherent viscosity of 0.50 DL/g is purchased from Evonik Industries (Rellinghauser Straße 1-11 45128 Essen, Germany), product code Resomer Select 100 DL mPEG 5000 (15 wt % PEG). Rapamycin is purchased from Concord Biotech Limited (1482-1486 Trasad Road, Dholka 382225, Ahmedabad India), product code SIROLIMUS. Sorbitan monopalmitate is purchased from Sigma-Aldrich (3050 Spruce St., St. Louis, Mo. 63103), product code 388920. EMPROVE® Polyvinyl Alcohol (PVA) 4-88, USP (85-89% hydrolyzed, viscosity of 3.4-4.6 mPa·s) is purchased from MilliporeSigma (EMD Millipore, 290 Concord Road Billerica, Mass. 01821), product code 1.41350. Dulbecco's phosphate buffered saline 1×(DPBS) is purchased from Lonza (Muenchensteinerstrasse 38, CH-4002 Basel, Switzerland), product code 17-512Q. Solutions are prepared as follows: Solution 1: A polymer, rapamycin, and sorbitan monopalmitate mixture is prepared by dissolving PLA at 37.5 mg/mL, PLA-PEG-Ome at 12.5 mg/mL, rapamycin at 8 mg/mL, and sorbitan monopalmitate at 2.5 in dichloromethane. Solution 2: Polyvinyl alcohol is prepared at 50 mg/mL in 100 mM pH 8 phosphate buffer. An O/W emulsion is prepared by combining Solution 1 (1.0 mL) and Solution 2 (3 mL) in a small glass pressure tube, and vortex mixed for 10 seconds. The formulation is then homogenized by sonication at 30% amplitude for 1 minute using a Branson Digital Sonifier 250 with a ⅛" tapered tip, with the pressure tube immersed in an ice water bath. The emulsion is then added to a 50 mL beaker containing DPBS (15 mL), and covered with aluminum foil. A second O/W emulsion is prepared using the same materials and method as above and then added to the same beaker using a fresh aliquot of DPBS (15 mL). The combined emulsion is then left uncovered and stirred at room temperature for 2 hours to allow the dichloromethane to evaporate and for the nanocarriers to form. A portion of the nanocarriers is washed by transferring the nanocarrier suspension to a centrifuge tube and centrifuging at 75,600×g and 4° C. for 50 minutes, removing the supernatant, and re-suspending the pellet in DPBS containing 0.25% w/v PVA. The wash procedure is repeated and then the pellet re-suspended in DPBS containing 0.25% w/v PVA to achieve a nanocarrier suspension having a nominal concentration of 10 mg/mL on a polymer basis. The nanocarrier suspension is then filtered using a 0.22 µm PES membrane syringe filter from MilliporeSigma (EMD Millipore, 290 Concord Rd. Billerica Mass., product code SLGP033RB). The filtered nanocarrier suspension is then stored at −20° C.

Immunosuppressants

Any immunosuppressant as provided herein can be used in any one of the methods or compositions provided and can be, in some embodiments, attached to synthetic nanocarriers. Immunosuppressants include, but are not limited to, mTOR inhibitors. Examples of mTOR inhibitors include rapamycin and rapalogs (e.g., CCL-779, RAD001, AP23573, C20-methallylrapamycin (C20-Marap), C16-(S)-butylsulfonamidorapamycin (C16-BSrap), C16-(S)-3-methylindolerapamycin (C16-iRap) (Bayle et al. Chemistry & Biology 2006, 13:99-107)), AZD8055, BEZ235 (NVP-BEZ235), chrysophanic acid (chrysophanol), deforolimus (MK-8669), everolimus (RAD0001), KU-0063794, PI-103, PP242, temsirolimus, and WYE-354 (available from Selleck, Houston, Tex., USA).

Preferably, in some embodiments of any one of the methods or compositions or kits provided herein, the immunosuppressant is rapamycin. In some of such embodiments, the rapamycin is preferably encapsulated in the synthetic nanocarriers. Rapamycin is the active ingredient of Rapamune, an immunosuppressant which has extensive prior use in humans and is currently FDA approved for prophylaxis of organ rejection in kidney transplant patients aged 13 or older.

When coupled to a synthetic nanocarrier, the amount of the immunosuppressant coupled to the synthetic nanocarrier based on the total dry recipe weight of materials in an entire synthetic nanocarrier (weight/weight), is as described elsewhere herein. Preferably, in some embodiments of any one of the methods or compositions or kits provided herein, the load of the immunosuppressant, such as rapamycin or rapalog, is between 7% and 12% or 8% and 12% by weight.

Anti-Inflammatory Therapeutics

Anti-inflammatory therapeutics (i.e., any therapeutic that can act to reduce inflammation). Anti-inflammatory therapeutics include, but are not limited to, corticosteroids or derivatives of cortisol (hydrocortisone). Corticosteroids include, but are not limited to, glucocorticoids and mineralocorticoids. Still other examples of corticosteroids include, but are not limited to, those that are natural (e.g., 11-Dehydrocorticosterone (11-oxocorticosterone, 17-deoxycortisone)=21-hydroxypregn-4-ene-3,11,20-trione; 11-Deoxycorticosterone (deoxycortone, desoxycortone; 21-hydroxyprogesterone)=21-hydroxypregn-4-ene-3,20-dione; 11-Deoxycortisol (cortodoxone, cortexolone)=17α,21-dihydroxypregn-4-ene-3,20-dione; 11-Ketoprogesterone (11-oxoprogesterone; Ketogestin)=pregn-4-ene-3,11,20-trione; 11β-Hydroxypregnenolone=3β,11β-dihydroxypregn-5-en-20-one; 11β-Hydroxyprogesterone (21-deoxycorticosterone)=11β-hydroxypregn-4-ene-3,20-dione; 11β,17α,21-Trihydroxypregnenolone=3β,11β,17α,21-tetrahydroxypregn-5-en-20-one; 17α,21-Dihydroxypregnenolone=3β,17α,21-trihydroxypregn-5-en-20-one; 17α-Hydroxypregnenolone=3β,17α-dihydroxypregn-5-en-20-one; 17α-Hydroxyprogesterone=17α-hydroxypregn-4-ene-3,11,20-trione; 18-Hydroxy-11-deoxycorticosterone=18,21-dihydroxypregn-4-ene-3,20-dione; 18-Hydroxycorticosterone=11β,18,21-trihydroxypregn-4-ene-3,20-dione; 18-Hydroxyprogesterone=18-hydroxypregn-4-ene-3,20-dione; 21-Deoxycortisol=11β,17α-dihydroxypregn-4-ene-3,20-dione; 21-Deoxycortisone=17α-hydroxypregn-4-ene-3,11,20-trione; 21-Hydroxypregnenolone (prebediolone)=3β,21-dihydroxypregn-5-en-20-one; Aldosterone=11β,21-dihydroxypregn-4-ene-3,18,20-trione; Corticosterone (17-deoxycortisol)=11β,21-dihydroxypregn-4-ene-3,20-dione; Cortisol (hydrocortisone)=11β,17α,21-trihydroxypregn-4-ene-3,20-dione; Cortisone=17α,21-dihydroxypregn-4-ene-3,11,20-trione; Pregnenolone=pregn-5-en-3β-ol-20-one; and Progesterone=pregn-4-ene-3,20-dione); those that are synthetic, such as progesterone-type (e.g., Flugestone (flurogestone)=9α-fluoro-11β,17α-dihydroxypregn-4-ene-3,20-dione; Fluorometholone=6α-methyl-9α-fluoro-11β,17α-dihydroxypregna-1,4-diene-3,20-dione; Medrysone (hydroxymethylprogesterone)=6α-methyl-11β-hydroxypregn-4-ene-3,20-dione; and Prebediolone acetate (21-acetoxypregnenolone)=3β,21-dihydroxypregn-5-en-20-one 21-acetate) and progesterone derivative progestins (e.g., chlormadinone acetate, cyproterone acetate, medrogestone, medroxyprogesterone acetate, megestrol acetate, and segesterone acetate); hydrocortisone-type (e.g., Chloroprednisone=6α-chloro-17α,21-dihydroxypregna-1,4-diene-3,11,20-trione; Cloprednol=6-chloro-11β,17α,21-trihydroxypregna-1,4,6-triene-3,20-dione; Difluprednate=6α,9α-difluoro-11β,17α,21-trihydroxy-pregna-1,4-diene-3,20-dione 17α-butyrate 21-acetate; Fludrocortisone=9α-fluoro-11β,17α,21-trihydroxypregn-4-ene-3,20-dione; Fluocinolone=6α,9α-difluoro-11β,16α,17α,21-tetrahydroxypregna-1,4-diene-3,20-dione; Fluperolone=9α-fluoro-11β,17α,21-trihydroxy-21-methyl-pregna-1,4-diene-3,20-dione; Fluprednisolone=6α-fluoro-11β,17α,21-trihydroxypregna-1,4-diene-3,20-dione; Loteprednol=11β,17α,dihydroxy-21-oxa-21-chloromethyl-pregna-1,4-diene-3,20-dione; Methylprednisolone=6α-methyl-11β,17α,21-trihydroxypregna-1,4-diene-3,20-dione; Prednicarbate=11β,17α,21-trihydroxypregna-1,4-diene-3,20-dione 17α-ethylcarbonate 21-propionate; Prednisolone=11β,17α,21-trihydroxypregna-1,4-diene-3,20-dione; Prednisone=17α,21-dihydroxypregna-1,4-diene-3,11,20-trione; Tixocortol=11β,17α-dihydroxy-21-sulfanyl-pregn-4-ene-3,20-dione; and Triamcinolone=9α-fluoro-11β,16α,17α,21-tetrahydroxypregna-1,4-diene-3,20-dione); methasone-type (16-methylated) (e.g., Methasone; Alclometasone=7α-chloro-11β,17α,21-trihydroxy-16α-methylpregna-1,4-diene-3,20-dione; Beclometasone=9α-chloro-11β,17α,21-trihydroxy-16β-methylpregna-1,4-diene-3,20-dione; Betamethasone=9α-fluoro-11β,17α,21-trihydroxy-16γ-methylpregna-1,4-diene-3,20-dione; Clobetasol=9α-fluoro-11β,17α-dihydroxy-16β-methyl-21-chloropregna-1,4-diene-3,20-dione; Clobetasone=9α-fluoro-16β-methyl-17α-hydroxy-21-chloropregna-1,4-diene-3,11,20-trione; Clocortolone=6α-fluoro-9α-chloro-11β,21-dihydroxy-16α-methylpregna-1,4-diene-3,20-dione; Desoximetasone=9α-fluoro-11β,21-dihydroxy-16α-methylpregna-1,4-diene-3,20-dione; Dexamethasone=9α-fluoro-11β,17α,21-trihydroxy-16α-methylpregna-1,4-diene-3,20-dione; Diflorasone=6α,9α-difluoro-11β,17α,21-trihydroxy-16β-methylpregna-1,4-diene-3,20-dione; Difluocortolone=6α,9α-difluoro-11β,21-dihydroxy-16α-methylpregna-1,4-diene-3,20-dione; Fluclorolone=6α-fluoro-9α,11β-dichloro-16α,17α,21-trihydroxypregna-1,4-dien-3,20-dione; Flumetasone=6α,9α-difluoro-11β,17α,21-trihydroxy-16α-methylpregna-1,4-diene-3,20-dione; Fluocortin=6α-fluoro-11β,21-dihydroxy-16α-methyl-pregna-1,4-diene-3,20,21-trione; Fluocortolone=6α-fluoro-11β,21-dihydroxy-16α-methylpregna-1,4-diene-3,20-dione; Fluprednidene=9α-fluoro-11β,17α,21-trihydroxy-16-methylenepregna-1,4-diene-3,20-dione; Fluticasone=6α,9α-difluoro-11β,17α-dihydroxy-16α-methyl-21-thia-21-fluoromethylpregna-1,4-dien-3,20-dione; Fluticasone furoate=6α,9α-difluoro-11β,17α-dihydroxy-16α-methyl-21-thia-21-fluoromethylpregna-1,4-dien-3,20-dione 17α-(2-furoate); Halometasone=2-chloro-6α,9α-difluoro-11β,17α,21-trihydroxy-16α-methylpregna-1,4-diene-3,20-dione; Meprednisone=16β-methyl-17α,21-dihydroxypregna-1,4-diene-3,11,20-trione; Mometasone=9α,21-dichloro-11β,17α-dihydroxy-16α-methylpregna-1,4-diene-3,20-dione; Mometasone furoate=9α,21-dichloro-11β,17α-dihydroxy-16α-methylpregna-1,4-diene-3,20-dione 17α-(2-furoate); Paramethasone=6α-fluoro-11β,17α,21-trihydroxy-16α-methylpregna-1,4-diene-3,20-dione; Prednylidene=11β,17α,21-trihydroxy-16-methylenepregna-1,4-diene-3,20-dione; Rimexolone=11β-hydroxy-16α,17α,21-trimethylpregna-1,4-dien-3,20-dione; and Ulobetasol (halobetasol)=6α,9α-difluoro-11β,17α-dihydroxy-16β-methyl-21-chloropregna-1,4-diene-3,20-dione); Acetonides and related (e.g., Amcinonide=9α-fluoro-11β,16α,17α,21-tetrahydroxypregna-1,4-diene-3,20-dione cyclic 16α,17α-acetal with cyclopentanone, 21-acetate; Budesonide=11β,16α,17α,21-tetrahydroxypregna-1,4-diene-3,20-dione cyclic 16α,17α-acetal with butyraldehyde; Ciclesonide=11β,16α,17α,21-tetrahydroxypregna-1,4-diene-3,20-dione cyclic 16α,17α-acetal with (R)-cyclohexanecarboxaldehyde, 21-isobutyrate; Deflazacort=11β,21-dihydroxy-2'-methyl-5'H-pregna-1,4-dieno[17,16-d]oxazole-3,20-dione 21-acetate; Desonide=11β,16α,17α,21-tetrahydroxypregna-1,4-diene-3,20-dione cyclic 16α,17α-acetal with acetone; Formocortal (fluoroformylone)=3-(2-chloroethoxy)-9α-fluoro-11β,16α,17α,21-tetrahydroxy-20-oxopregna-3,5-diene-6-carboxaldehyde cyclic 16α,17α-acetal with acetone, 21-acetate; Fluclorolone acetonide (flucloronide)=6α-fluoro-9α,11β-dichloro-16α,17α,21-trihydroxypregna-1,4-dien-3,20-dione cyclic 16α,17α-acetal with acetone; Fludroxycortide (flurandrenolone, flurandrenolide)=6α-fluoro-11β,16α,17α,21-tetrahydroxypregn-4-ene-3,20-dione cyclic 16α,17α-acetal with acetone; Flunisolide=6α-fluoro-11β,16α,17α,21-tetrahydroxypregna-1,4-diene-3,20-dione cyclic 16α,17α-acetal with acetone; Fluocinolone acetonide=6α,9α-difluoro-11β,16α,17α,21-tetrahydroxypregna-1,4-diene-3,20-dione cyclic 16α,17α-acetal with acetone; Fluocinonide=6α,9α-difluoro-11β,16α,17α,21-tetrahydroxypregna-1,4-diene-3,20-dione cyclic 16α,17α-acetal with acetone, 21-acetate; Halcinonide=9α-fluoro-11β,16α,17α-trihydroxy-21-chloropregn-4-ene-3,20-dione cyclic 16α,17α-acetal with acetone; and Triamcinolone acetonide=9α-fluoro-11β,16α,17α,21-tetrahydroxypregna-1,4-diene-3,20-dione cyclic 16α,17α-acetal with acetone); and still others (e.g., Cortivazol=6,16α-dimethyl-11β,17α,21-trihydroxy-2'-phenyl[3,2-c]pyrazolopregna-4,6-dien-20-one 21-acetate; and RU-28362=6-methyl-11β,17β-dihydroxy-17α-(1-propynyl)androsta-1,4,6-trien-3-one).

Corticosteroids, particularly glycocorticoids, have anti-inflammatory and immunosuppressive effects that may be effective in managing symptoms, including pain and inflammation associated with gout, gout flare, and/or conditions associated with gout. Administration of corticosteroids may also aid in reducing hypersensitivity reactions associated with one or more additional therapies, for example uricase replacement therapy. Still other non-limiting examples of corticosteroids, include prednisone, prednisolone, Medrol, and methylprednisolone.

Infusion Reaction Therapeutic

Infusion reaction therapeutics (i.e., any therapeutic that can be beneficial in reducing or preventing infusion reactions) can also be included in the compositions and related methods provided herein. Such therapeutics can include an anti-inflammatory, such as any one of the anti-inflammatories provided herein (e.g., a corticosteroid, such as methylprednisolone, prednisone or dexamethasone). Such therapeutics can also include an antihistamine. Antihistamines are agents that can inhibit the physiological effects of histamine, and include Brompheniramine, Carbinoxamine, Chlorpheniramine, Clemastine, Diphenhydramine, Hydroxyzine, Triprolidine, Cetirizine, Desloratadine, Fexofenadine, Levocetirizine, Loratadine, etc.

Dosing

Unless otherwise specified herein, the amount (by weight) of a dose of a composition comprising pegylated uricase as well as the concentrations per vial provided herein refers to the amount or concentration of the uricase protein, respectively, not including the PEG molecules conjugated thereto or any added excipients in the composition. The actual amount of the pegylated uricase, in such instances, will be higher than the dose described due to the higher weight of the pegylated protein form. In one example, a dose of 0.4 mg/kg of a composition comprising pegylated uricase refers to a dose of 0.4 mg/kg uricase protein.

Thus, a dose of a composition comprising pegylated uricase for administration to a subject may be calculated based on the dose provided herein and the weight of the subject, according to the following equation:

(dose in mg/kg (this is of the uricase protein))×(subject weight (kg))/(concentration per mL in vial (again this is of the uricase protein))=volume to be administered As an example, the pegylated uricase may be reconstituted in sterile water to a concentration of 6 mg/mL. Thus, for this example, for a dose of 0.4 mg/kg to be administered to a subject weighing 90.7 kg (200 lbs), 6.048 mL of the reconstituted pegylated uricase composition should be administered to the subject:

(0.4 mg/kg)×(90.7 kg)/(6 mg/mL)=6.048 mL

In some embodiments, the appropriate volume of the composition comprising pegylated uricase is diluted in a pharmaceutically acceptable excipient (e.g., sterile saline solution) for, for example, intravenous infusion to a subject over a desired period of time (e.g., 60 minutes).

Similarly, unless otherwise specified herein, the amount (by weight) of a dose of a composition comprising synthetic nanocarriers comprising an immunosuppressant as well as the concentrations per vial as provided herein refers to the amount or concentration of the immunosuppressant, respectively, and not including the synthetic nanocarrier material or any added excipients or other components in the composition. The actual amount of the synthetic nanocarrier composition comprising the immunosuppressant will be higher than the dose described due to the added weight of the synthetic nanocarrier material and any added excipients or other components in the composition. In one example, a dose of 0.08 mg/kg of a composition comprising synthetic nanocarriers comprising an immunosuppressant refers to a dose of 0.08 mg/kg immunosuppressant.

Thus, a dose of a composition comprising synthetic nanocarriers comprising an immunosuppressant for administration to a subject may be calculated based on the weight of the subject, according to the following equation:

(dose in mg/kg (this is of the immunosuppressant))×(subject weight (kg))/(concentration per mL in vial (again this is of the immunosuppressant) =volume to be administered As an example, the composition comprising synthetic nanocarriers comprising an immunosuppressant is at a concentration of 2 mg/mL (again this is the concentration of the immunosuppressant). Thus, for this example, for a dose of 0.08 mg/kg to be administered to a subject weighing 90.7 kg (200 lbs), 3.6 mL of the composition should be administered to the subject:

(0.08 mg/kg)×(90.7 kg)/(2 mg/mL)=3.6 mL

The load of the immunosuppressant (e.g., rapamycin) of the synthetic nanocarriers comprising an immunosuppressant may be determined by extracting the immunosuppressant from the synthetic nanocarriers using liquid extraction compatible with both the immunosuppressant and the synthetic nanocarriers (e.g., polymers comprising the synthetic nanocarriers) and analyzing the extract by reverse phase liquid chromatography with UV detection specific for the analyte. The immunosuppressant load (content of the synthetic nanocarriers) may be accurately and precisely calculated from a calibration standard curve of a qualified reference standard prepared in conditions compatible with the chromatography and the nanoparticle extraction procedure and analyzed concomitantly.

The amount (by weight) of a dose of a composition comprising synthetic nanocarriers comprising an immunosuppressant may be calculated based on the amount (by weight) of the immunosuppressant dose, according to the following equation:

(1/load of immunosuppressant)×(dose given based on the amount of immunosuppressant)=dose of immunosuppressant given as the amount of the synthetic nanocarriers comprising the immunosuppressant As an example, the load of immunosuppressant in the synthetic nanocarriers can be about 10% and if a dose of 0.08 mg/kg of the immunosuppressant is desired, the dose given as the amount of the synthetic nanocarriers comprising the immunosuppressant is 8 mg/kg.

The amount of uricase protein present in a pegylated uricase may be determined using methods known in the art, for example colorimetry, UV absorbance or amino acid analysis. The colorimetric approach relies on a standardized kit commercially available leveraging typical dye based reactions such as those described for Bradford or bicinchoninic acid (BCA) assays. The uricase protein quantity can be accurately and precisely calculated from a calibration standard curve of a qualified protein reference standard, preferably purchased from compendial sources, and analyzed concomitantly using the same spectrophotometer. Single or multiple point calibration of a known protein of similar or different chemical properties may be run within the same assay to ensure consistency of the read out at the chosen UV absorbance. The amino acid mixture obtained from acid hydrolysis of the drug product may also be analyzed and generally provides a precise and accurate quantification. The amino acid mixture is analyzed by HPLC with either UV or fluorescence detection and using pre-chromatography or post-chromatography derivatization of the primary and secondary amines. Commercially available mixtures of common amino acids are analyzed within the same assay to build the individual amino acid calibration curves against which each amino acid is quantified. In some embodiments, the determination of the uricase protein quantity is supplemented by measuring the enzyme activity, which may be performed by measuring the decrease of an excess of uric acid monitored by UV absorbance at 595 nm. Alternatively or in addition, the uricase activity can be determined using a commercially available kit, which may involve, for example, labeling the enzymatic reaction product and measuring the response of the uricase against a calibration curve established by analyzing a known quantity of the enzyme.

Similar to the immediately above formula, the amount (by weight) of a dose of a composition comprising pegylated uricase can be calculated based on the amount (by weight) of the uricase dose, according to the following equation:

(1/(weight of uricase of a pegylated uricase/weight of the pegylated uricase))×(dose given based on the amount of uricase)=dose of pegylated uricase given as the amount of the pegylated uricase It should be understood that the amount provided herein can be an average amount based on a population of the respective molecules in a composition.

Exemplary doses of uricase for any one of the compositions or methods comprising uricase, such as pegsiticase (i.e., pegadricase), as provided herein can be 0.10 mg/kg, 0.11 mg/kg, 0.12 mg/kg, 0.13 mg/kg, 0.14 mg/kg, 0.15 mg/kg, 0.16 mg/kg, 0.17 mg/kg, 0.18 mg/kg, 0.19 mg/kg, 0.20 mg/kg, 0.21 mg/kg, 0.22 mg/kg, 0.23 mg/kg, 0.24 mg/kg, 0.25 mg/kg, 0.26 mg/kg, 0.27 mg/kg, 0.28 mg/kg, 0.29 mg/kg, 0.30 mg/kg, 0.31 mg/kg, 0.32 mg/kg, 0.34 mg/kg, 0.35 mg/kg, 0.36 mg/kg, 0.37 mg/kg, 0.38 mg/kg, 0.39 mg/kg, 0.40 mg/kg, 0.41 mg/kg, 0.42 mg/kg, 0.43 mg/kg, 0.44 mg/kg, 0.45 mg/kg, 0.46 mg/kg, 0.47 mg/kg, 0.48 mg/kg, 0.49 mg/kg, 0.50 mg/kg, 0.51 mg/kg, 0.52 mg/kg, 0.53 mg/kg, 0.54 mg/kg, 0.55 mg/kg, 0.56 mg/kg, 0.57 mg/kg, 0.58 mg/kg, 0.59 mg/kg, 0.60 mg/kg, 0.61 mg/kg, 0.62 mg/kg, 0.63 mg/kg, 0.64 mg/kg, 0.65 mg/kg, 0.66 mg/kg, 0.67 mg/kg, 0.68 mg/kg, 0.69 mg/kg, 0.70 mg/kg, 0.71 mg/kg, 0.72 mg/kg, 0.73 mg/kg, 0.74 mg/kg, 0.75 mg/kg, 0.76 mg/kg, 0.77 mg/kg, 0.78 mg/kg, 0.79 mg/kg, 0.80 mg/kg, 0.81 mg/kg, 0.82 mg/kg, 0.83 mg/kg, 0.84 mg/kg, 0.85 mg/kg, 0.86 mg/kg, 0.87 mg/kg, 0.88 mg/kg, 0.89 mg/kg, 0.90 mg/kg, 0.91 mg/kg, 0.92 mg/kg, 0.93 mg/kg, 0.94 mg/kg, 0.95 mg/kg, 0.96 mg/kg, 0.97 mg/kg, 0.98 mg/kg, 0.90 mg/kg, 1.0 mg/kg, 1.01 mg/kg, 1.02 mg/kg, 1.03 mg/kg, 1.04 mg/kg, 1.05 mg/kg, 1.06 mg/kg, 1.07 mg/kg, 1.08 mg/kg, 1.09 mg/kg, 1.10 mg/kg, 1.11 mg/kg, 1.12 mg/kg, 1.13 mg/kg, 1.14 mg/kg, 1.15 mg/kg, 1.16 mg/kg, 1.17 mg/kg, 1.18 mg/kg, 1.19 mg/kg, or 1.20 mg/kg uricase.

Exemplary doses of immunosuppressant, such as rapamycin, for any one of the compositions or methods comprising synthetic nanocarriers comprising the immunosuppressant provided herein can be 0.050 mg/kg, 0.055 mg/kg, 0.060 mg/kg, 0.065 mg/kg, 0.070 mg/kg, 0.075 mg/kg, 0.080 mg/kg, 0.085 mg/kg, 0.090 mg/kg, 0.095 mg/kg, 0.100 mg/kg, 0.105 mg/kg, 0.110 mg/kg, 0.115 mg/kg, 0.120 mg/kg, 0.125 mg/kg, 0.130 mg/kg, 0.135 mg/kg, 0.140 mg/kg, 0.145 mg/kg, 0.150 mg/kg, 0.155 mg/kg, 0.160 mg/kg, 0.165 mg/kg, 0.170 mg/kg, 0.175 mg/kg, 0.180 mg/kg, 0.185 mg/kg, 0.190 mg/kg, 0.195 mg/kg, 0.200 mg/kg, 0.205 mg/kg, 0.210 mg/kg, 0.215 mg/kg, 0.220 mg/kg, 0.225 mg/kg, 0.230 mg/kg, 0.235 mg/kg, 0.240 mg/kg, 0.245 mg/kg, 0.250 mg/kg, 0.255 mg/kg, 0.260 mg/kg, 0.265 mg/kg, 0.270 mg/kg, 0.275 mg/kg, 0.280 mg/kg, 0.285 mg/kg, 0.290 mg/kg, 0.295 mg/kg, 0.300 mg/kg, 0.305 mg/kg, 0.310 mg/kg, 0.315 mg/kg, 0.320 mg/kg, 0.325 mg/kg, 0.330 mg/kg, 0.335 mg/kg, 0.340 mg/kg, 0.345 mg/kg, 0.350 mg/kg, 0.355 mg/kg, 0.360 mg/kg, 0.365 mg/kg, 0.370 mg/kg, 0.375 mg/kg, 0.380 mg/kg, 0.385 mg/kg, 0.390 mg/kg, 0.395 mg/kg, 0.400 mg/kg, 0.405 mg/kg, 0.410 mg/kg, 0.415 mg/kg, 0.420 mg/kg, 0.425 mg/kg, 0.430 mg/kg, 0.435 mg/kg, 0.440 mg/kg, 0.445 mg/kg, 0.450 mg/kg, 0.455 mg/kg, 0.460 mg/kg, 0.465 mg/kg, 0.470 mg/kg, 0.475 mg/kg, 0.480 mg/kg, 0.485 mg/kg, 0.490 mg/kg, 0.495 mg/kg, 0.500 mg/kg immunosuppressant, such as rapamycin.

Exemplary doses of compositions comprising synthetic nanocarriers comprising immunosuppressant, such as rapamycin, as provided herein can be 0.55 mg/kg, 0.56 mg/kg, 0.57 mg/kg, 0.58 mg/kg, 0.59 mg/kg, 0.60 mg/kg, 0.61 mg/kg, 0.62 mg/kg, 0.63 mg/kg, 0.64 mg/kg, 0.65 mg/kg, 0.66 mg/kg, 0.67 mg/kg, 0.68 mg/kg, 0.69 mg/kg, 0.70 mg/kg, 0.71 mg/kg, 0.72 mg/kg, 0.73 mg/kg, 0.74 mg/kg, 0.75 mg/kg, 0.76 mg/kg, 0.77 mg/kg, 0.78 mg/kg, 0.79 mg/kg, 0.80 mg/kg, 0.81 mg/kg, 0.82 mg/kg, 0.83 mg/kg, 0.84 mg/kg, 0.85 mg/kg, 0.86 mg/kg, 0.87 mg/kg, 0.88 mg/kg, 0.89 mg/kg, 0.90 mg/kg, 0.91 mg/kg, 0.92 mg/kg, 0.93 mg/kg, 0.94 mg/kg, 0.95 mg/kg, 0.96 mg/kg, 0.97 mg/kg, 0.98 mg/kg, 0.90 mg/kg, 1.0 mg/kg, 1.01 mg/kg, 1.02 mg/kg, 1.03 mg/kg, 1.04 mg/kg, 1.05 mg/kg, 1.06 mg/kg, 1.07 mg/kg, 1.08 mg/kg, 1.09 mg/kg, 1.10 mg/kg, 1.11 mg/kg, 1.12 mg/kg, 1.13 mg/kg, 1.14 mg/kg, 1.15 mg/kg, 1.16 mg/kg, 1.17 mg/kg, 1.18 mg/kg, 1.19 mg/kg, 1.20 mg/kg, 1.21 mg/kg, 1.22 mg/kg, 1.23 mg/kg, 1.24 mg/kg, 1.25 mg/kg, 1.26 mg/kg, 1.27 mg/kg, 1.28 mg/kg, 1.29 mg/kg, 1.30 mg/kg, 1.31 mg/kg, 1.32 mg/kg, 1.33 mg/kg, 1.34 mg/kg, 1.35 mg/kg, 1.36 mg/kg, 1.37 mg/kg, 1.38 mg/kg, 1.39 mg/kg, 1.40 mg/kg, 1.41 mg/kg, 1.42 mg/kg, 1.43 mg/kg, 1.44 mg/kg, 1.45 mg/kg, 1.46 mg/kg, 1.47 mg/kg, 1.48 mg/kg, 1.49 mg/kg, 1.50 mg/kg, 1.51 mg/kg, 1.52 mg/kg, 1.53 mg/kg, 1.54 mg/kg, 1.55 mg/kg, 1.56 mg/kg, 1.57 mg/kg, 1.58 mg/kg, 1.59 mg/kg, 1.60 mg/kg, 1.61 mg/kg, 1.62 mg/kg, 1.63 mg/kg, 1.64 mg/kg, 1.65 mg/kg, 1.66 mg/kg, 1.67 mg/kg, 1.68 mg/kg, 1.69 mg/kg, 1.70 mg/kg, 1.71 mg/kg, 1.72 mg/kg, 1.73 mg/kg, 1.74 mg/kg, 1.75 mg/kg, 1.76 mg/kg, 1.77 mg/kg, 1.78 mg/kg, 1.79 mg/kg, 1.80 mg/kg, 1.81 mg/kg, 1.82 mg/kg, 1.83 mg/kg, 1.84 mg/kg, 1.85 mg/kg, 1.86 mg/kg, 1.87 mg/kg, 1.88 mg/kg, 1.89 mg/kg, 1.90 mg/kg, 1.91 mg/kg, 1.92 mg/kg, 1.93 mg/kg, 1.94 mg/kg, 1.95 mg/kg, 1.96 mg/kg, 1.97 mg/kg, 1.98 mg/kg, 1.99 mg/kg, 2.00 mg/kg, 2.01 mg/kg, 2.02 mg/kg, 2.03 mg/kg, 2.04 mg/kg, 2.05 mg/kg, 2.06 mg/kg, 2.07 mg/kg, 2.08 mg/kg, 2.09 mg/kg, 2.10 mg/kg, 2.11 mg/kg, 2.12 mg/kg, 2.13 mg/kg, 2.14 mg/kg, 2.15 mg/kg, 2.16 mg/kg, 2.17 mg/kg, 2.18 mg/kg, 2.19 mg/kg, 2.20 mg/kg, 2.21 mg/kg, 2.22 mg/kg, 2.23 mg/kg, 2.24 mg/kg, 2.25 mg/kg, 2.26 mg/kg, 2.27 mg/kg, 2.28 mg/kg, 2.29 mg/kg, 2.30 mg/kg, 2.31 mg/kg, 2.32 mg/kg, 2.33 mg/kg, 2.34 mg/kg, 2.35 mg/kg, 2.36 mg/kg, 2.37 mg/kg, 2.38 mg/kg, 2.39 mg/kg, 2.40 mg/kg, 2.41 mg/kg, 2.42 mg/kg, 2.43 mg/kg, 2.44 mg/kg, 2.45 mg/kg, 2.46 mg/kg, 2.47 mg/kg, 2.48 mg/kg, 2.49 mg/kg, 2.50 mg/kg, 2.51 mg/kg, 2.52 mg/kg, 2.53 mg/kg, 2.54 mg/kg, 2.55 mg/kg, 2.56 mg/kg, 2.57 mg/kg, 2.58 mg/kg, 2.59 mg/kg, 2.60 mg/kg, 2.61 mg/kg, 2.62 mg/kg, 2.63 mg/kg, 2.64 mg/kg, 2.65 mg/kg, 2.66 mg/kg, 2.67 mg/kg, 2.68 mg/kg, 2.69 mg/kg, 2.70 mg/kg, 2.71 mg/kg, 2.72 mg/kg, 2.73 mg/kg, 2.74 mg/kg, 2.75 mg/kg, 2.76 mg/kg, 2.77 mg/kg, 2.78 mg/kg, 2.79 mg/kg, 2.80 mg/kg, 2.81 mg/kg, 2.82 mg/kg, 2.83 mg/kg, 2.84 mg/kg, 2.85 mg/kg, 2.86 mg/kg, 2.87 mg/kg, 2.88 mg/kg, 2.89 mg/kg, 2.90 mg/kg, 2.91 mg/kg, 2.92 mg/kg, 2.93 mg/kg, 2.94 mg/kg, 2.95 mg/kg, 2.96 mg/kg, 2.97 mg/kg, 2.98 mg/kg, 2.99 mg/kg, 3.00 mg/kg, 3.01 mg/kg, 3.02 mg/kg, 3.03 mg/kg, 3.04 mg/kg, 3.05 mg/kg, 3.06 mg/kg, 3.07 mg/kg, 3.08 mg/kg, 3.09 mg/kg, 3.10 mg/kg, 3.11 mg/kg, 3.12 mg/kg, 3.13 mg/kg, 3.14 mg/kg, 3.15 mg/kg, 3.16 mg/kg, 3.17 mg/kg, 3.18 mg/kg, 3.19 mg/kg, 3.20 mg/kg, 3.21 mg/kg, 3.22 mg/kg, 3.23 mg/kg, 3.24 mg/kg, 3.25 mg/kg, 3.26 mg/kg, 3.27 mg/kg, 3.28 mg/kg, 3.29 mg/kg, 3.30 mg/kg, 3.31 mg/kg, 3.32 mg/kg, 3.33 mg/kg, 3.34 mg/kg, 3.35 mg/kg, 3.36 mg/kg, 3.37 mg/kg, 3.38 mg/kg, 3.39 mg/kg, 3.40 mg/kg, 3.41 mg/kg, 3.42 mg/kg, 3.43 mg/kg, 3.44 mg/kg, 3.45 mg/kg, 3.46 mg/kg, 3.47 mg/kg, 3.48 mg/kg, 3.49 mg/kg, 3.50 mg/kg, 3.51 mg/kg, 3.52 mg/kg, 3.53 mg/kg, 3.54 mg/kg, 3.55 mg/kg, 3.56 mg/kg, 3.57 mg/kg, 3.58 mg/kg, 3.59 mg/kg, 3.60 mg/kg, 3.61 mg/kg, 3.62 mg/kg, 3.63 mg/kg, 3.64 mg/kg, 3.65 mg/kg, 3.66 mg/kg, 3.67 mg/kg, 3.68 mg/kg, 3.69 mg/kg, 3.70 mg/kg, 3.71 mg/kg, 3.72 mg/kg, 3.73 mg/kg, 3.74 mg/kg, 3.75 mg/kg, 3.76 mg/kg, 3.77 mg/kg, 3.78 mg/kg, 3.79 mg/kg, 3.80 mg/kg, 3.81 mg/kg, 3.82 mg/kg, 3.83 mg/kg, 3.84 mg/kg, 3.85 mg/kg, 3.86 mg/kg, 3.87 mg/kg, 3.88 mg/kg, 3.89 mg/kg, 3.90 mg/kg, 3.91 mg/kg, 3.92 mg/kg, 3.93 mg/kg, 3.94 mg/kg, 3.95 mg/kg, 3.96 mg/kg, 3.97 mg/kg, 3.98 mg/kg, 3.99 mg/kg, 4.00 mg/kg, 4.01 mg/kg, 4.02 mg/kg, 4.03 mg/kg, 4.04 mg/kg, 4.05 mg/kg, 4.06 mg/kg, 4.07 mg/kg, 4.08 mg/kg, 4.09 mg/kg, 4.10 mg/kg, 4.11 mg/kg, 4.12 mg/kg, 4.13 mg/kg, 4.14 mg/kg, 4.15 mg/kg, 4.16 mg/kg, 4.17 mg/kg, 4.18 mg/kg, 4.19 mg/kg, 4.20 mg/kg, 4.21 mg/kg, 4.22 mg/kg, 4.23 mg/kg, 4.24 mg/kg, 4.25 mg/kg, 4.26 mg/kg, 4.27 mg/kg, 4.28 mg/kg, 4.29 mg/kg, 4.30 mg/kg, 4.31 mg/kg, 4.32 mg/kg, 4.33 mg/kg, 4.34 mg/kg, 4.35 mg/kg, 4.36 mg/kg, 4.37 mg/kg, 4.38 mg/kg, 4.39 mg/kg, 4.40 mg/kg, 4.41 mg/kg, 4.42 mg/kg, 4.43 mg/kg, 4.44 mg/kg, 4.45 mg/kg, 4.46 mg/kg, 4.47 mg/kg, 4.48 mg/kg, 4.49 mg/kg, 4.50 mg/kg, 4.51 mg/kg, 4.52 mg/kg, 4.53 mg/kg, 4.54 mg/kg, 4.55 mg/kg, 4.56 mg/kg, 4.57 mg/kg, 4.58 mg/kg, 4.59 mg/kg, 4.60 mg/kg, 4.61 mg/kg, 4.62 mg/kg, 4.63 mg/kg, 4.64 mg/kg, 4.65 mg/kg, 4.66 mg/kg, 4.67 mg/kg, 4.68 mg/kg, 4.69 mg/kg, 4.70 mg/kg, 4.71 mg/kg, 4.72 mg/kg, 4.73 mg/kg, 4.74 mg/kg, 4.75 mg/kg, 4.76 mg/kg, 4.77 mg/kg, 4.78 mg/kg, 4.79 mg/kg, 4.80 mg/kg, 4.81 mg/kg, 4.82 mg/kg, 4.83 mg/kg, 4.84 mg/kg, 4.85 mg/kg, 4.86 mg/kg, 4.87 mg/kg, 4.88 mg/kg, 4.89 mg/kg, 4.90 mg/kg, 4.91 mg/kg, 4.92 mg/kg, 4.93 mg/kg, 4.94 mg/kg, 4.95 mg/kg, 4.96 mg/kg, 4.97 mg/kg, 4.98 mg/kg, 4.99 mg/kg, 5.00 mg/kg, 5.01 mg/kg, 5.02 mg/kg, 5.03 mg/kg, 5.04 mg/kg, 5.05 mg/kg, 5.06 mg/kg, 5.07 mg/kg, 5.08 mg/kg, 5.09 mg/kg, 5.10 mg/kg, 5.11 mg/kg, 5.12 mg/kg, 5.13 mg/kg, 5.14 mg/kg, 5.15 mg/kg, 5.16 mg/kg, 5.17 mg/kg, 5.18 mg/kg, 5.19 mg/kg, 5.20 mg/kg, 5.21 mg/kg, 5.22 mg/kg, 5.23 mg/kg, 5.24 mg/kg, 5.25 mg/kg, 5.26 mg/kg, 5.27 mg/kg, 5.28 mg/kg, 5.29 mg/kg, 5.30 mg/kg, 5.31 mg/kg, 5.32 mg/kg, 5.33 mg/kg, 5.34 mg/kg, 5.35 mg/kg, 5.36 mg/kg, 5.37 mg/kg, 5.38 mg/kg, 5.39 mg/kg, 5.40 mg/kg, 5.41 mg/kg, 5.42 mg/kg, 5.43 mg/kg, 5.44 mg/kg, 5.45 mg/kg, 5.46 mg/kg, 5.47 mg/kg, 5.48 mg/kg, 5.49 mg/kg, 5.50 mg/kg, 5.51 mg/kg, 5.52 mg/kg, 5.53 mg/kg, 5.54 mg/kg, 5.55 mg/kg, 5.56 mg/kg, 5.57 mg/kg, 5.58 mg/kg, 5.59 mg/kg, 5.60 mg/kg, 5.61 mg/kg, 5.62 mg/kg, 5.63 mg/kg, 5.64 mg/kg, 5.65 mg/kg, 5.66 mg/kg, 5.67 mg/kg, 5.68 mg/kg, 5.69 mg/kg, 5.70 mg/kg, 5.71 mg/kg, 5.72 mg/kg, 5.73 mg/kg, 5.74 mg/kg, 5.75 mg/kg, 5.76 mg/kg, 5.77 mg/kg, 5.78 mg/kg, 5.79 mg/kg, 5.80 mg/kg, 5.81 mg/kg, 5.82 mg/kg, 5.83 mg/kg, 5.84 mg/kg, 5.85 mg/kg, 5.86 mg/kg, 5.87 mg/kg, 5.88 mg/kg, 5.89 mg/kg, 5.90 mg/kg, 5.91 mg/kg, 5.92 mg/kg, 5.93 mg/kg, 5.94 mg/kg, 5.95 mg/kg, 5.96 mg/kg, 5.97 mg/kg, 5.98 mg/kg, 5.99 mg/kg, 6.00 mg/kg, 6.01 mg/kg, 6.02 mg/kg, 6.03 mg/kg, 6.04 mg/kg, 6.05 mg/kg, 6.06 mg/kg, 6.07 mg/kg, 6.08 mg/kg, 6.09 mg/kg, 6.10 mg/kg, 6.11 mg/kg, 6.12 mg/kg, 6.13 mg/kg, 6.14 mg/kg, 6.15 mg/kg, 6.16 mg/kg, 6.17 mg/kg, 6.18 mg/kg, 6.19 mg/kg, 6.20 mg/kg, 6.21 mg/kg, 6.22 mg/kg, 6.23 mg/kg, 6.24 mg/kg, 6.25 mg/kg, 6.26 mg/kg, 6.27 mg/kg, 6.28 mg/kg, 6.29 mg/kg, 6.30 mg/kg, 6.31 mg/kg, 6.32 mg/kg, 6.33 mg/kg, 6.34 mg/kg, 6.35 mg/kg, 6.36 mg/kg, 6.37 mg/kg, 6.38 mg/kg, 6.39 mg/kg, 6.40 mg/kg, 6.41 mg/kg, 6.42 mg/kg, 6.43 mg/kg, 6.44 mg/kg, 6.45 mg/kg, 6.46 mg/kg, 6.47 mg/kg, 6.48 mg/kg, 6.49 mg/kg, or 6.50 mg/kg, for any one of the compositions or methods provided, wherein the dose is given as the mg of the synthetic nanocarriers comprising the immunosuppressant, such as rapamycin.

Any one of the doses provided herein for the composition comprising uricase, such as pegsiticase (i.e., pegadricase), can be used in any one of the methods or compositions or kits provided herein. Any one of the doses provided herein for the composition comprising synthetic nanocarriers comprising an immunosuppressant, such as rapamycin, can be used in any one of the methods or compositions or kits provided herein. Any one of the doses provided herein for the composition comprising an anti-inflammatory therapeutic can be used in any one of the methods or compositions or kits provided herein. Any one of the doses provided herein for the composition(s) comprising an infusion reaction therapeutic can be used in any one of the methods or compositions or kits provided herein. Generally, when referring to a dose to be administered to a subject the dose is a label dose. Thus, in any one of the methods or composition provided herein the dose(s) are label dose(s).

In some embodiments of any one of the methods provided herein, an additional volume (prime volume) may be used to prime the infusion line for administering any of the compositions provided herein to the subject.

Provided herein are a number of possible dosing schedules. Accordingly, any one of the subjects provided herein may be treated according to any one of the dosing schedules provided herein. As an example, any one of the subject provided herein may be treated with a composition comprising uricase, such as pegylated uricase, and/or composition comprising synthetic nanocarriers comprising an immunosuppressant, such as rapamycin, and/or a composition comprising an anti-inflammatory therapeutic and/or a composition(s) comprising an infusion reaction therapeutic according to any one of these dosage schedules.

The mode of administration for the composition(s) of any one of the treatment methods provided may be by intravenous administration, such as an intravenous infusion that, for example, may take place over about 1 hour. Additionally, any one of the methods of treatment provided herein may also include administration of an additional therapeutic, such as a uric acid lowering therapeutic, such as a uricase, or an anti-gout flare prophylactic treatment. The administration of the additional therapeutic may be according to any one of the applicable treatment regimens and/or modes of administration as provided herein.

Preferably, in some embodiments, the treatment with a combination of synthetic nanocarrier composition comprising immunosuppressant, such as rapamycin, with a composition comprising uricase, such as pegylated uricase, can comprise three doses of the synthetic nanocarrier composition concomitantly with the uricase-comprising composition followed by two doses of uricase without the concomitant administration of a composition comprising an immunosuppressant, such as a synthetic nanocarrier composition comprising an immunosuppressant, with or without the concomitant administration of an additional therapeutic. In such an embodiment, each dose may be administered every two to four weeks. In one embodiment, a method is provided whereby any one of the subjects provided herein is concomitantly administered three doses of a synthetic nanocarrier composition with a uricase-comprising composition monthly for three months. In another embodiment, this method further comprises administering 2, 3, 4, 5, 6, 7, 8, 9 or 10 or more monthly doses of a uricase-comprising composition alone or without the concomitant administration of immunosuppressant, such as a synthetic nanocarrier composition comprising an immunosuppressant, or an additional therapeutic. In some embodiments of any one of the methods provided herein, the level of uric acid is measured in the subject at one or more time points before, during and/or after the treatment period.

Subjects

Subjects provided herein can be in need of treatment according to any one of the methods or compositions or kits provided herein. Such subjects include those with elevated serum uric acid levels or uric acid deposits. Such subjects include those with hyperuricemia. It is within the skill of a clinician to be able to determine subjects in need of a treatment as provided herein.

In some embodiments, any one of the subjects for treatment as provided in any one of the methods provided has gout or a condition associated with gout or another condition as provided herein. In some embodiments, any one of the subjects for treatment as provided in any one of the methods provided the subject has had or is expected to have gout flare.

In some embodiments, the subject has or is at risk of having erosive bone disease associated with gout, cirrhosis or steatohepatitis associated with gout, or visceral gout.

In some embodiments, the subject has or is at risk of having an elevated uric acid level, e.g., an elevated plasma or serum uric acid level. When blood levels of uric acid may exceed the physiologic limit of solubility, the uric acid may crystallize in the tissues, including the joints, and may cause gout and gout-associated conditions.

In some embodiments, serum uric acid levels ≥5 mg/dL, ≥6 mg/dL, or ≥7 mg/dL are indicative that a subject may be a candidate for treatment with any one of the methods or compositions or kits described herein. In some embodiments, such a subject has a serum level of uric acid ≥6 mg/dL, for example, between 6.1 mg/dL-15 mg/dL, between 6.1 mg/dL-10 mg/dL, 7 mg/dL-15 mg/dL, 7 mg/dL-10 mg/dL, 8 mg/dL-15 mg/dL, 8 mg/dL-10 mg/dL, 9 mg/dL–15 mg/dL, 9 mg/dL-10 mg/dL, 10 mg/dL-15 mg/dL, or 11 mg/dL-14 mg/dL. In some embodiments, the subject has serum level of uric acid of about 6.1 mg/dL, 6.2 mg/dL, 6.3 mg/dL, 6.4 mg/dL, 6.5 mg/dL, 6.7 mg/dL, 6.8 mg/dL, 6.9 mg/dL, 7.0 mg/dL, 7.1 mg/dL, 7.2 mg/dL, 7.3 mg/dL, 7.4 mg/dL, 7.5 mg/dL, 7.6 mg/dL 7.7 mg/dL, 7.8 mg/dL, 7.9 mg/dL, 8.0 mg/dL, 8.1 mg/dL, 8.2 mg/dL, 8.3 mg/dL, 8.4 mg/dL, 8.5 mg/dL, 8.6 mg/dL, 8.7 mg/dL, 8.8 mg/dL, 8.9 mg/dL, 9.0 mg/dL, 9.1 mg/dL, 9.2 mg/dL, 9.3 mg/dL, 9.4 mg/dL, 9.5 mg/dL, 9.6 mg/dL, 9.7 mg/dL, 9.8 mg/dL, 9.9 mg/dL, 10.0 mg/dL, 10.1 mg/dL, 10.2 mg/dL, 10.3 mg/dL, 10.4 mg/dL, 10.5 mg/dL, 10.6 mg/dL, 10.7 mg/dL, 10.8 mg/dL, 10.9 mg/dL, 11.0 mg/dL, 11.1 mg/dL, 11.2 mg/dL, 11.3 mg/dL, 11.4 mg/dL, 11.5 mg/dL, 11.6 mg/dL, 11.7 mg/dL, 11.8 mg/dL, 11.9 mg/dL, 12.0 mg/dL, 12.1 mg/dL, 12.2 mg/dL, 12.3 mg/dL, 12.4 mg/dL, 12.5 mg/dL, 12.6 mg/dL, 12.7 mg/dL, 12.8 mg/dL, 12.9 mg/dL, 13.0 mg/dL, 13.1 mg/dL, 13.2 mg/dL, 13.3 mg/dL, 13.4 mg/dL, 13.5 mg/dL, 13.6 mg/dL, 13.7 mg/dL, 13.8 mg/dL, 13.9 mg/dL, 14.0 mg/dL, 14.1 mg/dL, 14.2 mg/dL, 14.3 mg/dL, 14.4 mg/dL, 14.5 mg/dL, 14.6 mg/dL, 14.7 mg/dL, 14.8 mg/dL, 14.9 mg/dL, 15.0 mg/dL or higher. In some embodiments, the subject has a plasma or serum uric acid level of 5.0 mg/dL, 5.1 mg/dL, 5.2 mg/dL, 5.3 mg/dL, 5.4 mg/dL, 5.5 mg/dL, 5.6 mg/dL, 5.7 mg/dL, 5.8 mg/dL, 5.9 mg/dL, 6.0 mg/dL, 6.1 mg/dL, 6.2 mg/dL, 6.3 mg/dL, 6.4 mg/dL, 6.5 mg/dL, 6.6 mg/dL, 6.7 mg/dL, 6.8 mg/dL, 6.9 mg/dL, or 7.0 mg/dL. In some embodiments, the subject has a plasma or serum uric acid level of greater than or equal to 5.0 mg/dL, 5.1 mg/dL, 5.2 mg/dL, 5.3 mg/dL, 5.4 mg/dL, 5.5 mg/dL, 5.6 mg/dL, 5.7 mg/dL, 5.8 mg/dL, 5.9 mg/dL, 6.0 mg/dL, 6.1 mg/dL, 6.2 mg/dL, 6.3 mg/dL, 6.4 mg/dL, 6.5 mg/dL, 6.6 mg/dL, 6.7 mg/dL, 6.8 mg/dL, 6.9 mg/dL, or 7.0 mg/dL.

In some embodiments, the subject has, or is at risk of having, hyperuricemia. In some embodiments, the subject has, or is at risk of having, gout, acute gout, acute intermittent gout, gouty arthritis, acute gouty arthritis, acute gouty arthropathy, acute polyarticular gout, recurrent gouty arthritis, chronic gout (with our without tophi), tophaceous gout, chronic tophaceous gout, chronic advanced gout (with our without tophi), chronic polyarticular gout (with our without tophi), chronic gouty arthropathy (with our without tophi), idiopathic gout, idiopathic chronic gout (with or without tophi), primary gout, chronic primary gout (with or without tophi), refractory gout, such as chronic refractory gout, axial gouty arthropathy, a gout attack, a gout flare, podagra (i.e., monarticular arthritis of the great toe), chiragra (i.e., monarticular arthritis of the hand), gonagra (i.e., monarticular arthritis of the knee), gouty bursitis, gouty spondylitis, gouty synovitis, gouty tenosynovitis, gout that affects tendons and ligaments, lead-induced gout (i.e., saturnine gout), drug induced gout, gout due to renal impairment, gout due to kidney disease, chronic gout due to renal impairment (with or without tophi), chronic gout due to kidney disease (with or without tophi), erosive bone disease associated with gout, stroke associated with gout, vascular plaque associated with gout, cirrhosis or steatohepatitis associated with gout, liver-associated gout, incident and recurrent gout, diabetes associated with damage to pancreas in gout, general inflammatory diseases exacerbated by gout, other secondary gout, or unspecified gout.

In some embodiments, the subject has, or is at risk of having, a condition associated with the renal system, for example, calculus of urinary tract due to gout, uric acid urolithiasis, uric acid nephrolithiasis, uric acid kidney stones, gouty nephropathy, acute gouty nephropathy, chronic gouty nephropathy, urate nephropathy, uric acid nephropathy, and gouty interstitial nephropathy.

In some embodiments, the subject has, or is at risk of having, a condition associated with the nervous system, for example, peripheral autonomic neuropathy due to gout, gouty neuropathy, gouty peripheral neuropathy, gouty entrapment neuropathy, or gouty neuritis.

In some embodiments, the subject has, or is at risk of having, a condition associated with the cardiovascular system, for example, metabolic syndrome, hypertension, obesity, diabetes, myocardial infarction, stroke, dyslipidemia, hypertriglyceridemia, insulin resistance/hyperglycemia, coronary artery disease/coronary heart disease, coronary artery disease or blockage associated with gout or hyperuricemia, heart failure, peripheral arterial disease, stroke/cerebrovascular disease, peripheral vascular disease, and cardiomyopathy due to gout.

In some embodiments, the subject has, or is at risk of having, a condition associated with the ocular system including, for example, gouty iritis, inflammatory disease in the eye caused by gout, dry eye syndrome, red eye, uveitis, intraocular hypertension, glaucoma, and cataracts.

In some embodiments, the subject has, or is at risk of having, a condition associated with the skin including, for example, gout of the external ear, gouty dermatitis, gouty eczema, gouty panniculitis, and miliarial gout.

Compositions and Kits

Compositions provided herein may comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

Compositions according to the invention may comprise pharmaceutically acceptable excipients. The compositions may be made using conventional pharmaceutical manufacturing and compounding techniques to arrive at useful dosage forms. Techniques suitable for use in practicing the present invention may be found in Handbook of Industrial Mixing: Science and Practice, Edited by Edward L. Paul, Victor A. Atiemo-Obeng, and Suzanne M. Kresta, 2004 John Wiley & Sons, Inc.; and Pharmaceutics: The Science of Dosage Form Design, 2nd Ed. Edited by M. E. Auten, 2001, Churchill Livingstone. In an embodiment, compositions are suspended in a sterile saline solution for injection together with a preservative.

It is to be understood that the compositions of the invention can be made in any suitable manner, and the invention is in no way limited to compositions that can be produced using the methods described herein. Selection of an appropriate method of manufacture may require attention to the properties of the particular elements being associated.

In some embodiments, compositions are manufactured under sterile conditions or are initially or terminally sterilized. This can ensure that resulting compositions are sterile and non-infectious, thus improving safety when compared to non-sterile compositions. This provides a valuable safety measure, especially when subjects receiving the compositions have immune defects, are suffering from infection, and/or are susceptible to infection. In some embodiments, the compositions may be lyophilized and stored in suspension or as lyophilized powder depending on the formulation strategy for extended periods without losing activity.

Administration according to the present invention may be by a variety of routes, including but not limited to an intravenous route. The compositions referred to herein may be manufactured and prepared for administration using conventional methods.

The compositions of the invention can be administered in effective amounts, such as the effective amounts described elsewhere herein. Doses of compositions as provided herein may contain varying amounts of elements according to the invention. The amount of elements present in the compositions for dosing can be varied according to their nature, the therapeutic benefit to be accomplished, and other such parameters. The compositions for dosing may be administered according to any one of the frequencies provided herein.

Another aspect of the disclosure relates to kits. In some embodiments, the kit comprises any one or more of the compositions provided herein. In some embodiments of any one of the kits provided, the kit comprises any one or more of the compositions comprising one or more compositions comprising an anti-inflammatory therapeutic and/or an infusion reaction therapeutic and one or more synthetic nanocarrier compositions provided herein. Any one or more of the kits can further comprise one or more compositions comprising an uricase. Each of the types of compositions can be in one container or in more than one container in the kit. In some embodiments of any one of the kits provided, the container is a vial or an ampoule. In some embodiments of any one of the kits provided, the composition(s) are in lyophilized form each in a separate container or in the same container, such that they may be reconstituted at a subsequent time. In some embodiments of any one of the kits provided, the composition(s) are in the form of a frozen suspension each in a separate container or in the same container, such that they may be reconstituted at a subsequent time. In some embodiments of any one of the kits, the frozen suspension further comprises PBS. In some embodiments of any one of the kits, the kit further comprises PBS and/or 0.9% sodium chloride, USP.

In some embodiments of any one of the kits provided, the kit further comprises instructions for reconstitution, mixing, administration, etc. In some embodiments of any one of the kits provided, the instructions include a description of any one of the methods described herein. Instructions can be in any suitable form, e.g., as a printed insert or a label. In some embodiments of any one of the kits provided herein, the kit further comprises one or more syringes or other device(s) that can deliver the composition(s) in vivo to a subject.

EXAMPLES

Example 1—SEL-212 Clinical Trial Results, Human

Phase 1a Clinical Trial

The Phase 1a clinical trial for SEL-212 was an ascending dose trial of pegsiticase alone in 22 subjects with elevated serum uric acid levels greater than 6 mg/dl who were separated into five cohorts. Each cohort received a single intravenous infusion of pegsiticase at the following dose levels of 0.1 mg/kg for Cohort #1, 0.2 mg/kg for Cohort #2, 0.4 mg/kg for Cohort #3, 0.8 mg/kg for Cohort #4 and 1.2 mg/kg for Cohort #5. Dosing began with the lowest dose and only after an entire cohort was safely dosed was the next cohort started. The subjects were monitored during a 30 day period post infusion with visits occurring on day 7, 14, 21 and the end of trial visit on day 30. Blood and serum of each patient was evaluated for serum uric acid, ADAs (specifically anti-peg, anti-uricase and anti-pegsiticase) and safety parameters. It was observed that pegsiticase demonstrated no serious adverse events and was well tolerated at the five dose levels tested. Additionally, it was observed that pegsiticase rapidly reduced (within hours) and sustained average serum uric acid levels below 6 mg/dl for each cohort for 14 to 30 days, depending on the dose level. Consistent with preclinical studies in animals, pegsiticase induced uricase specific ADAs in all subjects with varying levels in this Phase 1a trial.

Figure 3:
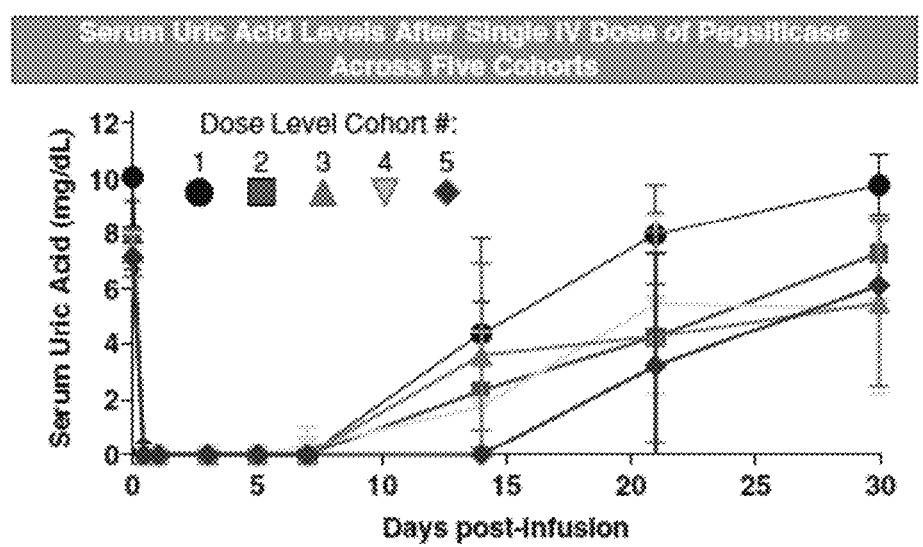
FIG. 3 is a graph of mean serum uric acid (sUA) levels in the 5 cohorts of the phase 1a clinical trial following a single intravenous infusion of pegsiticase.

FIG. 3 depicts average serum uric acid levels of the Phase 1a clinical trial's five cohorts tested at different measurement intervals (Day 7, 14, 21 and 30) during the course of the 30 day period following the single intravenous infusion of pegsiticase at the outset of the trial.

The serum uric acid levels were measured at baseline and days seven, 14, 21 and 30 and uricase specific ADA levels at baseline and days seven, 14 and 30 following a single intravenous injection of pegsiticase. Uricase specific ADA levels at day 21 in the Phase 1a clinical trial were not measured. Based on the results from the Phase 1a clinical trial, it was observed that pegsiticase at a tolerated dose is capable of achieving and maintaining a reduction of serum uric acid below the target of 6 mg/dl for a 30 day period in the absence of inhibitory uricase specific ADAs.

Phase 1b Clinical Trial

The Phase 1b clinical trial enrolled 63 patients with serum uric acid levels greater than 6 mg/dl were separated into 11 cohorts. A single intravenous infusion of SVP Rapamycin alone at the following ascending dose levels was administered to four cohorts in ascending order. Each cohort consisted of seven patients and they were designated as follows: Cohort #1 (0.03 mg/kg), Cohort #3 (0.1 mg/kg), Cohort #5 (0.3 mg/kg) and Cohort #7 (0.5 mg/kg) collectively the SVP Rapamycin Cohorts. After a cohort of the SVP-Rapamycin alone had successfully and safely been dosed the corresponding dose level of SVP Rapamycin was combined with a fixed dose of pegsiticase (0.4 mg/kg). The combination was co-administered sequentially as a single intravenous infusion, with the SVP Rapamycin infusion preceding the pegsiticase infusion. The cohort designation is as follows for the six cohorts (5 patients per cohort), which were Cohort #2 (SVP Rapamycin 0.03 mg/kg+0.4 mg/kg pegsiticase), Cohort #4 (SVP Rapamycin 0.1 mg/kg+0.4 mg/kg pegsiticase), Cohort #6 (SVP Rapamycin 0.3 mg/kg+0.4 mg/kg pegsiticase), Cohort #10 (0.4 mg/kg pegsiticase+0.03 mg/kg SVP Rapamycin separated by 48 hours), Cohort #12 (SVP Rapamycin 0.15 mg/kg+0.4 mg/kg pegsiticase) and Cohort #14 (SVP Rapamycin 0.1 mg/kg+0.4 mg/kg pegsiticase) collectively the SEL-212 Cohorts. In Cohort #9 a fixed amount of pegsiticase alone at a dose level of 0.4 mg/kg was administered to five patients, which is referred to as the Pegsiticase Cohort. Methods of such treatment are also provided. The subjects were monitored during a 30 day period post infusion with visits occurring on day 7, 14, 21 and the end of trial visit on day 30. Blood and serum of each patient was evaluated for serum uric acid, ADAs (specifically anti-PEG, anti-uricase and anti-pegsiticase) and safety parameters. The primary objective of the Phase 1b clinical trial was to evaluate the safety and tolerability of SVP Rapamycin alone and in combination with a fixed dose of pegsiticase. A secondary clinical objective was to evaluate the ability of SVP Rapamycin co-administered with pegsiticase to reduce serum uric acid levels and mitigate the formation of uricase specific ADAs when compared to administration of pegsiticase alone.

FIG. 4 indicates the serum uric acid levels of Cohort #3 from the Phase 1a clinical trial, in which subjects received a fixed amount of pegsiticase alone (at the same 0.4 mg/kg pegsiticase. Also in the first graph is the data from Cohort #9 (pegsiticase 0.4 mg/kg) of the Phase 1b clinical trial. This graph represents the reproducibility of the data across two separate studies. In both cohorts there is initial control of the serum uric acid (levels maintained below 6 mg/dL) but past day 14, individuals loose the enzyme activity. Also in FIG. 4, the data from the SVP rapamycin alone cohort is displayed. All values remain essentially the same throughout the 30 days of testing indicating that SVP Rapamycin alone has no effect on serum uric acid levels. For Cohort #2 from the Phase 1b clinical trial, which received the lowest dose of SVP Rapamycin co-administered with pegsiticase, it was observed that four out of five subjects tested maintained serum uric acid levels below 6 mg/dl through day 21 of the trial. It was also observed that four out of five subjects in Cohort #4 from the Phase 1b clinical trial, which received the second lowest dose of SVP Rapamycin co-administered with pegsiticase, maintained levels of serum uric acid of less than 0.1 mg/dl through day 30. For Cohort #6 (SEL-212 Cohort), it was observed that four (out of the projected five) subjects maintained levels of serum uric acid of less than 0.1 mg/dl through day 21 and two (out of the projected five) subjects maintained levels of serum uric acid of less than 0.1 mg/dl through day 30. By comparison, for Cohort #9 (Pegsiticase Cohort), four of the five subjects returned to baseline serum uric acid levels by day 30.

FIG. 4 shows the serum uric acid levels and uricase specific ADA levels for each subject in Cohort #3 of the Phase 1a clinical trial and Cohort #9 (Pegsiticase Cohort) of the Phase 1b clinical trial for comparison to the serum uric acid levels and uricase specific ADA levels for each subject in Cohort #4 (SEL-212 Cohort) in the Phase 1b clinical trial. Cohort #3 from the Phase 1a clinical trial is depicted along with Cohort #9 from the Phase 1b clinical trial for purposes of comparison against Cohort #4 from the Phase 1b clinical trial because the subjects in these cohorts received the same fixed dose of pegsiticase. In addition, Cohort #4 from the Phase 1b clinical trial is depicted in FIG. 4 because the subjects in Cohort #4 from the Phase 1b clinical trial received a higher dose of SVP Rapamycin than did the subjects in Cohort #2 in the Phase 1b clinical trial, the other SEL-212 Cohort for which 30 day observation period data from the Phase 1b clinical trial was available.

As depicted in FIG. 4, in Cohort #3 from the Phase 1a clinical trial and Cohort #9 from the Phase 1b clinical trial, uricase specific ADA formation at day 14 resulting in a return to baseline levels of serum uric acid was observed. In comparison, for Cohort #4 from the Phase 1b clinical trial, it was observed that minimal uricase specific ADA formation in four of the five subjects tested with corresponding maintenance of control of serum uric acid levels through day 30. In the Phase 1a clinical trial, uricase specific ADA levels at day 21 was not measured. However, in the course of conducting the Phase 1a clinical trial, it was learned that it would be useful to measure uricase specific ADA levels at day 21 to more fully understand any variations in such levels between day 14 and day 30. As a result, for the Phase 1b clinical trial, uricase specific ADA levels at day 21 were monitored.

Additional serum uric acid and uricase specific ADA data after day 30 was collected for three of the subjects in Cohort #4 (SEL-212 Cohort) that had no or very low serum uric acid and uricase specific ADA levels at day 30. Data on day 37 was collected for all three of these subjects and again on day 42 or day 44 for two of the three subjects. Each of these three subjects had no or very low uricase specific ADA levels on day 37, day 42 or day 44, as applicable. Serum uric acid levels remained below baseline on day 37 in all three subjects. With respect to the two subjects for which day 42 or day 44 data was available, serum uric acid levels approached or exceeded baseline by the last time point measured. Based on the observations from the Phase 1b clinical trial data, it was found that SEL-212 was capable of controlling uric acid levels for at least 30 days in the majority of subjects in Cohort #4.

On a combined basis, a total of 85 subjects have been dosed with either SEL-212 (SVP Rapamycin and pegsiticase), SVP Rapamycin alone or pegsiticase alone in connection with the Phase 1a and Phase 1b clinical trials. It has been generally observed that SEL-212 and its components, SVP Rapamycin and pegsiticase, have been well tolerated. There have been a total of four serious adverse events, or SAEs, in both Phase 1 clinical trials. All SAEs fully resolved.

Figure 5:
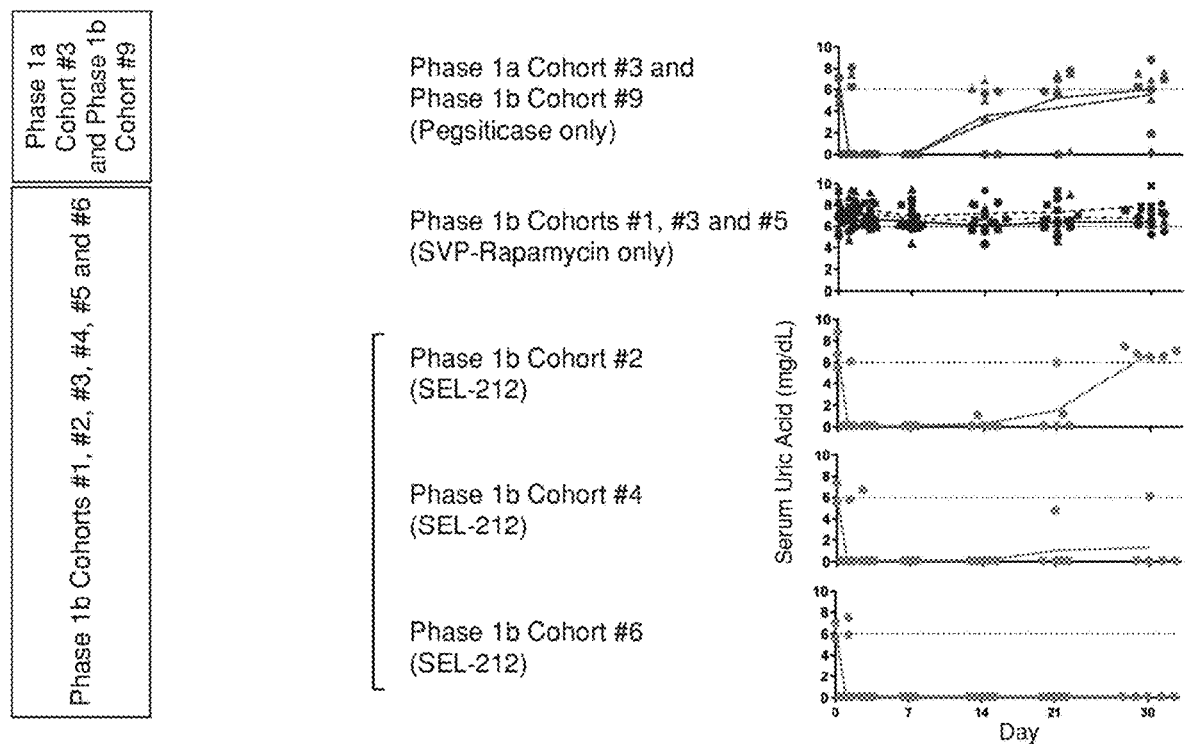
FIG. 5 is a graph showing the serum uric acid levels of Cohort #3 from the Phase 1a clinical and Cohort #9, Cohort #1, Cohort #2, Cohort #3, Cohort #4, Cohort #5 and Cohort #6 from the Phase 1b clinical trial trial.

FIG. 5 shows the serum uric acid levels and uricase-specific ADA levels for each subject in Cohort #3 of the Phase 1a clinical trial and Cohort #9 (Pegsiticase Cohort) of the Phase 1b clinical trial for comparison to the serum uric acid levels and uricase-specific ADA levels for each subject in Cohort #4 (SEL-212 Cohort) and Cohort #6 (SEL-212 Cohort) in the Phase 1b clinical trial. Cohort #3 from the Phase 1a clinical trial is also depicted along with Cohort #9 from the Phase 1b clinical trial for purposes of comparison against Cohort #4 and Cohort #6 from the Phase 1b clinical trial because the subjects in these cohorts received the same fixed dose of pegsiticase. In addition, Cohort #4 from the Phase 1b clinical trial is depicted because the subjects in Cohort #4 from the Phase 1b clinical trial received a higher dose of SVP-Rapamycin than did the subjects in Cohort #2 in the Phase 1b clinical trial. Also included is Cohort #6 from the Phase 1b clinical trial because these subjects received the highest dose of SVP-Rapamycin tested to date—higher than both Cohorts #2 and #4.

Figure 6:
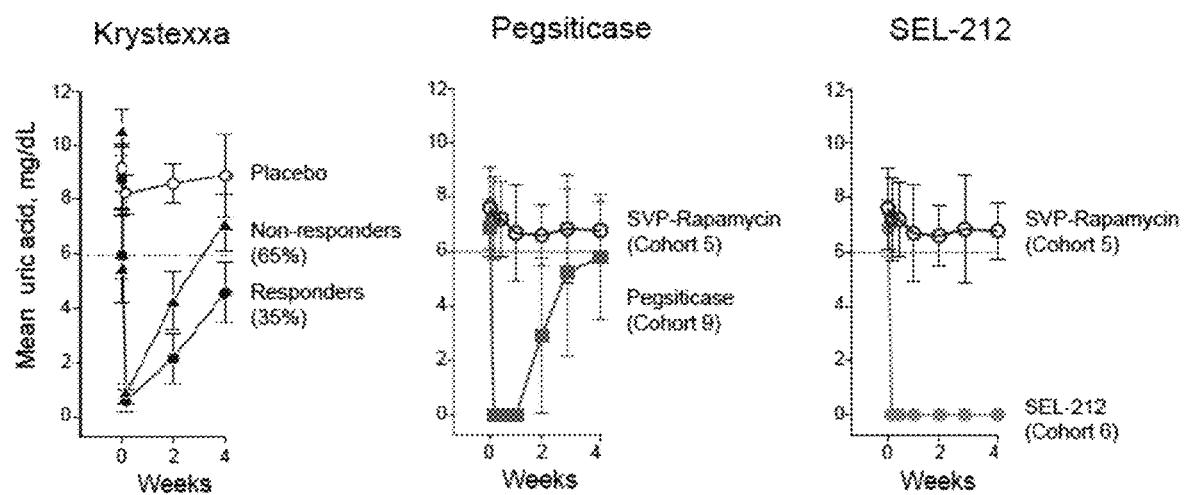
FIG. 6 from left to right shows data from two replicate Kystexxa® trials, in the middle is the data of SVP-Rapamycin alone vs. pegsiticase alone (Cohort #9) and then Rapamycin alone vs. Cohort #6 (a SEL-212 cohort).

FIG. 6 presents a non-head-to-head comparison of the efficacy of SEL-212 in Cohort #6 of the Phase 1b clinical trial with Cohort #5 of the Phase 1b clinical trial and data from two replicate, randomized, double-blind, placebo-controlled clinical trials of KRYSTEXXA® as reported in the Journal of the American Medical Association in 2011. These two KRYSTEXXA® clinical trials included 85 patients who received biweekly doses of KRYSTEXXA®, 84 patients who received monthly doses of KRYSTEXXA® and 43 patients who received a placebo.

KRYSTEXXA® has been approved for the treatment of refractory gout on a biweekly dose regimen whereas the monthly dose regimen of KRYSTEXXA® has not been approved for marketing. The graph on the left below depicts the data for the four-week period after the first dose of Krystexxa® from the cohorts of subjects in the KRYSTEXXA® clinical trials who received monthly doses.

The placebo control subjects, indicated in open circles in FIG. 6, had uric acid levels above 6 mg/dl for the entire four weeks. The KRYSTEXXA®-treated subjects that went on to become responders, as defined by maintenance of uric acid levels below 6 mg/dl for 80% of the time at months three and six, are indicated in black circles. The KRYSTEXXA®-treated subjects that went on to become non-responders, as defined by the inability to maintain uric acid levels below 6 mg/dl for 80% of the time at months three and six, are indicated in black triangles. Only 35% of KRYSTEXXA®-treated subjects in the monthly dosing cohorts were classified as responders. It is notable that, even at four weeks, the mean uric acid levels were above 6 mg/dl in the non-responders, representing 65% of subjects, and were above 4 mg/dl in the responders. 89% of all KRYSTEXXA®-treated subjects developed ADAs. In comparison, the graph on the right in FIG. 6 depicts data from Cohort #5 of the Phase 1b clinical trial, which received a single dose of SVP-Rapamycin alone, and Cohort #6 of the Phase 1b clinical trial, which received a single dose of SEL-212. All five subjects in Cohort #6 of the Phase 1b clinical trial, treated with SEL-212, maintained levels of serum uric acid of less than 0.1 mg/dl through day 30. Subjects in Cohort #5 of the Phase 1b clinical trial, treated with SVP-Rapamycin alone, experienced no significant reduction in uric acid levels, as such levels remained relatively constant over the 30-day period. Also shown is a comparison of data from Cohort #5 of the Phase 1b clinical trial, which received a single dose of SVP-Rapamycin alone, with Cohort #9 of the Phase 1b clinical trial, which received pegstiticase alone.

While it is believed that the above comparison is useful in evaluating the results of Cohort #6 of the Phase 1b clinical trial, the Phase 1b clinical trial and the KRYSTEXXA® clinical trials were separate trials conducted by different investigators at different sites. In addition, there were substantial differences, including, for example, that the KRYSTEXXA® clinical trials were double-blind trials involving a substantial number of patients with refractory gout while the Phase 1b clinical trial evaluated SEL-212 in an unblended manner in a small number of subjects with elevated uric acid levels. Moreover, only the efficacy of SEL-212 with the four-week period following the first injection of KRYSTEXXA® could be compared as SEL-212 had not yet been evaluated in a multi-dose clinical trial.

Additional serum uric acid and uricase-specific ADA data was collected after day 30 for three of the subjects in Cohort #4 (SEL-212 Cohort) that had no or very low serum uric acid and uricase-specific ADA levels at day 30. Data was collected on day 37 for all three of these subjects and again on day 42 or day 44 for two of the three subjects. Each of these three subjects had no or very low uricase-specific ADA levels on day 37, day 42 or day 44, as applicable. Serum uric acid levels remained below baseline on day 37 in all three subjects. With respect to the two subjects for which day 42 or day 44 data was available, serum uric acid levels approached or exceeded baseline by the last time point measured.

Example 2—Phase 2 Clinical Trial

Presented herein is a phase 2 clinical trial of SEL-212. The study consists of multiple doses of SEL-212 concomitantly administered with doses of SEL-037. SEL-212 is a combination of SEL-037 and SEL-110. SEL-037 comprises pegsiticase (Recombinant Pegylated *Candida* Urate Oxidase). SEL-110 is a nanocarrier comprising PLA (poly(D,L-lactide)) and PLA-PEG (poly(D,L-lactide)-block-poly(ethylene-glycol)) encapsulating rapamycin.

SEL-037 can be provided with phosphate buffer and mannitol as excipients. Prior to administration, 6 mg, measured as uricase protein, lyophilized SEL-037 can be reconstituted with 1.1 ml of sterile water for injection, USP (United States Pharmacopeia) which forms a 6 mg/mL concentrated solution. A sufficient volume of reconstituted SEL-037 at 0.2 mg/kg or 0.4 mg/kg, measured as uricase protein, is diluted in 100 mL of 0.9% sodium chloride for injection, USP and dosed as a single intravenous infusion with an infusion pump over 60 minutes.

SEL-110 is provided as a 2 mg/mL, based on rapamycin content, suspension in PBS. The appropriate amount of SEL-110 on a mg/kg basis is drawn into a syringe or syringes and administered as an IV infusion with a syringe infusion pump. If a subject is part of Cohorts 3, 4, 5, 6, 7 and 8 then SEL-110 is administered prior to SEL-037. SEL-110 is delivered by syringe infusion pump at a single steady rate sufficient to deliver the dose volume over a period of 55 minutes concurrently with a 60 minute infusion of 125 mL of normal saline and then the SEL-037 infusion (0.2 mg/kg for Cohorts 3, 5 and 7; 0.4 mg/kg for Cohorts 4, 6 and 8) are started at the 60 minute mark.

96 subjects were divided into 11 dosing cohorts. Cohort 1 receives SEL 037 (pegsiticase alone, 0.2 mg/kg), Cohort 2 receives SEL-037 (pegsiticase alone, 0.4 mg/kg), Cohort 3 receives SEL-212 (with 0.05 mg/kg of SEL-110+0.2 mg/kg pegsiticase), Cohort 4 receives SEL-212 (with 0.05 mg/kg of SEL-110+0.4 mg/kg pegsiticase), Cohort 5 receives SEL-212 (with 0.08 mg/kg of SEL-110+0.2 mg/kg pegsiticase), Cohort 6 receives SEL-212 (with 0.08 mg/kg of SEL-110+0.4 mg/kg pegsiticase), Cohort 7 receives SEL-212 (with 0.1 mg/kg of SEL-110+0.2 mg/kg pegsiticase), Cohort 8 receives SEL-212 (with 0.1 mg/kg of SEL-110+0.4 mg/kg pegsiticase), Cohort 10 receives SEL-212 (with 0.125 mg/kg of SEL-110+0.4 mg/kg pegsiticase, Cohort 11 receives SEL-212 (with 0.15 mg/kg of SEL-110+0.2 mg/kg pegsiticase), and Cohort 12 receives SEL-212 (with 0.15 mg/kg of SEL-110+0.4 mg/kg pegsiticase.

Distribution of Subjects

All enrolled subjects were randomized initially to 4 cohorts such that upon reaching 12 subjects total for all 4 cohorts, each cohort contains 3 subjects. After the completion of at least one treatment cycle the subject experience is evaluated before enrollment is opened to all cohorts. The future enrollment is randomized between all open cohorts.

Premedication for Study Drug Treatments

All subjects received 180 mg fexofenadine orally the night before receiving study drug (12 h±2 h) and again 2±1 hours before receiving study drug (i.e., prior to SEL-037 for Cohorts 1 and 2 or SEL-110 for Cohorts 3-8, 10, 11, and 12). In addition, they also received methylprednisolone 40 mg (or equivalent drug, for example prednisone 50 mg IV or dexamethasone 8 mg IV) intravenously 1±0.5 hour before receiving study drug (i.e., prior to SEL-037 for Cohorts 1 and 2 or SEL-110 for Cohorts 3-8, 10, 11, and 12). This occurs for every treatment dosing of study drug (Part A, Treatment Periods 1-3 and for Part B, Treatment Periods 4 and 5).

Premedication for Gout Flare

All subjects that met all inclusion and exclusion criteria were given premedication for gout flare prevention. The regimen began 1 week prior to the first dosing of study drug and continued for as long as the subject was enrolled in the clinical study. Subjects were given colchicine 1.2 mg as a single loading dose. Then they continued with colchicine 0.6 mg QD for the remainder of their participation in the trial. If there was a contraindication to colchicine, the subject received ibuprofen 600 mg TID or equivalent dose of a NSAID. If there is a contraindication to colchicine and to NSAIDs the subject received no premedication for gout flare. The gout flare prevention medication continued as long as the subject was enrolled in the clinical study. Subjects who began receiving a NSAID as gout flare prevention medication due to a contraindication to colchicine continued to receive the NSAID as long as the subject is enrolled in the study.

Duration of Treatment for Cohort 3, Cohort 4, Cohort 5, Cohort 6, Cohort 7, Cohort 8, Cohort 10, Cohort 11, and Cohort 12

Treatment Period 1—Part A

Subjects were screened within 45 days of dosing. Once they met inclusion/exclusion criteria and all assessments were considered acceptable they were instructed on when to start their premedication (date and medication, Day −7) for the prevention of gout flares. The day of initial dosing of study drug was designated Day 0. Eligible subjects who have been assigned to Cohorts 3, 4, 5, 6, 7 and 8 received a single IV in fusion of SEL-110 (dose based on a mg/kg basis). SEL-110 was delivered by syringe infusion pump at a single steady rate sufficient to deliver the dose volume over a period of 55 minutes. Concurrently to the administration of SEL-110, the subject received a 125 mL of normal saline over 60 minutes. This was followed (±3 minutes) by an infusion delivered by infusion pump of SEL-037 (0.2 mg/kg for Cohorts 3, 5, and 7; 0.4 mg/kg for Cohorts 4, 6 and 8) diluted into 100 mL of normal saline delivered over 60 minutes. Subjects remained in the clinic for 9 hours after the start of the infusion of SEL-110 for safety evaluations and PK blood draws. Subjects returned for PK and PD blood draws on Treatment Period 1, Days 1, 7, 14, 21 and safety and Antibody blood draws on Treatment Period 1, Days 7, 14, 21.

Treatment Period 2—Part A

On the morning of Treatment Period 2, Day 0, subjects reported to the clinic for the dosing of study drug. Eligible subjects who had been assigned to Cohorts 3, 4, 5, 6, 7 and 8 received a single IV infusion of SEL-110 (dose based on a mg/kg basis). SEL-110 was delivered by syringe infusion pump at a single steady rate sufficient to deliver the dose volume over a period of 55 minutes. Concurrently to the administration of SEL-110, the subject received a 125 mL of normal saline over 60 minutes. This was followed (±3 minutes) by an infusion delivered by infusion pump of SEL-037 (0.2 mg/kg for Cohorts 3, 5 and 7; 0.4 mg/kg for Cohorts 4, 6 and 8) diluted into 100 mL of normal saline delivered over 60 minutes. Subjects remained in the clinic for 9 hours after the start of the infusion of SEL-110 for safety evaluations and PK blood draws. Subjects returned for PK and PD on Treatment Period 2, Days 1, 7, 14 and 21 and safety and antibody blood draws on Treatment Period 2, Days 7, 14 and 21.

Treatment Period 3—Part A

On the morning of Treatment Period 3, Day 0 subjects will report to the clinic for the dosing of study drug. Eligible subjects who have been assigned to Cohorts 3, 4, 5, 6, 7 and 8 will receive a single IV infusion of SEL-110 (dose based on a mg/kg basis). SEL-110 will be delivered by syringe infusion pump at a single steady rate sufficient to deliver the dose volume over a period of 55 minutes. Concurrently to the administration of SEL-110, the subject will receive a 125 mL of normal saline over 60 minutes. This will be followed (±3 minutes) by an infusion delivered by infusion pump of SEL-037 (0.2 mg/kg for Cohorts 3, 5 and 7; 0.4 mg/kg for Cohorts 4, 6 and 8) diluted into 100 mL of normal saline delivered over 60 minutes. Subjects will remain in the clinic for 9 hours after the start of the infusion of SEL-110 for safety evaluations and PK blood draws. Subjects will return for PK and PD blood draws on Treatment Period 3, Days 1, 7, 14 and 21 and safety and antibody blood draws on Treatment Period 3, Days 7, 14 and 21.

Treatment Period 4—Part B

On the morning of Treatment Period 4, Day 0 subjects will report to the clinic for the dosing of study drug. Subjects will receive a single IV infusion of SEL-037 (0.2 mg/kg for Cohorts 3, 5 and 7; 0.4 mg/kg for Cohorts 4, 6 and 8) diluted into 100 mL of normal saline over 60 minutes by infusion pump. Subjects will remain in the clinic for 9 hours after the start of the infusion of SEL-037 for safety evaluations and PK blood draws. Subjects will return for PK and PD blood draws on Treatment Period 4, Days 1, 7, 14 and 21 and safety and antibody blood draws on Treatment Period 4, Days 7, 14 and 21.

Treatment Period 5—Part B

On the morning of Treatment Period 5, Day 0 subjects will report to the clinic for the dosing of study drug. Subjects will receive a single IV infusion of SEL-037 (0.2 mg/kg for Cohorts 3, 5 and 7; 0.4 mg/kg for Cohorts 4, 6 and 8) diluted into 100 ml of normal saline over 60 minutes by infusion pump. Subjects will remain in the clinic for 9 hours after the start of the infusion of SEL-037 for safety evaluations and PK blood draws. Subjects will return for PK and PD blood draws on Treatment Period 5, Days 1, 7, 14 and 21 and safety and antibody blood draws on Treatment Period 5, Days 7, 14 and 21.

Results

When pegsiticase was administered alone in the Phase 1 described in Example 1, 24% (23 out of 96 patients) of those with a history of gout had signs of gout flare in the first month after receiving the study drug (Table 1). In contrast, however, when PLA/PLA-PEG synthetic nanocarriers comprising rapamycin were concomitantly administered with pegsiticase in a Phase 2 trial described in Example 3, 22% of subjects who had a history of gout (20 out of 90 enrolled patients) reported gout flare in the first month (Table 2).

TABLE 1

Flares in subjects with history of gout

| Subject | Flare in 1st month | Dose of SEL-037 |
|---|---|---|
| 1 | Yes | 0.2 mg/kg |
| 2 | No | 0.2 mg/kg |
| 3 | No | 0.4 mg/kg |
| 4 | No | 0.2 mg/kg |
| 5 | No | 0.4 mg/kg |
| 6 | No | 0.2 mg/kg |
| 7 | No | 0.4 mg/kg |
| 8 | Yes | 0.4 mg/kg |
| 9 | No | 0.2 mg/kg |
| 10 | No | 0.4 mg/kg |
| 11 | No | 0.2 mg/kg |
| 12 | No | 0.4 mg/kg |
| 13 | No | 0.4 mg/kg |
| 14 | No | 0.4 mg/kg |
| 15 | No | 0.2 mg/kg |
| 16 | No | 0.2 mg/kg |
| 17 | No | 0.4 mg/kg |
| 18 | Yes | 0.2 mg/kg |
| 19 | No | 0.2 mg/kg |
| 20 | No | 0.4 mg/kg |
| 21 | No | 0.4 mg/kg |
| 22 | Yes | 0.4 mg/kg |
| 23 | No | 0.4 mg/kg |
| 24 | No | 0.2 mg/kg |
| 25 | No | 0.2 mg/kg |
| 26 | Yes | 0.4 mg/kg |
| 27 | No | 0.2 mg/kg |
| 28 | No | 0.2 mg/kg |
| 29 | Yes | 0.2 mg/kg |
| 30 | No | 0.2 mg/kg |
| 31 | No | 0.4 mg/kg |
| 32 | Yes | 0.2 mg/kg |
| 33 | Yes | 0.2 mg/kg |
| 34 | Yes | 0.4 mg/kg |
| 35 | Yes | 0.2 mg/kg |
| 36 | No | 0.2 mg/kg |
| 37 | No | 0.2 mg/kg |
| 38 | No | 0.2 mg/kg |
| 39 | No | 0.4 mg/kg |
| 40 | No | 0.4 mg/kg |
| 41 | Yes | 0.2 mg/kg |
| 42 | No | 0.4 mg/kg |
| 43 | Yes | 0.4 mg/kg |
| 44 | No | 0.4 mg/kg |
| 45 | Yes | 0.4 mg/kg |
| 46 | Yes | 0.4 mg/kg |
| 47 | No | 0.4 mg/kg |
| 48 | No | 0.4 mg/kg |
| 49 | Yes | 0.4 mg/kg |
| 50 | No | 0.2 mg/kg |
| 51 | No | 0.2 mg/kg |
| 52 | Yes | 0.2 mg/kg |
| 53 | No | 0.2 mg/kg |
| 54 | No | 0.4 mg/kg |
| 55 | No | 0.4 mg/kg |
| 56 | No | 0.4 mg/kg |
| 57 | Yes | 0.4 mg/kg |
| 58 | No | 0.4 mg/kg |
| 59 | No | 0.4 mg/kg |
| 60 | No | 0.4 mg/kg |
| 61 | No | 0.4 mg/kg |
| 62 | No | 0.4 mg/kg |
| 63 | No | 0.4 mg/kg |
| 64 | No | 0.4 mg/kg |
| 65 | No | 0.2 mg/kg |
| 66 | No | 0.2 mg/kg |
| 67 | No | 0.4 mg/kg |
| 68 | No | 0.2 mg/kg |
| 69 | Yes | 0.4 mg/kg |
| 70 | No | 0.4 mg/kg |
| 71 | No | 0.4 mg/kg |
| 72 | No | 0.4 mg/kg |
| 73 | Yes | 0.4 mg/kg |
| 74 | No | 0.4 mg/kg |
| 75 | No | 0.4 mg/kg |
| 76 | No | 0.2 mg/kg |
| 77 | No | 0.4 mg/kg |
| 78 | No | 0.4 mg/kg |
| 79 | Yes | 0.2 mg/kg |
| 80 | No | 0.4 mg/kg |
| 81 | No | 0.4 mg/kg |
| 82 | No | 0.4 mg/kg |
| 83 | Yes | 0.4 mg/kg |
| 84 | No | 0.4 mg/kg |
| 85 | No | 0.4 mg/kg |
| 86 | No | 0.4 mg/kg |
| 87 | No | 0.2 mg/kg |
| 88 | No | 0.2 mg/kg |
| 89 | No | 0.4 mg/kg |
| 90 | No | 0.4 mg/kg |
| 91 | Yes | 0.4 mg/kg |
| 92 | No | 0.2 mg/kg |
| 93 | No | 0.2 mg/kg |
| 94 | No | 0.2 mg/kg |
| 95 | Yes | 0.2 mg/kg |
| 96 | No | 0.4 mg/kg |

TABLE 2

Flares in SEL-212 subjects

| SEL-212 subjects with gout | Flare in 1st month | Cohort/dose |
|---|---|---|
| 1 | No | Cohort 3/SEL-110 0.05 mg/kg; SEL-037 0.2 mg/kg |
| 2 | No | Cohort 4/SEL-110 0.05 mg/kg; SEL-037 0.4 mg/kg |
| 3 | No | Cohort 3/SEL-110 0.05 mg/kg; SEL-037 0.2 mg/kg |
| 4 | No | Cohort 4/SEL-110 0.05 mg/kg; SEL-037 0.4 mg/kg |
| 5 | No | Cohort 5/SEL-110 0.08 mg/kg; SEL-037 0.2 mg/kg |
| 6 | No | Cohort 6/SEL-110 0.08 mg/kg; SEL-037 0.4 mg/kg |
| 7 | Yes | Cohort 10/SEL-110 0.125 mg/kg; SEL-037 0.4 mg/kg |
| 8 | No | Cohort 3/SEL-110 0.05 mg/kg; SEL-037 0.2 mg/kg |
| 9 | No | Cohort 4/SEL-110 0.05 mg/kg; SEL-037 0.4 mg/kg |
| 10 | No | Cohort 7/SEL-110 0.1 mg/kg; SEL-037 0.2 mg/kg |
| 11 | No | Cohort 8/SEL-110 0.1 mg/kg; SEL-037 0.4 mg/kg |
| 12 | No | Cohort 8/SEL-110 0.1 mg/kg; SEL-037 0.4 mg/kg |
| 13 | No | Cohort 6/SEL-110 0.08 mg/kg; SEL-037 0.4 mg/kg |
| 14 | No | Cohort 11/SEL-110 0.15 mg/kg; SEL-037 0.2 mg/kg |
| 15 | No | Cohort 11/SEL-110 0.15 mg/kg; SEL-037 0.2 mg/kg |
| 16 | No | Cohort 4/SEL-110 0.05 mg/kg; SEL-037 0.4 mg/kg |
| 17 | Yes | Cohort 5/SEL-110 0.08 mg/kg; SEL-037 0.2 mg/kg |
| 18 | No | Cohort 3/SEL-110 0.05 mg/kg; SEL-037 0.2 mg/kg |
| 19 | No | Cohort 4/SEL-110 0.05 mg/kg; SEL-037 0.4 mg/kg |
| 20 | No | Cohort 6/SEL-110 0.08 mg/kg; SEL-037 0.4 mg/kg |
| 21 | Yes | Cohort 8/SEL-110 0.1 mg/kg; SEL-037 0.4 mg/kg |
| 22 | No | Cohort 8/SEL-110 0.1 mg/kg; SEL-037 0.4 mg/kg |
| 23 | No | Cohort 7/SEL-110 0.1 mg/kg; SEL-037 0.2 mg/kg |
| 24 | No | Cohort 7/SEL-110 0.1 mg/kg; SEL-037 0.2 mg/kg |
| 25 | Yes | Cohort 8/SEL-110 0.1 mg/kg; SEL-037 0.4 mg/kg |
| 26 | No | Cohort 7/SEL-110 0.1 mg/kg; SEL-037 0.2 mg/kg |
| 27 | No | Cohort 7/SEL-110 0.1 mg/kg; SEL-037 0.2 mg/kg |
| 28 | Yes | Cohort 7/SEL-110 0.1 mg/kg; SEL-037 0.2 mg/kg |

TABLE 2-continued

Flares in SEL-212 subjects

| SEL-212 subjects with gout | Flare in 1st month | Cohort/dose |
|---|---|---|
| 29 | No | Cohort 3/SEL-110 0.05 mg/kg; SEL-037 0.2 mg/kg |
| 30 | Yes | Cohort 3/SEL-110 0.05 mg/kg; SEL-037 0.2 mg/kg |
| 31 | Yes | Cohort 4/SEL-110 0.05 mg/kg; SEL-037 0.4 mg/kg |
| 32 | No | Cohort 3/SEL-110 0.05 mg/kg; SEL-037 0.2 mg/kg |
| 33 | No | Cohort 3/SEL-110 0.05 mg/kg; SEL-037 0.2 mg/kg |
| 34 | No | Cohort 5/SEL-110 0.08 mg/kg; SEL-037 0.2 mg/kg |
| 35 | No | Cohort 6/SEL-110 0.08 mg/kg; SEL-037 0.4 mg/kg |
| 36 | No | Cohort 6/SEL-110 0.08 mg/kg; SEL-037 0.4 mg/kg |
| 37 | Yes | Cohort 5/SEL-110 0.08 mg/kg; SEL-037 0.2 mg/kg |
| 38 | No | Cohort 8/SEL-110 0.1 mg/kg; SEL-037 0.4 mg/kg |
| 39 | Yes | Cohort 8/SEL-110 0.1 mg/kg; SEL-037 0.4 mg/kg |
| 40 | No | Cohort 10/SEL-110 0.125 mg/kg; SEL-037 0.4 mg/kg |
| 41 | Yes | Cohort 10/SEL-110 0.125 mg/kg; SEL-037 0.4 mg/kg |
| 42 | Yes | Cohort 8/SEL-110 0.1 mg/kg; SEL-037 0.4 mg/kg |
| 43 | No | Cohort 8/SEL-110 0.1 mg/kg; SEL-037 0.4 mg/kg |
| 44 | No | Cohort 12/SEL-110 0.15 mg/kg; SEL-037 0.4 mg/kg |
| 45 | Yes | Cohort 12/SEL-110 0.15 mg/kg; SEL-037 0.4 mg/kg |
| 46 | No | Cohort 12/SEL-110 0.15 mg/kg; SEL-037 0.4 mg/kg |
| 47 | No | Cohort 11/SEL-110 0.15 mg/kg; SEL-037 0.2 mg/kg |
| 48 | Yes | Cohort 11/SEL-110 0.15 mg/kg; SEL-037 0.2 mg/kg |
| 49 | No | Cohort 7/SEL-110 0.1 mg/kg; SEL-037 0.2 mg/kg |
| 50 | No | Cohort 6/SEL-110 0.08 mg/kg; SEL-037 0.4 mg/kg |
| 51 | No | Cohort 10/SEL-110 0.125 mg/kg; SEL-037 0.4 mg/kg |
| 52 | Yes | Cohort 10/SEL-110 0.125 mg/kg; SEL-037 0.4 mg/kg |
| 53 | No | Cohort 12/SEL-110 0.15 mg/kg; SEL-037 0.4 mg/kg |
| 54 | No | Cohort 12/SEL-110 0.15 mg/kg; SEL-037 0.4 mg/kg |
| 55 | No | Cohort 10/SEL-110 0.125 mg/kg; SEL-037 0.4 mg/kg |
| 56 | No | Cohort 6/SEL-110 0.08 mg/kg; SEL-037 0.4 mg/kg |
| 57 | No | Cohort 4/SEL-110 0.05 mg/kg; SEL-037 0.4 mg/kg |
| 58 | No | Cohort 4/SEL-110 0.05 mg/kg; SEL-037 0.4 mg/kg |
| 59 | No | Cohort 5/SEL-110 0.08 mg/kg; SEL-037 0.2 mg/kg |
| 60 | No | Cohort 5/SEL-110 0.08 mg/kg; SEL-037 0.2 mg/kg |
| 61 | No | Cohort 4/SEL-110 0.05 mg/kg; SEL-037 0.4 mg/kg |
| 62 | No | Cohort 3/SEL-110 0.05 mg/kg; SEL-037 0.2 mg/kg |
| 63 | Yes | Cohort 4/SEL-110 0.05 mg/kg; SEL-037 0.4 mg/kg |
| 64 | No | Cohort 6/SEL-110 0.08 mg/kg; SEL-037 0.4 mg/kg |
| 65 | No | Cohort 6/SEL-110 0.08 mg/kg; SEL-037 0.4 mg/kg |
| 66 | No | Cohort 12/SEL-110 0.15 mg/kg; SEL-037 0.4 mg/kg |
| 67 | Yes | Cohort 12/SEL-110 0.15 mg/kg; SEL-037 0.4 mg/kg |
| 68 | No | Cohort 12/SEL-110 0.15 mg/kg; SEL-037 0.4 mg/kg |
| 69 | No | Cohort 10/SEL-110 0.125 mg/kg; SEL-037 0.4 mg/kg |
| 70 | No | Cohort 11/SEL-110 0.15 mg/kg; SEL-037 0.2 mg/kg |
| 71 | No | Cohort 8/SEL-110 0.1 mg/kg; SEL-037 0.4 mg/kg |
| 72 | No | Cohort 6/SEL-110 0.08 mg/kg; SEL-037 0.4 mg/kg |
| 73 | Yes | Cohort 7/SEL-110 0.1 mg/kg; SEL-037 0.2 mg/kg |
| 74 | No | Cohort 8/SEL-110 0.1 mg/kg; SEL-037 0.4 mg/kg |
| 75 | No | Cohort 10/SEL-110 0.125 mg/kg; SEL-037 0.4 mg/kg |
| 76 | No | Cohort 10/SEL-110 0.125 mg/kg; SEL-037 0.4 mg/kg |
| 77 | Yes | Cohort 10/SEL-110 0.125 mg/kg; SEL-037 0.4 mg/kg |
| 78 | No | Cohort 12/SEL-110 0.15 mg/kg; SEL-037 0.4 mg/kg |
| 79 | No | Cohort 12/SEL-110 0.15 mg/kg; SEL-037 0.4 mg/kg |
| 80 | No | Cohort 12/SEL-110 0.15 mg/kg; SEL-037 0.4 mg/kg |
| 81 | No | Cohort 11/SEL-110 0.15 mg/kg; SEL-037 0.2 mg/kg |
| 82 | No | Cohort 11/SEL-110 0.15 mg/kg; SEL-037 0.2 mg/kg |
| 83 | No | Cohort 10/SEL-110 0.125 mg/kg; SEL-037 0.4 mg/kg |
| 84 | No | Cohort 10/SEL-110 0.125 mg/kg; SEL-037 0.4 mg/kg |
| 85 | Yes | Cohort 6/SEL-110 0.08 mg/kg; SEL-037 0.4 mg/kg |
| 86 | No | Cohort 7/SEL-110 0.1 mg/kg; SEL-037 0.2 mg/kg |
| 87 | No | Cohort 7/SEL-110 0.1 mg/kg; SEL-037 0.2 mg/kg |
| 88 | No | Cohort 7/SEL-110 0.1 mg/kg; SEL-037 0.2 mg/kg |
| 89 | Yes | Cohort 11/SEL-110 0.15 mg/kg; SEL-037 0.2 mg/kg |
| 90 | No | Cohort 10/SEL-110 0.125 mg/kg; SEL-037 0.4 mg/kg |

A phase 2 study was undertaken (Example 2). This study involved the administration of multiple IV infusions of PLA/PLA-PEG synthetic nanocarriers comprising rapamycin together with pegsiticase in order to assess its safety and tolerability. 96 subjects were randomized and dosed, with 27 subjects (28%) reported as receiving gout flare prophylaxis with colchicine/NSAIDs (Table 3).

TABLE 3

Subjects who suffered from gout flare following treatment

| SEL-212 subject | Cohort | Dose | Gout flare prophylaxis with colchicine/NSAID |
|---|---|---|---|
| 1 | 1 | SEL-037 0.2 mg/kg | Yes |
| 2 | 10 | SEL-110 0.125 mg/kg; SEL-037 0.4 mg/kg | Yes |
| 3 | 5 | SEL-110 0.08 mg/kg; SEL-037 0.2 mg/kg | Yes |
| 4 | 8 | SEL-110 0.1 mg/kg; SEL-037 0.4 mg/kg | Yes |
| 5 | 8 | SEL-110 0.1 mg/kg; SEL-037 0.4 mg/kg | Yes |
| 6 | 8 | SEL-110 0.1 mg/kg; SEL-037 0.4 mg/kg | Yes |
| 7 | 7 | SEL-110 0.1 mg/kg; SEL-037 0.2 mg/kg | Yes |
| 8 | 7 | SEL-110 0.1 mg/kg; SEL-037 0.2 mg/kg | Yes |
| 9 | 7 | SEL-110 0.1 mg/kg; SEL-037 0.2 mg/kg | Yes |
| 10 | 3 | SEL-110 0.05 mg/kg; SEL-037 0.2 mg/kg | Yes |
| 11 | 3 | SEL-110 0.05 mg/kg; SEL-037 0.2 mg/kg | Yes |
| 12 | 1 | SEL-037 0.2 mg/kg | Yes |
| 13 | 4 | SEL-110 0.05 mg/kg; SEL-037 0.4 mg/kg | Yes |
| 14 | 1 | SEL-037 0.2 mg/kg | Yes |
| 15 | 6 | SEL-110 0.08 mg/kg; SEL-037 0.4 mg/kg | Yes |
| 16 | 5 | SEL-110 0.08 mg/kg; SEL-037 0.2 mg/kg | Yes |
| 17 | 8 | SEL-110 0.1 mg/kg; SEL-037 0.4 mg/kg | Yes |
| 18 | 10 | SEL-110 0.125 mg/kg; SEL-037 0.4 mg/kg | Yes |
| 19 | 8 | SEL-110 0.1 mg/kg; SEL-037 0.4 mg/kg | Yes |
| 20 | 12 | SEL-110 0.15 mg/kg; SEL-037 0.4 mg/kg | Yes |
| 21 | 11 | SEL-110 0.15 mg/kg; SEL-037 0.2 mg/kg | Yes |
| 22 | 10 | SEL-110 0.125 mg/kg; SEL-037 0.4 mg/kg | Yes |
| 23 | 4 | SEL-110 0.05 mg/kg; SEL-037 0.4 mg/kg | Yes |
| 24 | 12 | SEL-110 0.15 mg/kg; SEL-037 0.4 mg/kg | No |
| 25 | 7 | SEL-110 0.1 mg/kg; SEL-037 0.2 mg/kg | Yes |
| 26 | 10 | SEL-110 0.125 mg/kg; SEL-037 0.4 mg/kg | Yes |
| 27 | 6 | SEL-110 0.08 mg/kg; SEL-037 0.4 mg/kg | Yes |
| 28 | 11 | SEL-110 0.15 mg/kg; SEL-037 0.2 mg/kg | Yes |

Flare rates in the above subjects were compared to the flare rates in the pegloticase trials. Those subjects who received gout flare prophylaxis (with colchicine or NSAIDS) only were chosen to match the pegloticase subject conditions. Flare frequency (number of flares per patient month) was selected as a measure by which to compare flare rates. This measure was chosen based on the fact that the trial data covers 5 treatment cycles; while the pegloticase trials varied in length from 35 days (Sundy et al., Pharmacokinetics and pharmacodynamics of intravenous PEGylated recombinant mammalian urate oxidase in patients with refractory gout. Arthritis and Rheumatism. Vol. 56, No. 3, Mar. 2007, pp 1021-1028) to 6 months (John S. Sundy, MD, PhD; Herbert S. B. Baraf, MD; Robert A. Yood, MD; et al. Efficacy and Tolerability of Pegloticase for the Treatment of Chronic Gout in Patients Refractory to Conventional Treatment: Two Randomized Controlled Trials. JAMA. 2011; 306(7):711-720). Patient monthly rates were chosen to be able to compare between trials.

For the SEL-212 study, all subjects who met all inclusion and exclusion criteria were given pre-medication to prevent gout flare. The pre-medication regimen began one week prior to the first dosing of study drug and continued for the duration of the clinical study. Subjects were given colchicine (1.2 mg) as a single loading dose. They then continued to receive colchicine (one 0.6 mg dose daily) for the remainder of their participation in the trial. If there was a contraindication to colchicine, the subject received ibuprofen (600 mg TID) or an equivalent NSAID unless the subject had a contraindication to NSAIDs generally. If the subject has a contraindication to colchicine and to NSAIDs, then no pre-medication was given. The gout flare prevention medication continued for the duration of the clinical study. Subjects who began receiving a NSAID as gout flare prevention medication due to a contraindication to colchicine or under a previous version of this protocol continued to receive the NSAID for the duration of the study.

Subjects also received pre-medication with antihistamines and steroids, consisting of 180 mg fexofenadine (oral) twice times (evening before (−12 h±2 h, self-administered) and −2 h±1 hours before receiving the study drug) and 40 mg methylprednisolone (or equivalent drug, for example prednisone 50 mg IV or dexamethasone 8 mg IV) intravenously −1 h±0.5 hours before receiving the study drug (i.e., prior to SEL-037 for Cohorts 1 and 2 and Part B of all cohorts or prior to SEL-110 for Cohorts 3-8, 10, 11, and 12) to reduce infusion reactions.

Cohorts 3 and 4 were grouped together for this analysis, as they were given the same dose of synthetic nanocarriers comprising rapamycin (0.05 mg/kg), and likewise cohorts 5 and 6 have been grouped together (with a synthetic nanocarrier comprising rapamycin dose of 0.08 mg/kg). In cohorts 1-12, ninety-six subjects have been dosed with a total of 238 treatment cycles. Not all subjects received all treatments, as certain subjects were discontinued following protocol changes. Twenty-nine subjects had 49 gout flares reported during the 238 treatment cycles. This can be equated to 21 flares per treatment cycle; in other words, a flare frequency of 0.21 flares per patient month.

Figure 2:
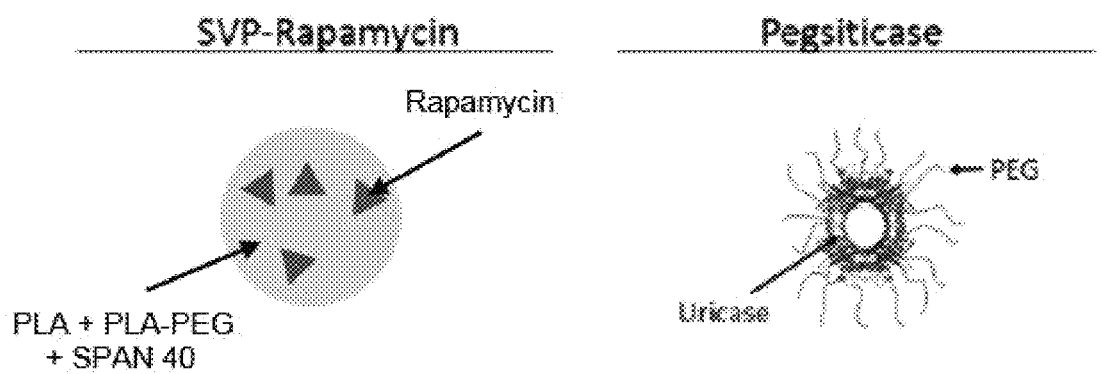
FIG. 2 is a cartoon representation of the components of SEL-212.

For comparison, the Phase 3 pegloticase trials (John S. Sundy, MD, PhD; Herbert S. B. Baraf, MD; Robert A. Yood, MD; et al. Efficacy and Tolerability of Pegloticase for the Treatment of Chronic Gout in Patients Refractory to Conventional Treatment: Two Randomized Controlled Trials. JAMA. 2011; 306(7):711-720) were examined to determine the number of flares per month and the area under the curve (AUC) of mean serum uric acid (sUA) levels over time (up to 20 weeks). Subjects were given 0.6 mg of colchicine once or twice daily (or a nonsteroidal anti-inflammatory drug) one week before first infusion, which continued throughout the study. The study also included prophylaxis against infusion related reactions (IRs) before each infusion. The subjects were administered oral fexofenadine (60 mg) the evening before and again immediately before, the infusion, as well as acetaminophen 1000 mg) and IV hydrocortisone (200 mg) immediately before the infusion. Data points were obtained from Table 2, which presents the biweekly/monthly flare per patient month. Data points were also identified using a graph digitizer for FIG. 2 of the aforementioned reference. The data was extrapolated to 20 weeks. The AUC of mean sUA levels over time (up to 20 weeks) and the flares per patient month were calculated using the combined weighted average for responders and non-responders for sUA AUC. The AUC of the biweekly group was 12.3 of responders; 102.0 was the AUC of the biweekly group of non-responders cut to 20 weeks. Similar calculations were performed to obtain the monthly data.

Further comparisons can be made with the primary branded oral uric acid lowering medication, febuxostat. In a phase 3, randomized, double-blind, multi-center trial, the safety and efficacy of febuxostat was studied over 52 weeks (Michael A. Becker, M.D., H. Ralph Schumacher, Jr., M.D., Robert L. Wortmann, M.D., Patricia A. MacDonald, B.S.N., N.P., Denise Eustace, B.A., William A. Palo, M.S., Janet Streit, M.S., and Nancy Joseph-Ridge, M.D. Febuxostat Compared with Allopurinol in Patients with Hyperuricemia and Gout. N Engl J Med 2005; 353:2450-2461Dec. 8, 2005). The comparison period for this analysis included only the first 8 weeks of that study, when gout flare prophylaxis (naproxen or colchicine) was administered. Data points were identified using a graph digitizer for FIG. 1 of the above reference. At a dose of 80 mg/day, 55 out of 255 subjects required treatment for at least one gout flare. This would be the equivalent to a flare frequency of at least 0.22 flares per patient month, and possibly more. At a dose of 120 mg/day, 90 out of 250 subjects required treatment for at least one gout flare, equating to at least a flare frequency of 0.36 flares per patient month, and possibly more.

The tabulated data outlining the comparison in flare frequency between the different medications alongside their efficacy in reducing serum uric acid (sUA) is compiled in Table 4.

TABLE 4

Flares per patient month compared with other uric acid lowering treatments

| Medication and dosage | Flares per patient month | Area Under Curve of Mean sUA Levels Over Time Up to 20 Weeks | Flares per patient month * AUC |
| --- | --- | --- | --- |
| SEL-212 monthly | 0.21 | 15.3 | 3.21 |
| Pegloticase biweekly | 0.52 | 64.0 | 33.28 |
| Pegloticase monthly | 0.70 | 94.4 | 66.05 |
| Febuxostat 80 mg/day | 0.22 | 108.3 | 23.83 |
| Febuxostat 120 mg/day | 0.36 | 93.4 | 33.62 |

The flare frequency is clearly reduced for the subjects who received the rapamycin-containing nanocarrier concomitantly administered with pegsiticase as compared to all of the other medications. This unexpected outcome is significantly better than with other therapies as shown in Table 4. This also has the benefit for patient adherence to uric acid lowering therapies, such as uricase, as adherence is greatly reduced when rebound flares occur following initiation of therapy (Treatment of chronic gouty arthritis: it is not just about urate-lowering therapy. Schlesinger N—Semin. Arthritis Rheum.—Oct. 1, 2012; 42 (2); 155-65). In addition, a combination assessment of glare frequency as well as the area under the curve of mean sUA levels over time show both improved efficacy and reduced gout flares. This finding was surprising, as typically improved efficacy in sUA removal can result in increased gout flares. Here, with the SEL-212 study drug and anti-inflammatory treatment, both efficacy and gout flare reduction can be achieved.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method, comprising:
concomitantly administering monthly to a subject in need thereof 1) a composition comprising synthetic nanocarriers comprising poly(D,L-lactide) (PLA) and poly(D,L-lactide)-poly(ethylene glycol) (PLA-PEG) and comprising a rapalog and 2) a composition comprising pegadricase; and further comprising administering 3) an anti-inflammatory therapeutic, wherein the anti-inflammatory therapeutic is colchicine or ibuprofen, wherein when the anti-inflammatory therapeutic is colchicine, 1.2 mg colchicine is administered once one week prior to the first concomitant administration of 1) and 2) and subsequently 0.6 mg colchicine is administered once per day, and wherein when the anti-inflammatory therapeutic is ibuprofen, 600 mg ibuprofen is administered three times a day starting one week prior to the first concomitant administration of 1) and 2).

2. The method of claim 1, wherein the anti-inflammatory therapeutic is ibuprofen.

3. The method of claim 1, wherein the anti-inflammatory therapeutic is colchicine.

4. The method of claim 1, wherein the method further comprises administering to the subject one or more compositions comprising an infusion reaction therapeutic.

5. The method of claim 4, wherein the one or more compositions comprising an infusion reaction therapeutic comprises an antihistamine and/or a corticosteroid.

6. The method of claim 5, wherein the antihistamine is fexofenadine.

7. The method of claim 5, wherein the corticosteroid is methylprednisolone, prednisone or dexamethasone.

8. The method of claim 4, wherein the one or more compositions comprising an infusion reaction therapeutic is/are administered at least once prior to the composition comprising synthetic nanocarriers comprising a rapalog and the composition comprising pegadricase.

9. The method of claim 8, wherein the composition(s) comprising an infusion reaction therapeutic is administered at least twice prior to the composition comprising synthetic nanocarriers comprising a rapalog and the composition comprising pegadricase.

10. The method of claim 4, wherein the composition(s) comprising an infusion reaction therapeutic is administered within 24 hours of the composition comprising synthetic nanocarriers comprising a rapalog and the composition comprising pegadricase.

11. The method of claim 1, wherein the rapalog is rapamycin.

12. The method of claim 1, wherein the subject is human.

* * * * *

UNITED STATES PATENT AND TRADEMARK OFFICE
CERTIFICATE OF CORRECTION

PATENT NO. : 11,426,451 B2
APPLICATION NO. : 15/917742
DATED : August 30, 2022
INVENTOR(S) : Lloyd Johnston It is certified that error appears in the above-identified patent and that said Letters Patent is hereby corrected as shown below:

On the Title Page

Item (71) Applicants:
"Selecta Biosciences, Inc., Watertown, MA (US); Lloyd Johnston, Belmont, MA (US)"
Should read:
--Selecta Biosciences, Inc., Watertown, MA (US)--

Signed and Sealed this
Twenty-seventh Day of June, 2023

Katherine Kelly Vidal
*Director of the United States Patent and Trademark Office*